(12) United States Patent
Shi

(10) Patent No.: US 6,348,608 B1
(45) Date of Patent: Feb. 19, 2002

(54) CATALYTIC ASYMMETRIC EPOXIDATION

(76) Inventor: Yian Shi, 1500 W. Plum St., Apt. 336 C, Ft. Collins, CO (US) 55521

( * ) Notice: Subject to any disclaimer, the term of this patent is extended or adjusted under 35 U.S.C. 154(b) by 0 days.

(21) Appl. No.: 09/284,054

(22) PCT Filed: Oct. 8, 1997

(86) PCT No.: PCT/US97/18310

§ 371 Date: Apr. 6, 1999

§ 102(e) Date: Apr. 6, 1999

(87) PCT Pub. No.: WO98/15544

PCT Pub. Date: Apr. 16, 1998

Related U.S. Application Data

(60) Provisional application No. 60/028,009, filed on Oct. 8, 1996.

(51) Int. Cl.[7] .................... C07D 301/12; C07D 301/14
(52) U.S. Cl. .................... 549/524; 549/333; 549/334; 549/525; 549/529; 549/531
(58) Field of Search .................... 549/524, 333, 549/334, 525, 529, 531

(56) References Cited

U.S. PATENT DOCUMENTS

| | | | |
|---|---|---|---|
| 5,403,549 A | 4/1995 | McNeil et al. | 422/29 |
| 5,414,078 A | 5/1995 | Liotta et al. | 536/26.71 |

OTHER PUBLICATIONS

Kurihara et al, "Stereoselective Epoxidation with Dioxiranes Generated from Ketones", Tetrahedron Letters, vol. 35, No. 10, pp. 1577–1580, 1994.*
Murray et al, J. Am. Chem. Soc., 114(4), pp. 1346–1351, 1992.*
Tu et al., "An Efficient Asymmetric Epoxidation Method for trans–Olefins Mediated by a Fructose–Derived Ketone," J. Am. Chem. Soc., 1996, 118, 9806–9807.
Wang et al., "An Efficient Catalytic Asymmetric Epoxidation Method," J. Am. Chem. Soc., 1997, 119, 11224–11235.
Wang et al., "A Dramatic pH Effect Leads to a Catalytic Asymmetric Epoxidation," J. Org. Chem., 1997, 62, 2328–2329.
Wang and Shi, "A New Type of Ketone Catalyst for Asymmetric Epoxidation," J. Org. Chem., 1997, 62, 8622–8623.
Kurihara et al., "Stereoselective Epoxidation with Dioxiranes Generated from Ketones," Tet. Lett., 1994, 35, 1577–1580.
Denmark, et al., "Catalytic Epoxidation of Alkenes with Oxone," J. Org. Chem., 1995, 60, 1391–1407.
Cicala et al., "Stereo– and Regioselectivities in the Epoxidation of Some Allylic Alcohols by the Dioxirane Intermediate Generated in the Reaction of Potassium Caroate with Acetone," J. Org. Chem., 1982, 47, 2670–2673.
Curci et al., "Epoxidation of Alkenes by Dioxirane Intermediates Generated in the Reaction of Potassium Caroate with Ketones," J. Org. Chem., 1980, 45, 4758–4760.
Besse and Veschambre, "Chemical and Biological Synthesis of Chiral Epoxides," Tetrahedron, 1994, 50, 8885–8927.
Curci et al., "Asymmetric Epoxidation of Unfunctionalized Alkenes by Dioxirane Intermediates Generated from Potassium Peroxomonosulphate and Chiral Ketones," J. Chem. Soc., Chem. Commun., 1984, 155–156.
Curci et al., "Enantioselective Epoxidation of Unfunctionalized Alkenes using Dioxiranes Generated In Situ," Tet. Lett., 1995, 36, 5831–5834.
Brown et al., "Epoxidation with Dioxiranes derived from 2–Fluoro–2–substituted–1–tetralones and –1–indanones," Tetrahedron, 1995, 51, 3587–3606.
Denmark et al., "Catalytic Epoxidation of Alkenes with Oxone. 2. Fluoro Ketones," J. Org. Chem., 1997, 62, 8288–8289.
Yang et al., "A $C_2$ Symmetric Chiral Ketone for Catalytic Asymmetric Epoxidation of Unfunctionalized Olefins," J. Am. Chem. Soc., 1996, 118, 491–492.
Yang et al., "Highly Enantioselective Epoxidation of trans–Stilbenes Catalyzed by Chiral Ketones," J. Am. Chem. Soc., 1996, 118, 11311–11312.
Armstrong and Hayter, "Concise synthesis of (4S, 5S)–4, 5–(isopropylidenedioxy)–2–cyclopentenone and a novel $C_2$–symmetric ketone," Tetrahedron: Asymmetry, 1997, 8, 1677–1684.
Song et al., "New $C_2$–symmetric chiral ketones for catalytic asymmetric epoxidation of unfunctionalized olefins," Tetrahedron: Asymmetry, 1997, 8, 2921–2926.
Aggarwal and Wang, "Catalytic asymmetric synthesis of epoxides mediated by chiral iminium salts," Chem. Commun., 1996, 191–192.
Davis and Chattopadhyay, "Asymmetric Epoxidation of Nonfunctionalized Alkenes with High Enantioselectivity using Chiral Sulfamyloxaziridines," Tet. Lett., 1986, 27, 5079–5082.
Ebrahim and Wills, "Synthetic applications of polymeric α–amino acids," Tetrahedron: Asymmetry, 1997, 8, 3163–3173.
Kroutil et al., "Development of the Julia asymmetric epoxidation reaction. Part 2. Application of the oxidation to alkyl enones, enediones and unsaturated keto esters," J. Chem. Soc., Perkin Trans. I, 1996, 2837–2844.
Kroutil et al., "Unexpected asymmetric epoxidation reactions catalysed by polyleucine–based systems," Chem. Commun., 1996, 845–846.
Itsuno et al., "Polymer–Supported Poly(amino acids) as New Asymmetric Epoxidation Catalyst of α,β–Unsaturated Ketones," J. Org. Chem., 1990, 55, 6047–6049.
Tipson et al., "Cyclic Acetals of Ketoses", Carbohyd.Res., 1971, vol. 16, pp. 383–393.
Du Penhoat et al., "Nucleophilic Addition–Reactions of 1,2:4,5–di–O–isopropylidene–β–D–erythro–2,3–hexo-diulo–2,6–pyranose, and the Stereo–Chemistry of the Products", Carbohyd. Res., 1979, vol. 71, pp. 135–148.
Chughtai et al., "Synthesis and Applications of Pseudo–C2 and C2–Chiral Cyclic Ketones", Abstract, 1996, 212th ACS National Meetings, American Chemical Society.

* cited by examiner

Primary Examiner—Ba K. Trinh

(57) ABSTRACT

A compound and method for producing an enantiomerically enriched epoxide from an olefin using a chiral ketone and an oxidizing agent is disclosed.

71 Claims, 8 Drawing Sheets

| Entry | $R_{12}, R_{13}$ | $R_{14}, R_{15}$ | $R_{16}$ | Olefin | %Conv. | %ee |
|---|---|---|---|---|---|---|
| 1 | Me, Me | Me, Me | H | β-methylstyrene | 96 | 92 |
| 2 | Me, Me | Et, Et | H | " | 91 | 91 |
| 3 | Me, Me | Et, H | H | " | 79 | 91 |
| 4 | Me, Me | Ph, H | H | " | 59 | 91 |
| 5 | Me, Me | i-Pr, H | H | " | 64 | 88.5 |
| 6 | Me, Me | -(CH$_2$)$_4$- | H | " | 95 | 92 |
| 7 | Me, Me | -(CH$_2$)$_5$- | H | " | 95 | 89 |
| 8 | Me, Me | Bn, Bn | H | " | 17 | 66 |
| 9 | Et, Et | Et, Et | H | " | 32 | 87 |
| 10 | Et, Et | Me, Me | H | " | 89 | 90 |
| 11 | -(CH$_2$)$_4$- | -(CH$_2$)$_4$- | H | " | 89 | 94 |
| 12 | -(CH$_2$)$_4$- | Me, Me | H | " | 100 | 93 |
| 13 | -(CH$_2$)$_4$- | -(CH$_2$)$_5$- | H | " | 51 | 87 |
| 14 | -(CH$_2$)$_4$- | Me, Me | H | " | 95 | 91 |
| 15 | -(CH$_2$)$_4$- | -(CH$_2$)$_6$- | H | " | 37 | 91 |
| 16 | Me, Me | Me, Me | CH$_2$OH | " | 16 | 12.5 |

| Entry | Ketone (eq.) | Olefin | Conversion (%) | ee (%) |
|---|---|---|---|---|
| 1 | (1.0) | β-methylstyrene | 3.4 | 24.5 |
| 2 | (0.5) | " | 100 | 36 |
| 3 | (1.0) | " | 41.3 | 62.2 |
| 4 | (0.3) | " | 18 | 4i |

| Entry | Ketone (eq.) | | Olefin | Conversion (%) | ee (%) |
|---|---|---|---|---|---|
| 1 |  | (0.5) | β-methylstyrene | 60 | 58 |
| 2 |  | (0.5) | " | 80 | 85 |
| 3 |  | (0.1) | " | 59 | 72.5 |
| 4 |  | (0.1) | " | 50 | 71.4 |
| 5 |  | (0.1) | Styrene | 90 | 66.5 |
| 6 |  | (0.05) | " | 96 | 64.6 |
| 7 |  | (0.05) | " | 99 | 64.8 |
| 8 |  | (0.05) | " | 70 | 67.0 |
| 9 |  | (0.1) | " | 100 | 65.9 |

| Entry | $R_{14}$, $R_{15}$ | Olefin | %Conv. | %ee |
|---|---|---|---|---|
| 1 | Me, Me | β-methylstyrene | 44 | 61 |
| 2 | Et, Et | " | 33 | 61 |
| 3 | Pr, Pr | " | 28 | 82 |
| 4 | Ph, Ph | " | 25 | 48 |
| 5 | Bn, Bn | " | 19 | 61 |
| 6 | -(CH$_2$)$_5$- | " | 52 | 52 |
| 7 | -(CH$_2$)$_4$- | " | 36 | 61 |

| Entry | $R_{17}$ | $R_{18}$ | $R_{14}$ | $R_{15}$ | $R_{16}$ | Olefin | %Conv. | %ee |
|---|---|---|---|---|---|---|---|---|
| 1 | MeO | H | Me | Me | H | β-methylstyrene | 15 | 59 |
| 2 | MeO | H | Me | Me | CH$_2$OTs | " | 30 | 43 |
| 3 | ClCH$_2$CH$_2$O | H | Me | Me | H | " | 16 | 67 |
| 4 | ClCH$_2$CH$_2$O | CH$_2$OH | Me | Me | H | " | 8 | 65 |
| 5 | ClCH$_2$CH$_2$O | CH$_2$OAc | Me | Me | H | " | 5 | 66 |
| 6 | ClCH$_2$CH$_2$O | CH$_2$OTBS | Me | Me | H | " | 10 | 40 |

| Catalyst | Ph⏜Ph | | | | | | | Ph⏜ | | |
|---|---|---|---|---|---|---|---|---|---|---|
| | Cat (mol%) | Yield (%) | ee (%) | | Cat (mol%) | Conv. (%) | ee (%) | | Cat (mol%) | Conv. (%) | ee (%) |

| Catalyst | Cat (mol%) | Yield (%) | ee (%) | Cat (mol%) | Conv. (%) | ee (%) | Cat (mol%) | Conv. (%) | ee (%) |
|---|---|---|---|---|---|---|---|---|---|
| 6a | 10 | 66 | 94.7 | 10 | 56 | 66.3 | 10 | 90 | 66.5 |
| 6b | 10 | 95 | 90.3 | 10 | 82 | 67.8 | 5 | 96 | 64.6 |
| 6c | 10 | 91 | 89.6 | 10 | 67 | 71.4 | 5 | 99 | 64.8 |
| 6d | 10 | 74 | 90 | 10 | 62 | 70.6 | 5 | 70 | 67.0 |
| 6e | 10 | 77 | 89.5 | 10 | 70 | 73.2 | 10 | 100 | 65.9 |

6a $R_{19}$ = $CO_2Me$
6b $R_{19}$ = Ac
6c $R_{19}$ = Bz
6d $R_{19}$ = Ts
6e $R_{19}$ = OTBS

| Entry | Substrate | Cat.(mol%) | T(°C) | time(h) | Yield(%) | ee(%) | Config. |
|---|---|---|---|---|---|---|---|
| 1 |  | 10 | -10 | 6 | 95 | 90.3 | (+)-(R,R) |
| 2 |  | 10 | 0 | 8 | 34 | 85.9 | (+)-(2S,3R) |
| 3 |  | 10 | 0 | 6 | 80 | 93.8 | (+)-(2S,3R) |
| 4 |  | 5 | -15 | 4 | 92 | 75.3 | (+)-(R,R) |
| 5 |  | 10 | 0 | 5 | 94 | 76.7 | (+)-(2S,3R) |
| 6 |  | 10 | 0 | 5 | 86 | 87.3 | (-)-(R) |
| 7 |  | 5 | -10 | 4 | 90 | 64.5 | (-)-(R) |
| 8 |  | 5 | -10 | 4 | 54 | 64.8 | (-) |
| 9 |  | 5 | -10 | 4 | 83 | 66 | (-) |
| 10 |  | 5 | -10 | 4 | 89 | 54 | (-)-(R) |
| 11 |  | 5 | -10 | 3 | 92 | 52.1 | (+)-(R) |
| 12 |  | 10 | -10 | 6 | 78 | 67.8 | (+)-(R,R) |

CATALYTIC ASYMMETRIC EPOXIDATION

This application is a 371 of PCT/US97/18310 filed Oct. 8, 1997 which claims the priority benefit of Provisional application No. 60/028,009 filed Oct. 8, 1996.

FIELD OF THE INVENTION

The present invention is directed to a catalytic asymmetric epoxidation of olefins by contacting an oxidizing agent to a mixture of a cyclic chiral ketone and an olefin.

BACKGROUND OF THE INVENTION

Epoxides are very important chiral building blocks for the synthesis of enantiomerically pure complex molecules. Asymmetric epoxidation of olefins presents a powerful strategy for the synthesis of enantiomerically enriched epoxides. Great success has been achieved in the epoxidation of allylic alcohols, unfunctionalized cis-olefins, and conjugated trisubstituted olefins. However, the epoxidation of trans-olefins bearing no allylic alcohol group with high enantiomeric excess still remains a challenging problem.

Among many other powerful epoxidation methods chiral dioxiranes generated in situ from Oxone® (potassium peroxomonosulfate) and a chiral ketone have appeared to be promising reagents for asymmetric epoxidations, particularly for trans-olefins bearing no allylic alcohol groups. Since the first asymmetric epoxidation of olefins with dioxirane were reported in 1984, significant progress has been made in the area. A $C_2$ symmetric cyclic chiral ketone derived from 1,1'-binaphthyl-2,2'-dicarboxylic acid has been used as a catalyst to achieve high enantioselectivity for the epoxidation of trans-4,4'-disubstituted stilbenes. This cyclic chiral ketone, however, is expensive and not readily available. In addition, the utility of this cyclic chiral ketone is limited to certain substrates.

Therefore, there is a need for an inexpensive, readily available, and general asymmetric epoxidation catalyst which can epoxidize a variety of olefins with high enantioselectivity.

SUMMARY OF THE INVENTION

Present invention provides a chiral ketone and a method of producing an epoxide from an olefin. The method includes adding a solution comprising an oxidizing agent to a reaction solution comprising a chiral ketone and an olefin under conditions effective to generate an epoxide; and separating the epoxide from the reaction solution. The chiral ketone is selected from the group consisting of compounds of the formula:

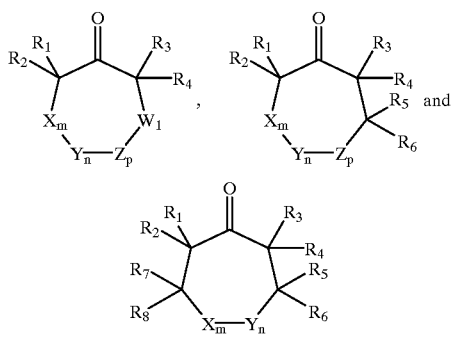

wherein

W, X, Y and Z are independently $CR_9R_{10}$, O, $NR_{11}$, S, Se, Si or P;

l, m, n and p are independently an integer from 0 to 3;

$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxylate, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms; and $R_{11}$ is hydrogen, oxygen or alkyl, sulfonyl, alkoxy or carbonyl groups containing from 1 to about 20 carbon atoms.

Preferably a chiral ketone is selected from the group consisting of the compound of the formula:

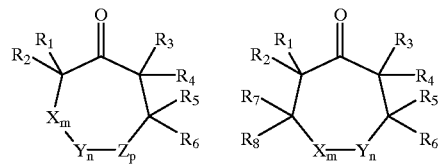

wherein preferably, m is 0, Y is O or $CR_9R_{10}$, n and p are 1, and Z is $CR_9R_{10}$.

Preferably two or more $R_1$, $R_2$, $R_3$, $R_4$, $R_5$, $R_6$, $R_7$, $R_8$, $R_9$ and $R_{10}$, are linked to form 3 to about 10 membered cyclic moiety containing 1 to about 20 carbon atoms, more preferably $R_1$ and $R_2$ are linked to form a moiety of the formula:

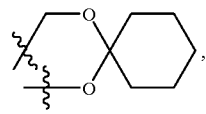

—O—C(CH$_2$CH$_3$)$_2$—O—CH$_2$— or —O—C(CH$_3$)$_2$—O—CH$_2$—.

Alternatively, $R_1$ and $R_7$ are linked to form a moiety of the formula —O—C(CH$_3$)$_2$—O—, —O—C(CH$_2$CH$_3$)$_2$—O—, or —C(CH$_3$)$_2$—.

Preferably $R_3$ and $R_6$ are linked to form a moiety of the formula —O—C(CH$_3$)$_2$—O— or a moiety of the formula —O—C(CH$_2$CH$_3$)$_2$—O—. Preferably $R_4$, $R_5$, $R_9$ and $R_{10}$ are independently hydrogen, halide or alkoxy, carboxyl or alkyl groups having 1 to about 20 carbon atoms. More preferably, $R_4$, $R_5$ and $R_{10}$ are hydrogen and $R_9$ is hydrogen, halide, or alkoxy, carboxyl, sulfinyl or alkyl groups having 1 to about 20 carbon atoms.

Preferably the ketone is derived from a carbohydrate, quinic acid or carvone. More preferably the ketone is derived from a group consisting of carvone, inositol, quinic acid, (D)-fructose, (L)-fructose, (D)-arabinose, (L)-arabinose and (L)-sorbose.

Preferably the epoxidation reaction is affected by adding an oxidizing agent selected from the group consisting of peracids, hydrogen peroxide, sodium hypochlorite, potassium peroxomonosulfate, sodium perborate and hypofluoride (HOF). Preferably the epoxidation reaction is affected at pH of from about 5 to about 14 by adding a base, more preferably at pH of from 10 to about 14, and most preferably at pH of from 10 to about 12.

In another embodiment of the present invention, a method of producing an epoxide from an olefin by contacting with a chiral dioxirane is provided. The chiral dioxirane is produced by contacting the corresponding chiral ketone with an oxidizing agent.

The present invention further includes

DETAILED DESCRIPTION OF THE INVENTION

Figure 1:
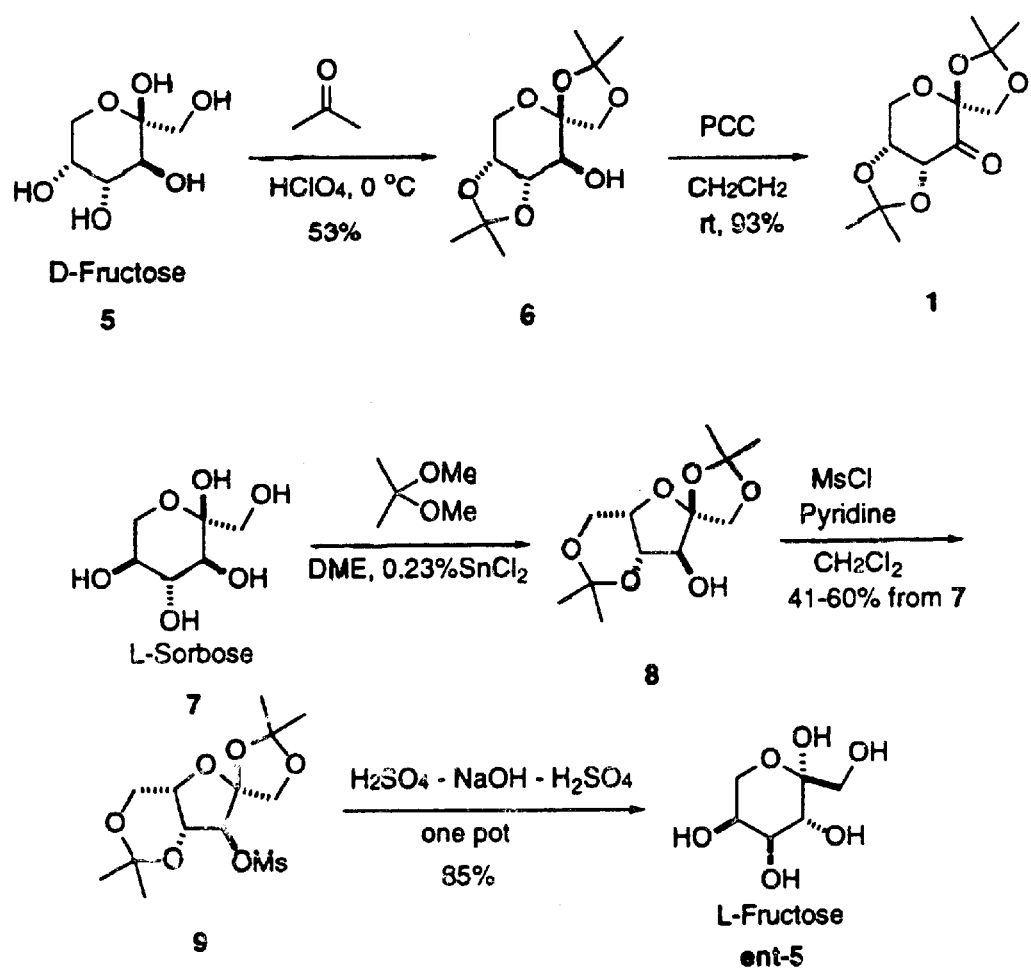
FIG. 1 illustrates a synthetic scheme for a preparation of a ketone derived from D-fructose which is a useful catalyst for the asymmetric epoxidation of olefins as described in the present invention and a synthetic scheme for a preparation of L-fructose from L-sorbose.

Epoxides are used in many industrial processes as chiral building blocks for the synthesis of enantiomerically pure complex molecules such as polymers, surfactants, pesticides, insecticides, insect hormones, insect repellants, pheromones, food flavoring, and drugs. The stereochemistry of a molecule is important in many of the properties of the molecule. For example, it is well known that physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer. Thus, it is advantageous to be able to control the stereochemistry of a chemical reaction. Since an epoxide serve as an intermediate or a starting material for many chemical compounds, it is especially desirable to be able to control the stereochemistry of the epoxide formation.

Selectivity and reactivity are two important factors that need to be considered in searching for the effective ketone catalyst. Ketones containing the following general features are particularly desirable: (1) having the stereogenic centers close to the reacting center, resulting in efficient stereochemical communication between substrates (i.e., the olefins) and the catalyst; (2) having the presence of fused ring(s) or a quaternary center (i.e, fully substituted carbon atom) a to the carbonyl group to minimize the epimerization of the stereogenic centers; (3) controlling possible competing approaches of an olefin to the reacting dioxirane by sterically blocking one face or using a $C_2$ or pseudo $C_2$ symmetric element. As used in this invention, a "face" means a plane or a direction in which the olefin approaches the dioxirane. Dioxirane is any compound having a three-membered cyclic ring system comprising two oxygen atoms and one carbon atom.

The present invention provides a method for asymmetrically epoxidizing olefins using a chiral ketone and an oxidizing agent. A chiral center (i.e., stereochemical center, or stereogenic center) is, of course, an atom to which four different groups are attached; however, the ultimate criterion of a chiral center is nonsuperimposability on the mirror image. Facially selective, stereoselective, enantioselective or asymmetric synthetic reactions are those in which one of a set of stereoisomers is formed exclusively or predominantly.

In one embodiment of the present invention, a method for asymmetrically epoxidizing an olefin comprises a step of adding an oxidizing agent to a solution comprising an olefin and a chiral ketone under conditions effective to generate an epoxide and separating the epoxide from the solution. Preferably, one isomer is produced in at least about 50 percent excess over the other isomer. More preferably, one isomer is produced in at least about 80 percent excess over the other isomer. Still more preferably, one isomer is produced in at least about 90 percent excess over the other isomer. Even more preferably, one isomer is produced in at least about 95 percent excess over the other isomer. As used in this invention, an "olefin" refers to a compound having an alkene functionality, i.e., a double bond between two carbon atoms. An olefin can have more than one double bond. If more than one double bond is present on the olefin, the double bonds can be conjugated or non-conjugated. The olefin can be monosubstituted, di-substituted, tri-substituted or fully substituted. By substituted, it is meant that the olefinic carbon atom is attached to an atom other than hydrogen atom. For example, the olefinic carbon can be substituted with a halogen atom, silicon atom, another carbon atom, oxygen atom, sulfur atom and/or a metal atom such as lithium, sodium or magnesium. Preferably, the olefin is at least a di-substituted olefin. The di-substituted olefin can be geminal, cis-, or trans-substituted olefin. Preferably the di-substituted olefin is a trans-substituted olefin. Generally for olefins having at least three substituent groups, trans-olefin designation refers to the trans relationship between the larger substituents attached to the two different olefinic carbon atoms, whereas cis designation refers to the cis relation between the larger substituents. In addition to cis- and trans-notation an "E" or "Z" notation can used to denote the relative priority of the substituent groups. E- and Z-notations denoting the stereoisomers of alkenes are well known to one of ordinary skill in the art. Preferably, the olefin is E-stereoisomer (i.e., trans-olefin).

Without being bound by a theory, it is believed that contacting an oxidizing agent to a chiral ketone produces a chiral dioxirane. Although the chiral dioxirane can be isolated under certain conditions, in general it is generated and used in situ by contacting (i.e, reacting) a chiral ketone with an oxidizing agent. Without being bound by a theory, it is believed that the reaction between an olefin and the dioxirane provides an epoxide and regenerates the ketone; therefore, the ketone can be used as a catalyst. In addition, less than one equivalent of the ketone with respect to the olefin can be used in the present invention. The same molecule of ketone can be used more than once in epoxidizing an olefin. The average number of epoxidation of olefins produced by a ketone molecule is known as a catalytic turn-over rate, or simply a turn-over rate. Preferably the ketones of the present invention have a turn-over rate of at least about 3, more preferably at least about 50 and most preferably at least about 100. Moreover, since the ketones have such a high turn-over rate, the amount of the ketones required to epoxidize a given amount of olefin can be less than the stoichiometric amount, i.e., one equivalent, of the olefin. Preferably no more than about 0.3 equivalents of ketone is used to epoxidize olefins, more preferably no more than about 0.05 equivalents, and most preferably no more than about 0.01 equivalents.

The ketones for the present invention are preferably a cyclic chiral ketone having at least 3 carbon atoms in the cyclic system, more preferably at least about 4 carbon atoms, and most preferably at least about 5 carbon atoms. Cyclic compounds (or moieties) refer to compounds (or moieties) having a chain of atoms that does not have a terminal portion, i.e, a ring of atoms. The atoms in a cyclic compound (or moiety) can be all carbon atoms, or it can be a chain of carbon atoms which can be interrupted by an oxygen atom, sulfur atom, nitrogen atom, silicon atom, phosphorus atom, and/or any other multi-valent atoms. Although a $C_2$-symmetry can be present in the cyclic chiral ketone, unlike Yang's procedure, supra, a presence of a $C_2$-symmetry on the cyclic chiral ketone is not required for the present invention.

In one embodiment of the present invention, the ketone is selected From the group consisting of compounds of the formula:

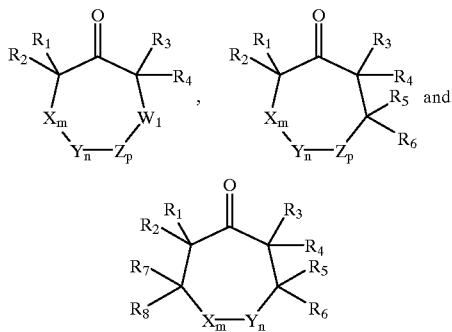

wherein
W, X, Y and Z are independently $CR_9R_{10}$, O, $NR_{11}$, S, Se, Si or P;
l, m, n and p are independently an integer from 0 to 3;
$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms; and
$R_{11}$ is hydrogen, oxygen or alkyl, sulfonyl, alkoxy or carbonyl groups containing from 1 to about 20 carbon atoms. Alternatively, two or more $R_1$, $R_2$, $R_3$, $R_4$, $R_5$, $R_6$, $R_7$, $R_8$, $R_9$ and $R_{10}$ are joined (i.e., linked) to form 3 to about 10 membered cyclic moiety containing 1 to about 20 carbon atoms. For example, $R_3$ and $R_5$ can be linked to form a moiety of the formula —O—C(CH$_3$)$_2$—O—, or $R_3$ and $R_4$ can be linked to form a moiety of the formula —O—C(CH$_2$CH$_3$)$_2$—O—(CH$_2$)—. More preferably $R_1$, $R_2$, $R_3$, $R_4$, $R_5$, $R_6$, $R_7$, $R_8$, $R_9$ and $R_{10}$ are independently hydrogen, halide, or alkoxy, siloxy, carboxyl, or sulfonyl groups having 1 to about 20 carbon atoms, or two or more $R_1$, $R_2$, $R_3$, $R_4$, $R_5$, $R_6$, $R_7$, $R_8$, $R_9$ and $R_{10}$ are linked to form a from about three to about six-membered cyclic moiety. Without being bound by any theory, it is believed that the reactive species in the epoxidation of the olefin is the corresponding dioxiranes of the formula:

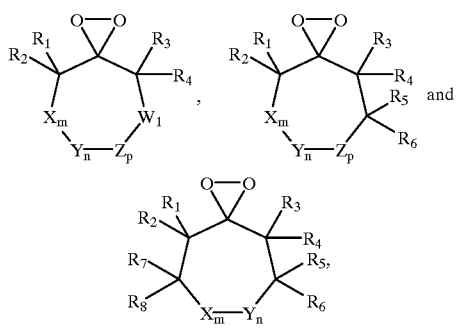

respectively.

A chiral cyclic ketone can be derived from any appropriate starting material such as a carbohydrate, carvone, inositol, and quinic acid. In another embodiment of the present invention, a carbohydrate-derived chiral ketone is used as an epoxidation catalysts. Reasons for selecting these ketones as catalysts include (a) carbohydrates are chiral and readily available; (b) they are highly substituted with oxygen groups, which would be good for reactivity, as the inductive effect of oxygen activates the ketone catalyst; and (c) carbohydrate-derived ketones could have rigid conformations because of the anomeric effect, which would be desirable for selectivity. Preferably, the cyclic ketone is derived from an oxidation of an unprotected hydroxy group of a carbohydrate compound having at least one protected hydroxy group. As used in the present invention, carbohydrate is a sugar molecule or its derivative. Carbohydrate can be monosaccharide or polysaccharide. Exemplary carbohydrates include glucose, fructose, maltose, lactose, mannose, sorbose, ribose, xylose, rhamnose, galactose, talose, arabinose, gulose, sucrose, cellobiose, cellulose, maltonic acid, heparin, chondroitin sulfate, amylose and amylopectin. Preferably the protecting groups for protected hydroxy groups are selected from the group consisting of silyl ethers, ethers, acetals, ketals, esters, ortho esters, sulfonates, phosphates and mixtures thereof. The protecting groups for two or more hydroxy groups of the carbohydrate or its derivative can be interconnected. For example, an acetonide group protecting 4,5-hydroxy groups of fructose can be considered to be "two interconnected acetal protecting groups" since they protect two hydroxy groups on the fructose. The oxidation of a hydroxy group of a carbohydrate to form a carbonyl group is well known to one skilled in the art. See Mio et al. *Tetrahedron* 1991, 47, 2133–2144. For example, pyridinium chlorochromate (PCC), pyridinium dichromate (PDC), Swern oxidation condition or other oxidizing conditions can be used to oxidize a hydroxy group of a carbohydrate or its derivative to a ketone compound of the present invention. Preferably, the carbohydrate is selected from the group consisting of fructose, sorbose arabinose, mannose and glucose. More preferably, the carbohydrate is selected from the group consisting of (D)-fructose, (L)-fructose (L)-sorbose, (L)-arabinose and (D)-arabinose.

Preferably, the cyclic ketone is selected from the group consisting of a compound of the formula:

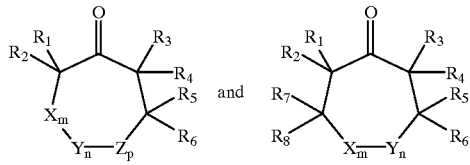

Preferably, m is 0, Y and Z are independently O or $CR_9R_{10}$, and n and p are 1. Preferably, two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms. Preferably, $R_1$ is linked with $R_2$ or $R_7$ to form a three, five or six-membered cyclic moiety. When $R_1$ and $R_2$ are linked, preferably the linkage forms a moiety of the formula

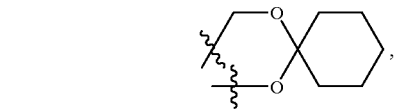

$—O—C(CH_3)_2—O—CH_2—$, $—C(CH_3)_2—$, or $—O—C(CH_2CH_3)_2—O—CH_2—$.

When $R_1$ and $R_7$ are linked, preferably the linkage forms a moiety of the formula $—O—C(CH_3)_2—O—$ or $—O—C(CH_2CH_3)_2—O—CH_2—$. Preferably, $R_3$ and $R_6$ are linked to form a five-membered cyclic moiety, and most preferably $R_3$ and $R_6$ are linked to form a moiety of the formula $—O—C(CH_3)_2—O—$, $—C(CH_3)_2—$ or $—O—C(CH_2CH_3)_2—O—CH_2—$. Preferably $R_4$, $R_5$, $R_9$ and $R_{10}$ are independently hydrogen, or alkoxy, carboxyl, sulfonyl or alkyl groups having 1 to about 20 carbon atoms. When both Y and Z are $CR_9R_{10}$, preferably one $R_9$ is hydrogen and the other $R_9$ is hydrogen, halide, alkyl or alkoxy group containing 1 to about 20 carbon atoms, more preferably 1 to about 10 carbon atoms, and most preferably 1 to about 6 carbon atoms.

As used in this invention, a moiety of the formula does not include atoms which are directly part of the parent cyclic ketone structure. Thus, for example, a compound of the formula

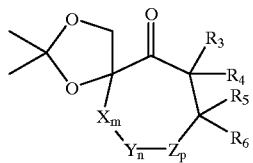

can be alternatively be described as a compound of the formula

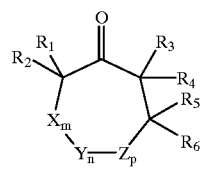

with $R_1$ and $R_2$ being linked to form a moiety of the formula $—O—C(CH_3)_2—O—(CH_2)—$.

Alkyl groups according to the present invention are aliphatic hydrocarbons which can be straight or branched carbon atom chain groups. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, n-pentyl, heptyl, octyl, hydroxymethyl, hydroxy ethyl, chloromethyl, aminomethyl and dimethylaminomethyl.

Although the dioxirane can be generated in a separate reaction mixture prior to contacting with an olefin, it is more advantageous to combine the ketone and the olefin in a single reaction mixture and generate the dioxirane in situ by adding a solution comprising an oxidizing agent or a solid comprising an oxidizing agent to the solution comprising the ketone and the olefin. In this manner, the ketone can be used in an amount less than the stoichiometric amount relative to the amount of the olefin. It should be appreciated that in situ generation of dioxirane from a ketone generally requires the oxidizing agent to be more reactive towards the ketone than the olefin to avoid competing oxidation of olefin by the oxidizing agent. However, when the reactivity of the oxidizing agent with the olefin is similar or greater than with the ketone then one method of providing a higher amount of reaction between the oxidizing agent and the ketone to generate the dioxirane is to use the ketone in an amount substantially more than the amount of the olefin. In these cases, preferably the amount of ketone used is at least about 3 times more than the amount olefin, more preferably at least about 5 times, and most preferably at least about 10 times.

Any oxidizing agent capable of providing dioxiranes from a corresponding ketone can be used in the present invention. However, for economic reasons a relatively inexpensive oxidizing agents such as peracids, hydrogen peroxide, sodium hypochlorite, potassium peroxomonosulfate, sodium perborate and hypofluoride (HOF) are preferred. Non-organic oxidizing agents (i.e, a compound that does not contain any carbon atom) are particularly preferred as these oxidizing agents and their reaction products can be easily removed from the reaction mixture by a simple aqueous extraction. Preferably, the oxidizing agent is potassium peroxomonosulfate. The amount of oxidizing agent used in the present invention depends on a variety of factors including the reactivity of the ketone, olefin, and the decomposition rate of the oxidizing agent. Preferably the amount of an oxidizing agent used is at least about 1 times the amount of the ketone, more preferably at least about 9 times, and most preferably at least about 100 times. In another embodiment of the present invention, the amount of an oxidizing agent used is less than about 10 times the amount of the olefin, more preferably less than about 3 times, and most preferably less than about 1 times.

As shown on Table 1, the reaction time affects both the yield of the epoxide as well as the enantiomeric excess of the epoxide produce. Thus, while a longer reaction period provides higher yield of the epoxide, the enantiomeric excess begins decrease after awhile. Therefore, obtaining a maximum yield of the epoxide while maintaining a sufficient level of enantiomeric excess requires a compromise between the two diametrically opposed results. Preferably, the reaction time is from about 0.1 h to about 24 h, more preferably from about 0.1 h to about 8 h, and most preferably from about 0.1 h to about 3 h.

TABLE 1

Asymmetric Epoxidation of trans-Stilbene via Ketone 1[a]

| Entry | Time (h) | Isolated Yield (%) | ee (%)[b] |
|---|---|---|---|
| 1[c] | 1 | 31 | >95 |
| 2[d] | 2 | 39 | >95 |
| 3[e] | 4 | 40 | 89 |
| 4[f] | 8 | 47 | 85 |

[a]The reactions were carried out at 0° C. (bath temperature) with substrate (1 eq.), ketone 1 (1 eq.), Oxone (5 eq.), and NaHCO$_3$ (15.5 eq.) in CH$_3$CN - aqueous EDTA (4 × 10$^{-4}$M) (1.5:1, V/V) as in Method A.
[b]Enantioselectivity was determined by $^1$H NMR shift analysis of stilbene oxide with Eu(hfc)$_3$.
[c]The Oxone/NAHCO$_3$, mixture added in 45 min, and the reaction worked up after 1 hr.
[d]The Oxone/NaHCO$_3$ mixture added in 100 min, and the reaction worked up after 2 h.
[e]The Oxone/NaHCO$_3$ mixture added in 220 min, and the reaction worked up after 4 h.
[f]The Oxone/NaHCO$_3$, mixture added in 6 h, and the reaction worked up after 8 h.

Figure 2:
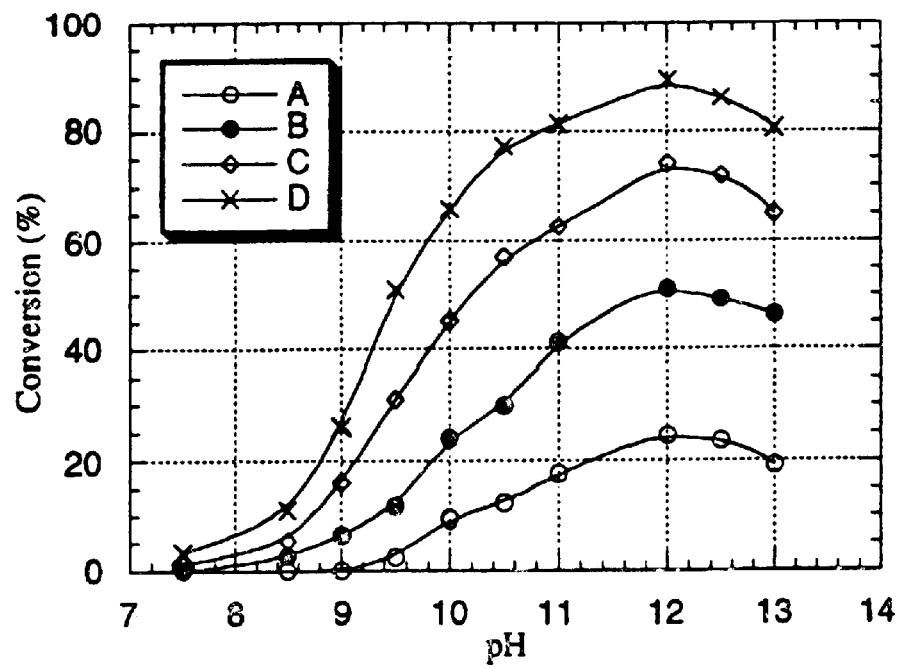
FIG. 2 is a plot of % conversion of trans-β-methylstyrene against pH of the epoxidation reaction using 20 mol % of ketone 1 at 0° C. at 1.5 h reaction time.

The pH is also an important factor for the epoxidation with dioxiranes generated in situ. In some cases, generally higher pH results in more rapid autodecomposition of the dioxirane and/or the oxidizing agent, which leads to the decrease in epoxidation efficiency. For this reason, most non-asymmetric epoxidations are usually carried out at pH 7–8. In some cases, the optimal pH is within a narrow window of 7.8–8.0. As shown in FIG. 2, some epoxidations are more effective at a higher pH. Lines A, B, C and D in FIG. 2 represent samples taken at a reaction time of 0.5 h, 1.0 h, 1.5 h and 2.0 h, respectively. In all cases, the optimal pH is about 12 for epoxidation of methylstyrene with acetone as a catalyst.

For the asymmetric epoxidation, another issue that needs to be considered is the side reaction. As used in this invention, a "side reaction" is a reaction that does not ultimately lead to a production of a desired product (a desired product of the reaction between an oxidizing agent and a ketone is a dioxirane, whereas the desired product of the reaction between a dioxirane and an olefin is an epoxide). Without being bound by a theory, it appears that the Baeyer-Villiger reaction is one of the major side reactions for the catalyst at pH 7–8. The competing Baeyer-Villiger reaction can be reduced at a higher pH which can lead to a more efficient formation of dioxirane 12.

Figure 3:
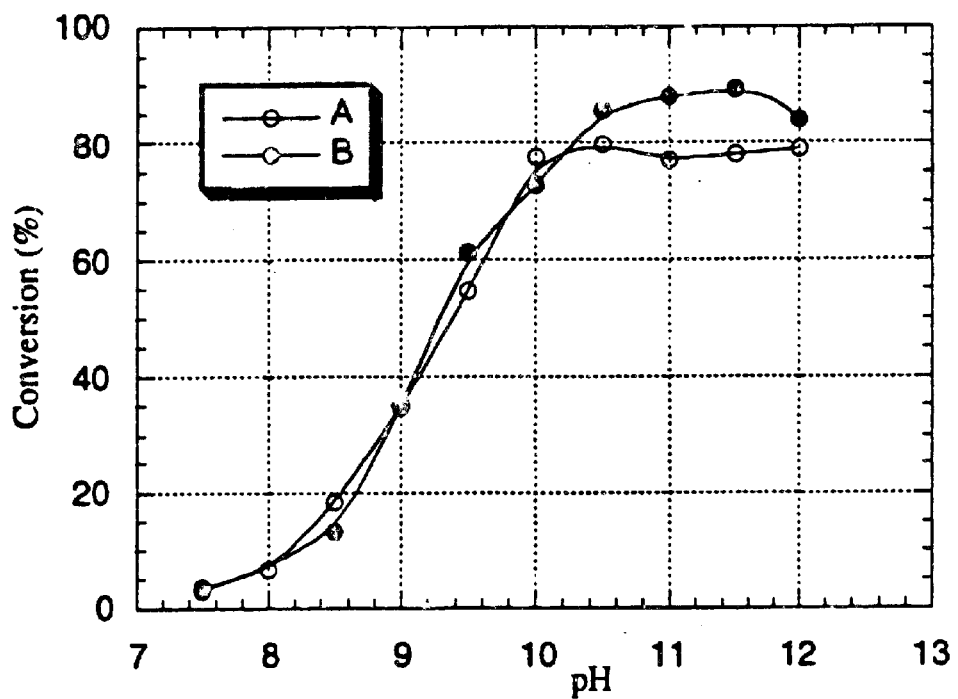
FIG. 3 is a plot of % conversion of trans-β-methylstyrene against pH of the epoxidation reaction using 3 equivalents of acetone as the catalyst in $H_2O$—$CH_3CN$ (1:1.5, V/V) solvent system at different time intervals.
Figure 4:
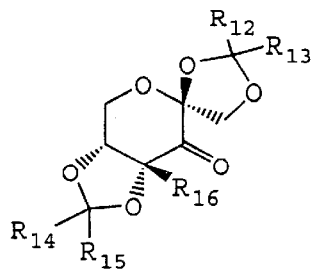
FIG. 4 illustrates reactivities of a variety of fructose derived chiral ketones at 0° C. using 0.3 or 0.5 equivalents of the chiral ketone.
Figures 5, 6:
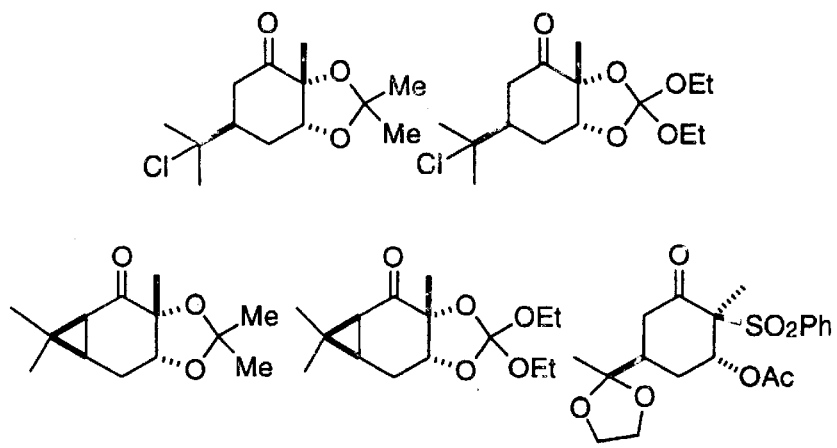
FIG. 5 shows results of asymmetric epoxidation of olefins at 0° C. using catalytic amounts of chiral ketones prepared from glucose, sorbose and mannose.
FIG. 6 shows some of the chiral ketones of the present invention which are derived from carvone.
Figure 7:
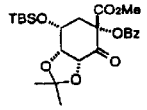
FIG. 7 shows some of the chiral ketones of the present invention which are derived from quinic acid and some of the results of epoxidation of olefins using them.
Figure 7:
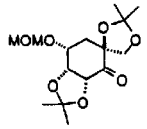
Figure 7:
Figure 7:
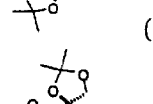
Figure 7:
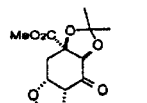
Figure 7:
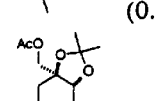
Figure 7:
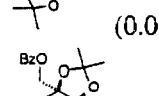
Figure 7:
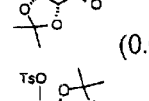
Figure 7:
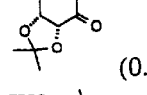
Figure 8:
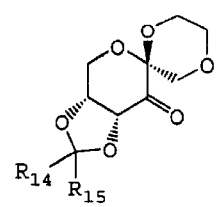
FIG. 8 shows some of the results of asymmetric epoxidation of olefins using a variety of chiral ketones derived from fructose having a fused and a spiro cyclic moiety attached to the parent ketone cyclic structure.
Figure 9:
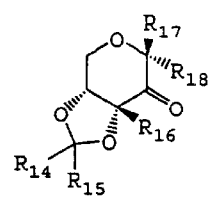
FIG. 9 shows some of the results of asymmetric epoxidation of olefins using a variety of chiral ketones derived from fructose having a fused cyclic moiety to the parent ketone cyclic structure.
Figure 10:
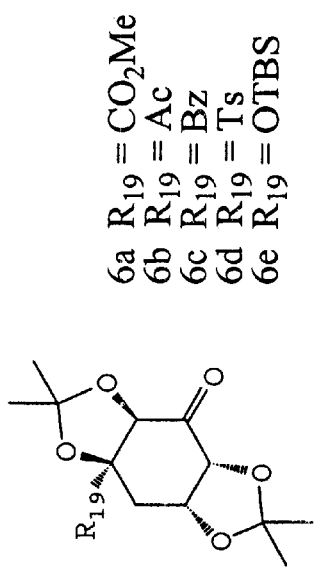
FIG. 10 shows some of the results of asymmetric epoxidation of olefins by a variety of chiral ketones derived from quinic acid.
Figure 11:
FIG. 11 shows some of the results of asymmetric epoxidation of a variety of olefins using chiral ketone 6b that is derived from quinic acid.
Figure 11:
Figure 11:
Figure 11:
Figure 11:
Figure 11:
Figure 11:
Figure 11:
Figure 11:
Figure 11:
Figure 11:
Figure 11:

In the present invention, it has been found that higher pH generally provides a higher conversion rate of the olefin to the epoxide (i.e, higher yield of epoxides from olefins) and higher catalytic efficiency (i.e., higher turn-over rate). As shown in FIG. 3, the pH has a profound effect on the amount of epoxide produced by the methods of the present invention. In FIG. 3, line A represents a reaction solvent system comprising 1:1.5, V/V, of H$_2$O—CH$_3$CN and line B represents a reaction solvent system comprising 2:1:2, V/V, of H$_2$O—CH$_3$CN-DMM. In certain cases, the production of epoxides from olefins increased more than 10 fold from a lower pH (7–8) to a higher pH (>10) while maintaining a high enantioselectivity (90–92% ee). In addition, the amount of oxidizing agent can be reduced significantly. The optimal pH range is broad, which increases the utility of the present invention to a wide variety of olefins. Preferably, the pH is at least about 5, more preferably at least about 8, still more preferably at least about 10. Even more preferably the pH is from about 5 to about 14, yet even more preferably from about 10 to about 14, and most preferably from about 10 to about 12. The pH of the reaction solution can be conveniently achieved by adding sufficient amount of base to maintain the pH at the desired level. The base can be added separately, it can be added to the solution containing the ketone, or it can be added to the solution containing the oxidizing agent. Alternatively, a solid mixture of the base and oxidizing agent can be added to the reaction mixture. Preferably the base is selected from the group consisting of hydroxides, carbonates, bicarbonates, borates and phosphates. More preferably the base is selected from the group consisting of potassium carbonate, potassium bicarbonate, lithium carbonate, lithium bicarbonate, sodium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide, most preferably the base is selected from the group consisting of potassium carbonate, potassium bicarbonate, sodium bicarbonate, sodium carbonate, sodium hydroxide, sodium borate, sodium phosphate, potassium phosphate and potassium hydroxide. Alternatively, the desire pH of the reaction can be more easily maintained by using a buffer solution.

Another factor which determines the yield of epoxide and/or enantioselectivity of the reaction is the solvent system used. Typically, any organic solvent can be used for the present invention. Exemplary solvents include, nitrites such as acetonitrile and propionitrile, dimethoxymethane (DMM), dimethoxyethane (DME), ethers such as tetrahydrofuran (THF) and diethyl ether (Et$_2$O), dichloromethane, chloroform, ethyl acetate, hexane, benzene, toluene, xylenes, dioxane, dimethyl formamide (DMF), pentane, alcohols including, but not limited to, methanol, ethanol and i-propyl alcohol, and mixtures thereof.

In another embodiment of the present invention, a mixture of organic solvent and aqueous solution is used as a reaction solution. As Table 2 shows, a wide variety of solvents can be used for the present invention. Percentage of enantiomeric excess (%ee), which is a measure of enantioselectivity, is equal to % of one enantiomer (e.g. stereoisomer)—% of the other enantiomer. Thus for example, if the reaction produces (R,R) and (S,S) epoxides in 99% and 1%, respectively, the enantiomeric excess percentage (%ee) will be 98%. Preferably, the methods of the present invention provides asymmetric epoxidation of olefins in at least about 50%ee, more preferably at least about 80%ee, and most preferably at least about 90%ee. In another embodiment of the present invention, the yield of the epoxide from asymmetric epoxidation of an olefin is at least about 10%, more preferably at least about 50%, and most preferably at least about 80%.

TABLE 2

The Solvent Effects on the Asymmetric Epoxidation

| Entry | Solvents | T(° C.)) | Time(min | Convers | % ee[c] |
|---|---|---|---|---|---|
| 1 | CH$_3$CN | 20 | 20 | 100 | 89 |
| 2 | CH$_3$CN | 0 | 90 | 96 | 92 |
| 3 | CH$_3$CH$_2$CN | 20 | 60 | 11 | 80 |
| 4 | DMM | 20 | 60 | 36.2 | 91 |
| 5 | DME | 20 | 20 | 100 | 89 |

TABLE 2-continued

The Solvent Effects on the Asymmetric Epoxidation

| Entry | Solvents | T(° C.)) | Time(min) | Convers | % ee[c] |
|---|---|---|---|---|---|
| 6 | DME | 0 | 90 | 92 | 89 |
| 7 | DMF | 20 | 20 | 95 | 86 |
| 8 | Dioxane | 20 | 20 | 100 | 86 |
| 9 | Dioxane | 0 | 90 | 96 | 86 |
| 10 | THF | 20 | 60 | 18 | 74 |
| 11 | $Et_2O$ | 20 | 60 | 0 | |
| 12 | $CH_2Cl_2$ | 20 | 30 | <3 | nd |
| 13 | $CH_3CN/DMM$ (2/1) | 20 | 20 | 100 | 90 |
| 14 | $CH_3CN/DMM$ (2/1) | 0 | 90 | 100 | 92 |
| 15 | $CH_3CN/DMM$ (1/1) | 20 | 20 | 98 | 91 |
| 16 | $CH_3CN/DMM$ (1/1) | 0 | 90 | 100 | 93 |
| 17 | $CH_3CN/DMM$ (½) | 20 | 20 | 94 | 92 |
| 1B | $CH_3CN/DMM$ (½) | 0 | 90 | 88 | 94 |
| 19 | $CH_3CN/DMM$ (1/4) | 0 | 90 | 77 | 94 |
| 20 | DMM/DME (1/1) | 20 | 25 | 66 | 92 |
| 21 | $CH_3CN/DMM/DME$ (1/ | 20 | 20 | 100 | 90 |
| 22 | $CH_3CN/DMM/DME$ | 20 | 20 | 89 | 90 |
| 23 | $CH_3CN/THF$ (1/1) | 20 | 25 | 63 | 82 |
| 24 | $CH_3CN/Et_2O$ (1/1) | 20 | 25 | 28 | 84 |
| 25 | $CH_3CN$ | 0 | 240 | 58.4 | 63.4 |
| 26 | DME | 0 | 240 | 100 | 69.6 |
| 27 | DME | −10 | 240 | 95 | 73.1 |
| 28 | DMM | 0 | 240 | 43 | 66.3 |
| 29 | Dioxane | 0 | 240 | 99.4 | 66.6 |
| 30 | $DMM/CH_3CN$ (2/1) | 0 | 240 | 91 | 67.1 |
| 31 | DMF | 0 | 180 | 99 | 64.3 |

[a]Reactions in entries 1–24 were carried out with trans-β-methylstyrene (1 mmol), ketone 1 (0.3 mmol), Oxone ® (1.38 mmol) in a mixture of 15 mL of organic solvent and 10 mL of 0.05M $Na_2B_4O_7 \cdot 10H_2O$ in aqueous EDTA (4 × $10^{-4}$M) solution, and the pH was adjusted to 10.5 by using 1.0M aqueous $K_2CO_3$ solution. Reactions in entries 25–31 were carried out with trans-β-methylstyrene (0.4 mmol), ketone DW-25a (see Experimental section) (0.02 mmol), Oxone ® (0.55 mmol), and $K_2CO_3$ (2.31 mmol) in organic solvent (6 mL) and buffer (0.05M $Na_2B_4O_7 \cdot 10H_2O$ in aqueous EDTA (4 × $10^{-4}$M) (4 mL).
[b]Conversion was determined by GC (HP-17 column).
[c]Enantioselectivity was determined by chiral GC (Chiraldex γ-TA column).

Preferably the solvent is selected from the group consisting of acetonitrile, DMM, DME, DMF, dioxane and mixtures thereof. In certain cases, a mixture of solvents provide higher yield and/or enantioselectivity, for example, a mixture of $CH_3CN$ and DMM is particularly useful.

As Table 2 and Table 3 shows, the temperature of the reaction also affects the yield of the reaction and enantioselectivity of the epoxide. Generally, a lower reaction temperature requires a longer reaction time but results in higher enantioselectivity.

TABLE 3

The Temperature Effect on the Epoxidation of trane-β-Methylstyrene by Ketone 1[a]

| Entry | T (° C.) | Conv. (%)[b] | ee (%)[c] |
|---|---|---|---|
| 1 | −11 | 99.4 | 95.7 |
| 2 | −6 | 96.9 | 95.4 |
| 3 | −2 | 97.5 | 95.2 |
| 4 | 2 | 99.4 | 94.7 |
| 5 | 8 | 99.0 | 93.8 |
| 6 | 20 | 99.0 | 93.2 |
| 7 | 30 | 96.8 | 91.1 |

[a]All reactions were carried out with trans-β-methylstyrene (1 mmol), ketone 1 (1 mmol), Oxone ® (1 mmol), $K_2CO_3$ (4.3 mmol), and $BU_4NHSO_4$ (0.05 mmol) in 25 mL of $CH_3CN$-DMM-0.05M $Na_2B_4O_7 \cdot 10H_2O$ in aqueous EDTA (4 × $10^{-4}$M) solution (1:2:2, V/V); the reactions were stopped after 20 min.
[b]Conversion was determined by GC (HP-17 column).
[c]Enantioselectivity was determined by chiral GC (Chiraldex γ-TA column).

Preferably the reaction temperature is less than about 100° C., more preferably less than about 30° C., and most preferably less than about 0° C.

As Table 4 shows the present invention is useful for providing an epoxide from a variety of olefins. High enantiomeric excess can be obtained especially with trans-substituted olefins.

TABLE 4

Asymmetric Epoxidation of Representative trans-disubstituted Olefins by Ketone 1 and ent-1.

| Entry | Substrate | Method[a] | T (° C.) | % Yield[c] | % ee | Config.[j] |
|---|---|---|---|---|---|---|
| 1 | Ph-CH=CH-Ph | A | 0 | 73 | 95.2[e] | (+)-(R,R) |
| | | B | 0 | 75 | 97[e] | (−)-(S,S) |
| | | C | 0 | 78 | 98.9[e] | |
| | | C | 20 | 85 | 97.9[e] | |
| | | C (ent-1) | 0 | 81 | 98.3[e] | |
| 2 | Ph-CH=CH-CH3 | A | 0 | 81 | 88[g] | (+)-(R,R) |
| | | B | 0 | 93 | 91.7[f] | (−)-(S,S) |
| | | C | −10 | 94 | 95.5[f] | |
| | | C (ent-1) | −10 | 94 | 95.7[f] | |
| 3 | Ph-CH=CH-CH2-OTBS | A | 0 | 74 | 93[g] | (+)-(R,R) |
| | | B | 0 | 87 | 94[g] | |
| | | C | 0 | 71 | 95.2[e] | |
| 4 | Ph-CH=CH-CH2-OCPh3 | C | 0 | 55 | 94.0[e] | (+)-(R,R)[K] |
| 5 | Ph-CH=CH-CH2-Cl | A | 0 | 61 | 93[g] | (+)-(2S,3R) |
| | | C | 0 | 49 | 96.2[f] | |

TABLE 4-continued

Asymmetric Epoxidation of Representative trans-disubstituted Olefins by Ketone 1 and ent-1.

| Entry | Substrate | Method[a] | T (° C.) | % Yield[c] | % ee | Config.[j] |
|---|---|---|---|---|---|---|
| 6 | 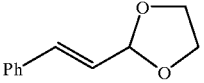 | A | 0 | 41 | 93[g] | (+)-(2S,3R)[K] |
| 7 | 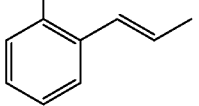 | C | −10 | 91[d] | 93.3[f] | (+)-(R,R) |
| 8 | 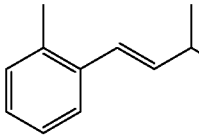 | C | −10 | 78[d] | 95.7[f] | (−)-(R,R)[K] |
| 9 | 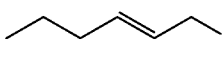 | A<br>C | 0<br>−10 | 80<br>83 | 93[h]<br>94.5[h] | (+)-(R,R) |
| 10 | 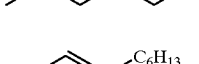 | A<br>C | 0<br>−10 | 84<br>85 | 87[h]<br>93[h] | (+)-(R,R) |
| 11 | 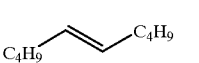 | A<br>B[b]<br>C | 0<br>0<br>−10 | 81<br>88<br>89 | 90[i]<br>93[i]<br>95[i] | (+)-(R,R) |
| 12 |  | B[b] | 0 | 70 | 91[i] | (+)-(R,R) |
| 13 |  | C | −10 | 92 | 92[g] | (+)-(R,R) |
| 14 | 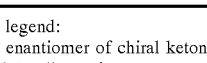 | B<br>C | 0<br>0 | 76<br>68 | 91[g]<br>92[g] | (+)-(R,R) |

Table 4 legend:
ent-1 is enantiomer of chiral ketone 1 shown in FIG. 1.
[a]Method A: all reactions were carried out at 0° C. (bath temperature) with substrate (1 eq.), ketone (3 eq.), Oxone (5 eq.), and NaHCO$_3$ (15.5 eq.) in CH$_3$CN - aqueous EDTA (4 × 10$^{-4}$ M) solution (1.5:1, V/V). The reactions were stopped after 2 h.
Method B: all reactions were carried out with substrate (1 eq.), ketone (0.3 eq.), Oxone (1.38 (eq.), and K$_2$CO$_3$ (5.8 eq.) in CH$_3$CN - 0.05 M Na$_2$B$_4$O$_7$·10H$_2$O of aqueous EDTA (4 × 10$^{-4}$ M) solution (1:2:2, V/V). The reactions were stopped after 1.5 h.
Method C: all reactions were carried out with substrate (1 eq.), ketone (0.3 eq.), Oxone (1.38 eq.), and K$_2$CO$_3$ (5.8 eq.) in CH$_3$CN-DMM - 0.05 M Na$_2$B$_4$O$_7$·10H$_2$O of aqueous EDTA (4 × 10$^{-4}$ M) solution (1:2:2, V/V). The reactions were stopped after 30 min for 20° C., 1.5 h for 0° C., and 2 h for −10° C.
[b]0.2 eq. of ketone was used.
[c]The epoxides were purified by flash chromatography and gave satisfactory spectroscopic characterization.
[d]The yield is for the mixture of trans- and cis-epoxides. In entry 7, 29.3% ee (GC) was obtained for the cis-epoxide; in entry 8, 25.7% ee (GC) was obtained for the cis-epoxide.
[e]Enantioselectivity was determined by chiral HPLC (Chiralcel OD).
[f]Enantioselectivity was determined by chiral GC (Chiraldex γ-TA column).
[g]Enantioselectivity was determined by $^1$H NMR shift analysis of the epoxide products directly with Eu(hfc)$_3$.
[h]Enantioselectivity was determined by $^1$H NMR shift analysis of the derived acetate with Eu(hfc)$_3$.
[i]The epoxide was opened (NaOMe—MeOH) and the resulting alcohol was converted to its acetate; enantioselectivity was determined by $^1$H NMR shift analysis of the resulting acetate with Eu(hfc)$_3$.
[j]The absolute configurations were determined by comparing the measured optical rotations with the reported ones.
[K]The absolute configuration was tentatively assumed.

The olefins can bear a wide range of groups, such as tert-butyl silyl (TES) ether, trityl, acetal, chloride, and ester. Trisubstituted olefins also show high selectivity (See Table 5).

TABLE 5

Asymmetric Epoxidation of Representative Trisubstituted Olefins by Ketone 1 & ent-1

| Entry | Substrate | Method[a] | T (° C.) | Yield[b] (%) | ee (%) | Config.[h] |
|---|---|---|---|---|---|---|
| 1 | Ph(CH₃)C=CHPh | A | 0 | 73 | 92[e] | (+)-(R,R) |
|   |   | C | 0 | 89 | 95.5[e] |   |
| 2 | Ph₂C=CHPh | A | 0 | 65 | 92.2[e] | (−)-(R) |
|   |   | C | 0 | 54 | 96.7[e] |   |
| 3 | 1-phenylcyclohexene | A | 0 | 69 | 91[f] | (−)-(R,R) |
|   |   | C | −10 | 94 | 98[f] |   |
| 4 | 4-phenyl-dihydronaphthalene | A | 0 | 74 | 94[e] | (−)-(1S,2R)[i] |
|   |   | C | −10 | 98 | 95.2[e] |   |
| 5 | Ph₂C=CH-C₁₀H₂₁ | B | 0 | 66 | 93.5[e] | (+)-(R) |
|   |   | C | 0 | 92 | 97.0[e] |   |
| 6 | Ph(CH₃)C=CHCH₃ | C | −10 | 89[c] | 96.8[f] | (R,R)[i] |
| 7 | PhCH=C(CH₃)₂ | C | −10 | 93 | 76.4[f] | (+)-(R)[i] |
| 8 | C₁₀H₂₁CH=C(CH₃)₂ | C | −10 | 97 | 86.5[g] | (+)-(R) |
| 9 | (CH₃)₃C-CH=C(CH₃)₂ | C | −10 | 35 (100[d]) | 91[f] | (−)-(R)[i] |
| 10 | C₁₀H₂₁CH=C(Et)₂ | C | −10 | 94 | 88.5[g] | (+)-(R)[i] |
| 11 | C₆H₁₃CH=C(CH₃)CH₂CH₂CO₂Et | C | −10 | 91 | 83.5[g] | (+)-(R,R)[i] |
| 12 | Cy-CH=C(CH₃)CH₂CH₂CO₂Me | C | −10 | 89 | 94[g] | (+)-(R,R)[i] |

TABLE 5-continued

Asymmetric Epoxidation of Representative Trisubstituted Olefins by Ketone 1 & ent-1

| Entry | Substrate | Method[a] | T (°C.) | Yield[b] (%) | ee (%) | Config.[h] |
|---|---|---|---|---|---|---|
| 13 | (1-methylcyclohexene) | C | −10 | 77 (100[d]) | 81[f] | (+)-(1S,2R) |
| 14 | (methyl-dioxolane-cyclohexene) | C (ent-1) | −10 | 41 | 97.2[f] | (−)-(R,R)[i] |

Table 5 legend:
[a]Methods are the same as in Table 4.
[b]The epoxides were purified by flash chromatography and gave satisfactory spectroscopic characterization.
[c]The yield is for the mixture of trans- and cis-epoxides. 83% ee (GC) was obtained for the cis-epoxide.
[d]The conversion determined by GC (HP-17 column).
[e]Enantioselectivity was determined by chiral HPCL (Chiralcel OD).
[f]Enantioselectivity was determined by chiral GC (Chiraldex -TA column).
[g]Enantioselectivity was determined by $^1$H NMR shift analysis of the epoxide products directly with Eu(hfc)$_3$.
[h]The absolute configurations were determined by comparing the measured optical rotations with the reported ones.
[i]The absolute configuration was tentatively assumed.

The methods of the present invention can also be used for epoxidation of cis-disubstituted and terminal olefins as shown in Table 6.

TABLE 6

Asymmetric Epoxidation of Representative cis-Distributed & Terminal Olefins by Ketone 1.

| Entry | Substrate | Method[a] | T (°C.) | Yield[b] (%) | ee (%) | Config.[f] |
|---|---|---|---|---|---|---|
| 1 | Ph-CH=CH- | B<br>C | −10<br>−10 | 64<br>90 | 13.6[c]<br>24.3[c] | (+)-(R) |
| 2 | C$_8$H$_{17}$-CH=CH- | B<br>C | −10<br>−10 | 80<br>92 | 27[e]<br>17[e] | (+)-(R) |
| 3 | iPr$_3$Si-CH$_2$-CH=CH- | B<br>C | −10<br>−10 | 92.2<br>99 | 35[e]<br>31[e] | (−)[g] |
| 4 | Ph-C(=CH$_2$)-CH$_3$ | B<br>C | −10<br>−10 | 81.3<br>95 | 27.6[d]<br>19.6[d] | (−)-(S) |
| 5 | (dihydronaphthalene) | B<br>C | −10<br>−10 | 85.2<br>92 | 32[e]<br>12[e] | (−)-(1S,2R) |

TABLE 6-continued

Asymmetric Epoxidation of Representative cis-Distributed & Terminal Olefins by Ketone 1.

| Entry | Substrate | Method[a] | T (°C.) | Yield[b] (%) | ee (%) | Config.[f] |
|---|---|---|---|---|---|---|
| 6 | 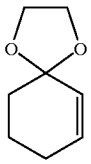 | B<br>C | −10<br>−10 | 50<br>43 | 56.2[c]<br>61.4[c] | (+)-(R,R) |

Table 6 legend:
[a]Methods are the same as in Table 4. All reactions were stopped after 2 h.
[b]The epoxides were purified by flash chromatography and gave satisfactory spectroscopic characterization.
[c]Enantioselectivity was determined by chiral GC (Chiraldex γ-TA column).
[d]Enantioselectivity was determined by chiral HPLC (Chiralcel OD).
[e]Enantioselectivity was determined by $^1$H NMR shift analysis of the epoxide products directly with Eu (hfc)$_3$.
[f]The absolute configurations were determined by comparing the measured optical rotations with the reported ones.
[g]The absolute configuration is not ascertained.

As shown in Table 7, the size of substituent group on the olefin also effects the %ee of the epoxide product. For example, in tri-substituted olefins of a general structure:

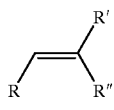

decreasing the size of R' increases the %ee. And increasing the size of R also increases the %ee. Simultaneously decreasing the size of R and increasing the size of $R_3$ further enhances the %ee.

TABLE 7

The effect of the size of substituents on
enantioselectivities using chiral ketone 1 (see FIG. 1)

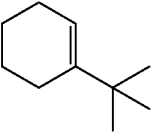

26% ee

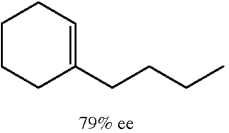

79% ee

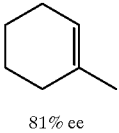

81% ee

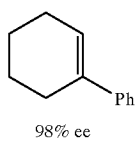

98% ee

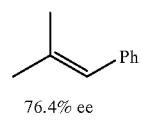

76.4% ee

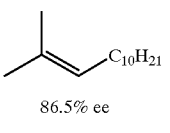

86.5% ee

TABLE 7-continued

The effect of the size of substituents on
enantioselectivities using chiral ketone 1 (see FIG. 1)

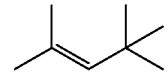

91% ee

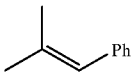

76.4% ee

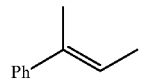

96.8% ee

As shown in Table 8, the methods of the present invention can also be used in regio- and enantioselective monoepoxidation of conjugated polyenes. A "polyene" is a compound which has more than one unsaturated bonds including dienes, trienes and enynes. Using the methods of the present invention, monoepoxidation of polyenes can be achieved by the use of appropriate amount of chiral ketone as a catalyst. If both olefins in a diene are disubstituted, regioselectivity can be controlled by using steric and/or electronic effects. For example, as shown in entry 3 of Table 8, a presence of an electron withdrawing group results in formation of the distal epoxide as the major product. And allylic withdrawing groups such as an acetate which is not conjugated to the olefin can also substantially deactivate the proximal olefin by the inductive effect (see entry 4 of Table 8). The regioselectivity can also be effected by steric hindrance. As illustrated in Table 8, entry 6, steric hindrance can be used to control the formation of a single monoepoxide from a polyene compound. As shown by entry 7 of Table 8, when a diene contains a disubstituted and a trisubstituted olefins, the epoxidation occurs selectively on the trisubstituted olefin.

TABLE 8

Asymmetric Epoxidation of Representative Dienes by Ketone 1[a]

| Entry | Dienes | Epoxides | % Conv | Ratio | % Yield | % ee |
|---|---|---|---|---|---|---|
| 1 | | | 94[e] | 22:1 | 77 | 98.2[k] |
| 2 | | | 100[f] | 12:1 | 54 | 95[k] |
| 3 | | | 69[g,h] | 7:1 | 41(7) | 96(69)[k] |
| 4 | | | 100[e] | 4:1 | 74(18) | 92(90)[m] |
| 5 | | | 100[e] | 4:1 | 68(13) | 96(90)[m] |
| 6 | | | 100[f] | only | 72 | 88[k] |
| 7 | | | 100[e] | only | 68[l] | 90[i] |
| 8 | | | 88[g] | only | 82 | 95[k] |
| 9 | | | 76[g] | only | 68 | 93[k] |
| 10 | | | 100[g] | 3.3:1 | 65[j] | 87[n] |
| 11 | | | 100[g] | only | 77[i] | 94[n] |
| 12 | | | 100[g] | only | 81[i] | 95[n] |
| 13 | | | 100[f] | only | 60[i] | 92[n] |

TABLE 8-continued

Asymmetric Epoxidation of Representative Dienes by Ketone 1[a]

| Entry | Dienes | Epoxides | % Conv | Ratio | % Yield | % ee |
|---|---|---|---|---|---|---|
| 14 | | | 100[g] | only | 79[i] | 95[n] |

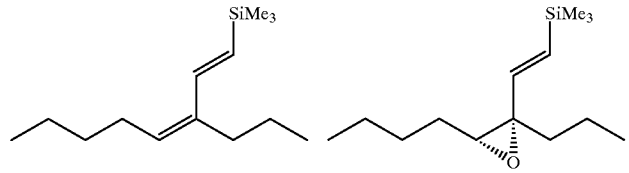

TABLE 8 legend:
[a]Reactions were carried out at 0 C. with 1.0 eq. diene, 0.2–0.3 eq. ketone, 1.12–1.38 eq. Oxone ®, and 5.8 eq. $K_2CO_3$ in $CH_3CN$-DMM-0.05 M $Na_2B_4O_7$ $10H_2O$ of aqueous EDTA (4 × $10^{-4}$ M) solution (1:2:2, v/v). Oxone was added over 1.5 h unless otherwise stated and the reactions were stopped immediately thereafter.
[b]The conversions were determined by $^1H$ NMR except for entry 4 where GC was used.
[c]The ratios were determined by $^1H$ NMR. For symmetric dienes the ratio refers to the monoepoxide/bisepoxide ratio. For unsymmetric dienes it refers to the ratio of the two monoepoxides.
[d]The number in parentheses refers to the yield of the minor epoxide.
[e]0.25 eq. of chiral ketone catalyst used.
[f]0.2 eq. of chiral ketone catalyst used.
[g]0.3 eq. of chiral ketone catalyst used.
[h]Oxone was added over 4 h.
[i]Trace amounts of bisepoxide detected in the crude reaction mixtures.
[j]The epoxide proximal to $SiMe_3$ group detected in the crude reaction mixtures.
[k]Enantioselectivities determined by chiral HPLC (Chiralcel OD).
[m]Enantioselectivities determined by chiral GC.
[n]Enantioselectivity determined by chiral shift NMR.
[o]The number in parentheses refers to the % ee of the minor epoxide.

One of the advantages of the present invention is availability of relatively inexpensive starting materials for producing chiral ketones. For example, as shown in FIG. 1, chiral ketones can be easily synthesized in high overall yield from readily available carbohydrates such as fructose and sorbose. In addition, chiral ketones of the present invention can also be synthesized from other inexpensive and readily available compounds such as carvone, inositol, and quinic acid. Some of the chiral ketones which can be easily prepared from readily available starting materials and their representative epoxidation of olefins are shown in FIGS. 4–11.

Asymmetric epoxidation of olefins according to the present invention can be performed in a variety of different sequences. The addition sequence of the olefin, ketone, base and oxidizing agents can be interchanged depending on the nature of each components. Typically, however, an aqueous solution comprising an oxidizing agent and a separate base solution or a solid oxidizing agent and a solid base are added to a solution comprising the ketone and the olefin. A reverse-addition technique can also be used depending upon the reactivity of each component. A reverse-addition is where the solution comprising the ketone is added to the solution comprising the oxidizing agent or to a solid oxidizing agent. Preferably, the initial concentration of the olefin is from about 0.001 mole/liter (M) to about 10 M, more preferably from about 0.02 M to about 1 M.

When a solution comprising an oxidizing agent is used, preferably the initial concentration of oxidizing agent is from about 0.1 mole/liter (M) to about 1 M, more preferably from about 0.2 M to about 0.5 M. The rate of addition of the oxidizing agent to the solution comprising the ketone and the olefin will vary depending upon a various factors such as the size of the reaction and the substrates.

Another aspect of the present invention is the ease of separation between the epoxide and the ketone. Some epoxides readily dissolve and remain in relatively non-polar organic solvents such as hexane, pentane, ether, chloroform, dichloromethane, ethyl acetate, and mixtures thereof, whereas the ketone remains in aqueous solution. Typically the reaction mixture is diluted with an extraction solvent to separate the epoxide from the ketone. Additionally, aqueous solution can also be added to the reaction mixture to further facilitate removal of the ketone from the organic layer. After separating the two layers, the extraction solvent layer comprising the epoxide can further be washed with an aqueous solution to further remove the ketone that may be present in the extraction solvent layer. This washing can be repeated until substantially all of the ketone is removed from the extraction solvent layer. Conversely, the aqueous layer can be further washed with the extraction solvent to further obtain the epoxide that may be present in the aqueous layer. Again, this extraction can be repeated until substantially all the epoxide has been obtained. The epoxide which is separated from the ketone can further be purified by any of the current separation methods such as chromatography, distillation, and crystallization.

The asymmetric epoxidation methods of the present invention are environmentally friendly. Water is used as a cosolvent and unlike other current asymmetric epoxidation no toxic metals are involved. Therefore, no special disposal method is required, which significantly reduces the overall cost of the present invention.

Additional objects, advantages, and novel features of this invention will become apparent to those skilled in the art upon examination of the following examples thereof, which are not intended to be limiting.

EXAMPLES

General Methods

Oxone® (potassium peroxymonosulfate) was purchased from Aldrich (Milwaukee, Wis.). It has been found that the oxidation activity of the purchased Oxone® occasionally varies with different batches. All glassware used for the epoxidation was carefully washed to be free of any trace metals which catalyze the decomposition of Oxone. The 300 MHZ $^1$H NMR and 75.5 MHZ $^{13}$C NMR spectra were measured on a Bruker ACE-300 spectrometer in CDCl$_3$. Proton chemical shifts (δ) are given relative to internal TMS (0.00 ppm), and Carbon chemical shifts are given relative to CDCl$_3$, (77.23 ppm). Infrared spectra were recorded on a Perkin-Elmer 1600 Series FTIR spectrometer. High-resolution mass spectra were performed by the mass spectrometry facility of Colorado State University. Elemental analyses were performed by M-H-W Laboratories, Phoenix, Ariz. Optical rotations were measured on an Autopol® III automatic polarimeter in a 1 cm cell. Silica gel 60 of E-Merck Co. was employed for all flash chromatography.

As shown in FIG. 1, ketone 1 is readily prepared from very inexpensive D-Fructose by ketalization and oxidation. See Mio et al. *Tetrahedron* 1991, 47, 2133–2144. The enantiomer of ketone catalyst 1 (ketone ent-1) is prepared in the same way from L-fructose (ent-5), which can be prepared from readily available L-sorbose by ketalization, mesylation, and one pot acid-base treatment based on the reported procedure. See Chen et al., *Carbohydr. Res.* 1988, 175, 265–27 1. Ketone ent-1 prepared by this way shows the same enantioselectivity for the epoxidation as ketone 1.

1,2:4,5-Di-O-isopropylidene-D-erythro-2,3-hexodiuro-2,6-pyranose (1)

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After the reaction mixture was stirred under nitrogen at 0° C. for 6 h, concentrate ammonium hydroxide was added to pH=7–8. After the resulting mixture was stirred for another 5 min, the solvent was removed under reduced pressure, and the solid residue was recrystallized from hexane/CH$_2$Cl$_2$ (4/1, V/V) to afford white needles (alcohol 6) (28.34 g, 53.2%) mp 117–118.5° C., $[\alpha]^{25}_D$=−144.2° (c 1.0, CHCl$_3$). IR (KBr): 3547 cm$^{-1}$. $^1$H NMR δ 4.22 (ddd, J=5.7, 2.7, 0.9 Hz, 1H), 4.19 (d, J=9.0 Hz, 1H), 4.13 (dd, J=6.8, 5.7 Hz, 1H), 4.12 (dd, J=13.2, 2.7 Hz, 1H), 4.01 (dd, J=13.2, 0.9 Hz, 1H), 3.98 (d, J=9.0 Hz, 1H), 3.67 (dd, J=8.1, 6.8 Hz, 1H), 1.99 (d, J=8.1 Hz, 1H), 1.54 (s, 3H), 1.52 (s, 3H), 1.44 (s, 3H), 1.37 (s, 3H). $^{13}$C NMR δ112.0, 109.6, 104.7, 77.48, 73.53, 73.52, 70.60, 60.96, 28.13, 26.62, 26.46, 26.14.

PCC (11.64 g, 54 mmol) was added portionwise over 15 min to a mixture of alcohol 6 (5.2 g, 20 mmol) and powdered 3 Å molecular sieves (22 g, activated at 180–200° C. under vacuum) in CH$_2$Cl$_2$ (100 mL). After the reaction mixture was stirred for 3 h under nitrogen, it was filtered through celite and washed carefully with ether. The filtrate was concentrated and the residue was purified by passing through a short silica gel column (hexane:ether=1:1, V/V) to afford a white solid (4.80 g, 93.0%), which was recrystallized from hexane/CH$_2$Cl$_2$ to give white crystals (ketone 1), mp 101.5–103° C. $[\alpha]^{25}_D$=−125.4° (c 1.0, CHCl$_3$). IR (KBr): 1749 cm$^{-1}$. $^1$H NMR δ4.73 (d, J=5.7 Hz, 1H), 4.61 (d, J=9.5 Hz, 1H), 4.55 (ddd, J=5.7, 2.2, 1.0 Hz, 1H), 4.39 (dd, J=13.4, 2.2 Hz, 1H), 4.12 (d, J=13.4 Hz, 1H), 4.00 (d, J=9.5 Hz, 1H), 1.55 (s, 3H), 1.46 (s, 3H), 1.40 (s, 6H). $^{13}$C NMR δ197.1, 114.0, 110.8, 104.3, 78.11, 76.07, 70.20, 60.28, 27.33, 26.70, 26.24, 26.20. Anal. Calcd for C$_{13}$H$_{20}$O$_5$: C, 55.81; H, 7.02. Found: C, 55.47; H, 7.10.

1,2:4,5-Di-O-isopropylidene-L-erythro-2,3-hexodiuro-2,6-pyranose (ent-1)

A solution of 1,2-dimethoxyethane (0.5 mL) containing SnCl$_2$ (0.0125 g, 0.066 mmol) was added to a suspension of L-sorbose (5 g, 27.75 mmol) in 2,2-dimethoxypropane (15 mL). The mixture was refluxed gently with stirring until it was clear, then evaporated to a syrup (alcohol 8).

The syrup was dissolved in CH$_2$Cl$_2$ (15 mL), followed by the addition of pyridine (3.5 mL, 43.3 mmol) and DMAP (catalytic amount). The solution was then cooled in an ice bath, and methanesulfonyl chloride (3.3 mL, 42.6 mmol) was added dropwise. After the reaction mixture was stirred for 2 h at 0° C., water was added. The mixture was extracted with CH$_2$Cl$_2$. The combined organic layers were washed with brine, dried (Na$_2$SO$_4$), filtered, and concentrated to give crude mesylate 9. Recrystallization from ethanol gave colorless needles (3.63 g, 41% yield for two steps). [In a separate run the crude mesylate was flash chromatographed (hexane:EtOAc=3:1, V/V) to give 9 as a pale yellow solid (5.3 g, 60%)]. mp 120–121° C. IR (KBr) 1376, 1348, 1181, 1071 cm$^{-1}$. $^1$H NMR δ4.87 (d, J=1.8 Hz, 1H), 4.47 (dd, J=3.0, 1.8 Hz, 1H), 4.25 (d, J=9.7 Hz, 1H), 4.22 (m, 1H), 4.20 (d, J=9.7 Hz, 1H), 4.01 (dd, J=13.2, 3.2 Hz, 1H), 3.92 (dd, J=13.2, 3.2 Hz, 1H), 1.56 (s, 3H), 1.48 (s, 3H), 1.43 (s, 3H), 1.39 (s, 3H). $^{13}$C NMR δ111.8, 110.0, 98.47, 84.4, 73.53, 73.42, 72.31, 60.54, 39.07, 28.30, 26.13, 26.14, 20.14.

To a solution of mesylate 9 (29.5 g, 87.3 mmol) in acetone (236 mL), was added an aqueous solution of 0.25% H$_2$SO$_4$ (177 mL). After being stirred at 25° C. for 20 h, the solution was made alkaline with 9 M NaOH (23.6 mL). The resulting mixture was heated at 70–80° C. for 48 h, acidified to pH of about 1 with 9 M H$_2$SO$_4$, and heated at 70–80° C. for 20 min. After being neutralized with 2 M NaOH, the mixture was taken to dryness and the residue was extracted with ethanol (500 mL). The ethanol solution was concentrated to a syrup (L-fructose) (14 g, 85%).

The resulting crude L-fructose was directly converted to ketone ent-1 using the same procedure as D-fructose. The resulting ketone ent-1 [mp 102–103° C. $[\alpha]^{25}_D$=+123° (c 0.58, CHCl$_3$)] showed the same enantioselectivity as ketone 1.

Procedure for pH Study

To a 100 mL three-neck round bottom flask were added buffer (10 mL) [4×10$^{-4}$ M aq. Na2EDTA adjusting with 1.0 M KOH for pH 7.5–8.0; 0.05 M Na$_2$B$_4$O$_7$.10H$_2$O in 4×10$^{-4}$ M aq. Na$_2$EDTA adjusting with 1.0 M aq. KH$_2$PO$_4$ for pH 8.5–10.5; 0.05 M aq K$_2$HPO$_4$ plus 0.1 M aq. NaOH (2:1, V/V) adjusting with 1.0 M KH$_2$PO$_4$ for pH 11.0–12.0; 0.05 M aq K$_2$HPO$_4$ plus 0.1 M aq. NaOH (2:1, V/V) adjusting with 1.0 M KOH for pH 12.5–13.0], acetonitrile (15 mL), trans-β-methylstyrene (0.118 g, 1 mmol), tetrabutylammonium hydrogen sulfate (0.015 g, 0.04 mmol), and ketone 1 (0.0516 g, 0.2 mmol). The reaction mixture was cooled by an ice bath. A solution of Oxone® (1.54 g, 2.5 mmol) in aq. Na$_2$EDTA (4×10$^{-4}$ M, 10 mL) was added through a syringe pump at a speed of 4.1 mL/h. The reaction pH was monitored by a Corning 320 pH meter with a Corning "3 in 1" pH combination electrode and was maintained within ±0. 1 by adding 0.5 N aq. KOH. The conversion and ee values were checked by GC every 30 min.

General Epoxidation Procedures

Method A

Aqueous Na$_2$EDTA (1×10$^{-4}$ M, 10 mL) and a catalytic amount of tetrabutylammonium hydrogen sulfate were added to a solution of trans-stilbene (0.18 g, 1 mmol) in acetonitrile (15 mL) with vigorous stirring at 0° C. A mixture of Oxone® (3.07 g, 5 mmol) and sodium bicarbonate (1.3 g, 15.5 mmol) was pulverized and a small portion of this mixture was added to the reaction mixture to bring the pH to >7. After 5 min, ketone 1 (0.77 g, 3 mmol) was added portionwise over a period of 1 h. Simultaneously, the rest of Oxone® and sodium bicarbonate was added portionwise over 50 min. After the completion of the addition of ketone 1, the reaction mixture was stirred for another 1 h at 0° C., diluted with water (30 mL), and extracted with hexanes (4×40 mL). The combined extracts were washed with brine, dried ($Na_2SO_4$), filtered, concentrated, and purified by flash chromatography [the silica gel was buffered with 1% triethylamine solution in hexane; hexane/ether (1/0 to 50/1, V/V) was used as the eluent] to afford trans-stilbene oxide as white crystals (0.149 g, 73% yield, 95.2%ee).

Method B

To a 100 mL three-neck round bottom flask, were added buffer (0.05 M $Na_2B_4O_7.10H_2O$ in $4\times10^{-4}$ M aq. $Na_2EDTA$, 10 mL), acetonitrile (15 mL), trans-β-methylstyrene (0.118 g, 1 mmol), tetrabutylammonium hydrogen sulfate (0.015 g, 0.04 mmol), and ketone 1 (0.0774 g, 0.3 mmol). The reaction mixture was cooled by an ice bath. A solution of Oxone® (0.85 g, 1.38 mmol) in aq. Na2EDTA ($4\times10^{-4}$ M, 6.5 mL) and a solution of $K_2CO_3$ (0.8 g, 5.8 mmol) in water (6.5 mL) were added dropwise through two separate addition funnels over a period of 1.5 h (under this condition, the reaction pH is around 10.5. It is recommended that both Oxone® and $K_2CO_3$ be added uniformly over 1.5 h). At this point, the reaction was immediately quenched by addition of pentane and water. The mixture was extracted with pentane (3×30 mL), washed with brine, dried over $Na_2SO_4$, purified by flash chromatography [the silica gel was buffered with 1% $Et_3N$ in pentane, pentane/ether (1/0 to 50/1, V/V) was used as eluent] to afford trans-β-methylstyrene oxide as colorless liquid (0.124 g, 93 yield, 92%ee).

Method C (a) Reaction at 20° C.: trans-Stilbene (0.181 g, 1 mmol) was dissolved in acetonitrile/DMM (15 mL, ½, V/V). subsequently were added buffer (10 mL, 0.05 M solution of $Na_2B_4O_7.H_2O$ in $4\times10^{-4}$ M aqueous $Na_2EDTA$), tetrabutylammonium hydrogen sulfate (0.015 g, 0.04 mmol), and ketone 1 (0.0774 g, 0.3 mmol). A solution of Oxone® (1.0 g, 1.6 mmol) in aqueous $Na_2EDTA$ ($4\times10^{-4}$ M, 6.5 mL) and a solution of $K_2CO_3$ (0.93 g, 6.74 mmol) in water (6.5 mL) were added dropwise separately over a period of 30 min (via additional funnels). The reaction was then worked up by the same procedure as Method A to afford trans-stilbene oxide (0.166 g, 85% yield, 97.9%ee).

(b) Reaction at 0° C.: trans-Stilbene (0.181 g, 1 mmol) was dissolved in acetonitrile/DMM (15 mL, ½, V/V), subsequently were added buffer (10 mL, 0.05 M solution of $Na_2B_4O_7.H_2O$ in $4\times10^{-4}$ M aqueous $Na_2EDTA$), tetrabutylammonium hydrogen sulfate (0.015 g, 0.04 mmol), and ketone 1 (0.0774 g, 0.3 mmol). The mixture was cooled by an ice bath. A solution of Oxone® (0.85 g, 1.38 mmol) in aqueous $Na_2EDTA$ ($4\times10^{-4}$ M, 6.5 mL) and a solution of $K_2CO_3$ (0.8 g, 5.8 mmol) in water (6.5 mL) were added dropwise separately over a period of 1.5 h (via syringe pumps or additional funnels). The reaction was then worked up by the same procedure as Method A to afford trans-stilbene oxide (0.153 g, 78% yield, 98.9%ee).

(c) Reaction at −10° C.: trans-β-methylstyrene (0.181 g, 1 mmol) was dissolved in acetonitrile/DMM (15 mL, ½, V/V). Buffer (10 mL, 0.05 M solution of $Na_2B_4O_7.H_2O$ in $4\times10^{-4}$ M aqueous $Na_2EDTA$), tetrabutylammonium hydrogen sulfate (15 mg, 0.04 mmol), and ketone 1 (0.0774 g, 0.3 mmol) were added with stirring. The mixture was cooled to about −10° C. (inside) (outside temperature was about −12° C. to −15° C.) via a NaCl-ice bath. A solution of Oxone® (0.85 g, 1.38 mmol) in aqueous $Na_2EDTA$ ($4\times10^{-4}$ M, 6.5 mL) and a solution of $K_2CO_3$ (0.8 g, 5.8 mmol) in water (6.5 mL) were added dropwise separately over a period of 2 h (via syringe pumps or addition funnels). The reaction was then worked up by the same procedure as Method B to afford trans-β-methylstyrene oxide (0.126 g, 94% yield, 95.5%ee).

trans-Stilbene oxide (Table 4, entry 1): White crystals. mp 68–70° C., $[\alpha]^{25}_D$=+356.1° (c 0.95, benzene); −358. 1° (c 0.82, benzene) [Table 4, entry 1, Method C (ent-1)].

trans-β-Methylstyrene oxide (Table 4, entry 2): Colorless oil. $[\alpha]^{25}_D$=+47.8° (c 1.04, $CHCl_3$) (Table 4, entry 2, Method C) ; −46.9° (c 0.88, $CHCl_3$) [Table 4, entry 2, Method C (ent-1)].

(R,R)-2-[(tert-Butyldimethylsiloxy)methyl]-3-phenyloxirane (Table 4, entry 3): The olefin substrate was prepared from cinnamyl alcohol and tert-butyldimethylsilyl chloride. See Corey et al., *J. Am. Chem. Soc.* 1972, 94, 6190–6191. Colorless oil. IR (KBr): 3060, 3027, 2954, 2931, 2856, 1656, 1599, 1495, 1467, 1379, 1254, 1125, 1073, 964, 834, 777, 729, 690 $cm^{-1}$. $^1H$ NMR δ7.36–7.1 (m, 5H), 6.54 (dt, J=15.9, 1.8 Hz, 1H), 6.23 (dt, J=15.9, 5.1 Hz, 1H), 4.3 (dd, J=5.1, 1,8 Hz, 2H), 0.89 (s, 9H), 0.062 (s, 6H). $^{13}C$ NMR δ137.3, 129.7, 129.3, 128.7, 127.5, 126.6, 64.06, 26.18, 18.65, −4.947.

Epoxide: Colorless oil, $[\alpha]^{25}_D$=+39.7° (c 1.0, $CH_2Cl_2$) (Table 4, entry 3, Method C). IR (KBr): 3062, 3030, 2954, 2931, 2857, 2890, 1605, 1498, 1464, 1385, 1254, 1138, 1106, 1050, 887, 836, 778, 697 $cm^{-1}$. $^1H$ NMR δ7.4–7.2 (m, 5H), 3.97 (dd, J=12, 3.3 Hz, 1H), 3.82 (dd, J=12.0, 4.2 Hz, 1H), 3.8 (d, J=2.4 Hz, 1H), 3.14 (ddd, J=4.2, 3.3, 2.4 Hz, 1H), 0.92 (s, 9H), 0.13 (s, 3H), 0.12 (s, 3H). $^{13}C$ NMR δ137.5, 128.7, 128.3, 125.9, 63.24, 62.94, 56.11, 26.1, 18.61, −5.06. HRMS: Calcd for $C_{15}H_{22}O_2Si(M^+-1)$: 263.1465. Found: 263.1467.

(R,R) -2-Phenyl-3-[(triphenylmethoxy)methyl]oxirane (Table 4, entry 4): The olefin was prepared from cinnamyl alcohol and triphenylmethyl chloride according to the procedure by Chaudlrary et al., *Tetrahedron Letter* 1979, 95–98, to yield white crystals. mp 122–124° C. IR (KBr): 3057, 3027, 2925, 2853, 1661, 1597, 1490, 1446, 1219, 1103, 1056, 965, 743, 700 $cm^{-1}$. $^1H$ NMR δ7.55–7.2 (m, 20H), 6.7 (dt, J=15.9, 1.8 Hz, 1H), 6.3 (dt, J=15.9, 5.4 Hz, 1H), 3.78 (dd, J=5.4, 1.8 Hz, 2H). $^{13}C$ NMR δ144.3, 137.3, 130.8, 128.8, 128.7, 128.1, 128.0, 127.6, 127.2, 126.8, 126.6, 87.12, 65.07.

Epoxide: White crystals. mp 116–118° C., $[\alpha]^{25}_D$=+34.1° (c 0.74, $CHCl_3$). IR (KBr): 3056, 3025, 2925, 2863, 1598, 1491, 1448, 1220, 1083, 748 $cm^{-1}$. $^1H$ NMR δ7.5–7.2 (m, 20H), 3.78 (d, J=1.8 Hz, 1H), 3.45 (m, 1H), 3.26 (m, 2H). $^{13}C$ NMR δ144.0, 137.3, 128.9, 128.7, 128.4, 128.1, 127.3, 125.9, 87.05, 64.38, 61.53, 56.36. Anal. Calcd for $C_{28}H_{24}O_2$: C, 85.68; H, 6.16. Found: C, 85.47, H, 6.40.

(2S,3R)-2-(Chloromethyl)-3-phenyloxirane (Table 4, entry 5, Method C): Colorless oil. $[\alpha]^{25}_D$=+26.2° (c 0.9, $CHCl_3$). IR (KBr): 3055, 3033, 2990, 1604, 1497, 1460, 1265, 930, 878, 748, 697 $cm^{-}$. $^1H$ NMR δ7.35–7.15 (m, 5H), 3.77 (d, J=2.1 Hz, 1H), 3.66 (dd, J=12, 5.1 Hz, 1H), 3.60 (dd, J=12.0, 5.7 Hz, 1H), 3.22 (ddd, J=5.7, 5.1, 2.1 Hz, 1H). $^{13}C$ NMR δ136.1, 128.8, 128.8, 125.9, 61.18, 58.76, 44.56. HRMS: Calcd for $C_9H_9ClO (M^+)$: 168.0342; 170.0312 (Cl). Found 168.0349; 170.0312($^{37}$ Cl).

(2S,3R)-2-(Ethylenedioxymethyl)-3-phenyloxirane (Table 4, entry 6): The olefin was prepared by ketalization of cinnamyl aldehyde with ethylene glycol according to the procedure by Daignault et al., *Org. Synth. Collect. Vol V*, 1973, 303–306, to provide a colorless oil. IR (KBr): 3058, 3028, 2956, 2885, 1677, 1600, 1493, 1451, 1394, 1148, 1063, 961, 749, 693 cm$^{-1}$. $^1$H NMR δ7.45–7.2 (m, 5H), 6.78 (d, J=15.9 Hz, 1H), 6.17 (dd, J=15.9, 6.0 Hz, 1H), 6.43 (d, J=6.0 Hz, 1H), 4.1–3.9 (m, 4H). $^{13}$C NMR δ135.9, 135.0, 128.7, 128.5, 127.0, 125.2, 103.9, 65.13.

Epoxide: Colorless oil. $[α]^{25}_D$=+40.5° (c 1.2, CHCl$_3$). IR (KBr): 3058, 3028, 2983, 2889, 1606, 1495, 1468, 1380, 1148, 1115, 944, 756, 699 cm$^{-1}$. $^1$H NMR δ7.4–7.2 (m, 5H), 5.02 (d, J=3.6 Hz, 1H), 4.12–3.91 (m, 4H), 3.90 (d, J=2.1 Hz, 1H), 3.15 (dd, J=3.6, 2.1 Hz, 1H). $^{13}$C NMR δ136.5, 128.7, 128.6, 126.0, 102.6, 65.77, 65.59, 61.58, 55.47. HRMS: Calcd for C$_{11}$H$_{12}$O$_3$ (M$^+$) 192.0786. Found: 192.0783.

(R,R)-2-Methyl-3-(2-methylphenyl)oxirane (Table 4, entry 7): The olefin was prepared from o-methylbenzyltriphenylphosphonium bromide and acetaldehyde by Wittig reaction with a ratio of trans/cis 2.3 (determined by $^1$H NMR). trans-Olefin: $^1$H NMR δ7.41–7.09 (m, 4H), 6.59 (dq, J=15.6, 1.8 Hz, 1H), 6.10 (dq, J=15.6, 6.6 Hz, 1H), 2.33 (s, 3H), 1.90 (dd, J=6.6, 1.8 Hz, 3H). cis-Olefin: $^1$H NMR δ7.41–7.09 (m, 4H), 6.45 (dq, J=11.4, 1.8 Hz, 1H), 5.82 (dq, J=11.4, 6.9 Hz, 1H), 2.25 (s, 3H), 1.74 (dd, J=6.9, 1.8 Hz, 3H).

Epoxides: trans/cis=2.33 (determined by GC). trans-Epoxide: Colorless oil. $[α]^{25}_D$=+29.40 (c 0.32, benzene). IR (KBr): 3062, 3024, 2967, 2927, 1606, 1490, 1458, 1378, 1020, 956, 862, 747 cm$^{-1}$. $^1$H NMR δ7.3–7.2 (m, 4H), 3.71 (d, J=2.1 Hz, 1H), 2.92 (dq, J=5.1, 2.1 Hz, 1H), 2.4 (s, 3H), 1.48 (d, J=5.1 Hz, 3H). $^{13}$C NMR δ136.2, 135.9, 129.9, 127.6, 126.3, 124.3, 58.22, 57.77, 19.02, 18.17. cis-Epoxide: $^1$H NMR δ7.3–7.2 (m, 4H), 4.04 (d, J=4.5 Hz, 1H), 3.41 (dq, J=5.4, 4.5 Hz, 1H), 2.33 (s, 3H) 1.01 (d, J=5.4 Hz, 3H). $^{13}$C NMR δ135.8, 134.0, 129.7, 127.4, 126.7, 125.7, 56.68, 54.69, 18.86, 13.06. Anal. Calcd for C$_{10}$H$_{12}$O (trans & cis): C, 81.04; H, 8.16. Found: C, 81.21; H, 8.16.

(R,R)-2-Isopropyl-3-(2-methylphenyl)oxirane (Table 4, entry 8): The olefin was prepared from o-methylbenzyltriphenylphosphonium bromide and isobutyradehyde via Wittig reaction with a ratio of trans/cis=4.1 (determined by $^1$H NMR). trans-Olefin: $^1$H NMR δ7.44–7.1 (m, 4H), 6.53 (d, J=15.7 Hz, 1H), 6.05 (dd, J=15.7, 6.6 Hz, 1H), 2.48 (m, J=6.6 Hz, 1H), 2.33 (s, 3H), 1.10 (d, J=6.6 Hz, 6H). cis-Olefin: $^1$H NMR δ7.44–7–10 (m, 4H), 6.29 (d, J=11.4 Hz, 1H), 5.51 (dd, J=11.4, 10.2 Hz, 1H), 2.62 (m, 1H), 2.25 (s, 3H), 0.98 (d, J=6.6 Hz, 3H).

Epoxides: trans/cis=3.8 (determined by GC). trans-Epoxide: Colorless oil. $[α]^{25}_D$=−21.2° (c 0.6, benzene). IR (KBr): 3062, 3025, 2962, 2872, 1606, 1491, 1463, 1382, 1366, 1043, 945, 895, 750 cm$^{-1}$. $^1$H NMR δ7.3–7.1 (m, 4H), 3.79 (d, J=2.1 Hz, 1H), 2.62 (dd, J=6.9, 2.1 Hz, 1H), 2.39 (s, 3H), 1.69 (m, 1H), 1.11 (d, J=6.6 Hz, 3H), 1.06 (d, J=6.6 Hz, 3H). $^{13}$C NMR δ136.4, 135.7, 129.9, 127.6, 126.3, 67.86, 56.05, 31.19, 19.43, 19.06, 18.69. cis-Epoxide: $^1$H NMR δ7.3–7.2 (m, 4H), 4.07 (d, J=4.2 Hz, 1H), 2.94 (dd, J=8.4, 4.2 Hz, 1H), 2.36 (s, 3H), 1.61 (m, 1H), 1.1 (d, J=6.6 Hz, 3H), 0.71 (d, J=6.6 Hz, 3H). $^{13}$C NMR δ135.6, 134.2, 129.7, 127.3, 126.2, 125.6, 65.1, 56.94, 26.37, 20.24, 18.96, 18.46. Anal. Calcd for C$_{12}$H$_{16}$O (trans & cis): C, 81.77; H, 9.15. Found: C, 81.80; H, 9.36.

(R,R)-2-[(tert-Butyldimethylsiloxy)methyl]-3-propyloxirane (Table 4, entry 9): The olefin was prepared from trans-2-hexene-1-ol and tert-butyldimethylsilyl chloride according to the procedure by Corey et al., *J. Am. Chem. Soc.* 1972, 94, 6190–6191, to provide a colorless oil. IR (KBr): 2957, 2931, 2858, 1671, 1465, 1381, 1255, 1104, 1062, 969. 838, 776 cm$^{-1}$. $^1$H NMR δ5.65 (dt, J=15.3, 6.3 Hz, 1H), 5.53 (dt, J=15.3, 5.1 Hz, 1H), 4.13 (d, J=5.1 Hz, 2H), 2.01 (dt, J=6.6, 6.3 Hz, 2H), 1.4 (m, J=7.5, 6.6 Hz, 2H), 0.91 (t, J=7.5 Hz, 3H), 0.914 (s, 9H), 0.075 (s, 6H). $^{13}$C NMR δ131.5, 129.5, 64.31, 34.54, 26.2, 22.59, 18.65, 13.91, −4.89.

Epoxide: Colorless oil. $[α]^{25}_D$=+17.7° (c 0.74, CHCl$_3$) (Table 4, entry 9, Method C). IR (KBr): 2957, 2932, 2859, 1467, 1254, 1129, 1095, 838, 778, 665 cm$^-$. $^1$H NMR δ3.78 (dd, J=11.7, 3.4 Hz, 1H), 3.67 (dd, J=11.7, 4.5 Hz, 1H), 2.87–2.79 (m, 2H), 1.6–1.4 (m, 4H), 0.96 (t, J=7.2 Hz, 3H), 0.90 (s, 9H), 0.078 (s, 3H), 0.069 (s, 3H). $^{13}$C NMR δ63.9, 58.85, 56.43, 33.94, 26.08, 19.51, 18.56, 14.11, −5.076, −5.133. HRMS: Calcd for C$_{12}$H$_{25}$O$_2$Si (M$^+$−1) 229.1623. Found: 229.1618.

(R,R)-2-[1-(tert-Butyldimethylsiloxy)ethyl]-3-ethyloxirane (Table 4, entry 10): The olefin was prepared from trans-3-hexene-1-ol and tert-butyldimethylsilyl chloride according to the procedure by Corey et al., *J. Am. Chem. Soc.* 1972, 94, 6190–6191, to provide a colorless oil. IR (KBr): 2957, 2931, 2858, 1468, 1384, 1254, 1103, 966, 836. 776 cm$^{-1}$. $^1$H NMR δ5.53 (dt, J=15.3, 6.0 Hz, 1H), 5.39 (dt, J=15.3, 6.6 Hz, 1H), 3.62 (t, J=6.9 Hz, 1H), 2.21 (dt, J=6.9, 6.6 Hz, 1H), 2.01 (m, J=7.5, 6.0 Hz, 2H), 0.97 (t, J=7.5 Hz, 3H), 0.90 (s, 9H), 0.059 (s, 6H). $^{13}$C NMR δ134.3, 125.6, 63.6, 36.52, 26.17, 25.91, 18.6, 14.02, −5.028

Epoxide: Colorless oil. $[α]^{25}_D$=+23.9° (c 1.1, CHCl$_3$) (Table 4, entry 10, Method C). IR (KBr): 2956, 2932, 2859, 1469, 1386, 1254, 1100, 940, 891, 837, 777, 728, 663 cm$^1$. $^1$H NMR δ3.75 (dd, J=6.3, 6.0 Hz, 2H), 2.8 (dt, J=6.0, 2.4 Hz, 1H), 2.69 (dt, J=5.4, 2.4 Hz, 1H), 1.82–1.63 (m, 2H), 1.57 (m, 2H), 0.99 (t, J=7.5 Hz, 3H), 0.90 (s, 9H), 0.06 (s, 6H). $^{13}$C NMR δ60.27, 60.17, 56.27, 35.79, 26.12, 25.36, 18.49, 10.05, −5.182. HRMS: Calcd for C$_{12}$H$_{25}$O$_2$Si (M$^+$−1): 229.1623. Found: 229.1622.

(R,R)-2,3-Dihexyloxirane (Table 4, entry 11): Colorless oil. $[α]^{25}_D$=+26.2° (c 0.7 l, CHCl$_3$). IR (KBr): 2958, 2928, 2857, 1463, 1378, 1250, 1086, 901, 840, 721 cm$^{-1}$. $^1$H NMR δ2.66 (m, 2H), 1.6–1.2 (m, 20H), 0.89 (t, J=6.9 Hz, 6H). $^{13}$C NMR δ59.1, 32.33, 31.95, 29.3, 26.2, 22.74, 14.24. HRMS: Calcd for C$_{14}$H$_{28}$O (M$^+$): 212.2140. Found: 212.2138.

(R,R)-2,3-Dibutyloxirane (Table 4, entry 12): Colorless oil. $[α]^{25}_D$=+26.70 (c 0.97, CH$_2$Cl$_2$)

(R,R)-2-Ethyl-3-(4,4-Ethylenedioxypentyl)oxirane (Table 4, entry 13): The olefin was prepared according to Look's method. Look, *J. Chem. Ecol.* 1976, 2, 83–86. Colorless oil. IR (KBr): 2954, 2877, 1457, 1375, 1215, 1060, 966, 860 cm$^{-1}$. $^1$H NMR δ5.5–5.3 (m, 2H), 3.98–3.88 (m, 4H), 2.05–1.93 (m. 4H), 1.68–1.58 (m, 2H), 1.5–1.4 (m, 2H), 1.31(s, 3H), 0.96 (t, J=7.5 Hz, 3H). $^{13}$C. NMR δ132.6, 129.0, 110.4, 64.81, 38.86, 32.85, 25.79, 24.26, 23.97, 14.16.

Epoxide: Colorless oil. $[α]^{25}_D$=+27.90 (c 2.06, ether). IR (KBr): 2967, 2875, 1460, 1376, 1218, 1054, 891 cm$^{-1}$. $^1$H NMR δ3.99–3.89 (m, 4H), 2.70–2.62 (m, 2H), 1.73–1.50 (m, 8H), 1.32 (s, 3H), 0.99 (t, J=7.5 Hz, 3H). $^{13}$C NMR δ110.1, 64.83, 60.04, 58.58, 39.1, 32.38, 25.32, 23.96, 20.79, 10.1.

(R,R)-2-Benzyl-3-[2-(methoxycarbonyl)ethyl]oxirane (Table 4, entry 14): The olefin was prepared by Johnson-Claisen rearrangement from an allylic alcohol resulting from an addition of vinylmagnesium bromide to phenylacetaldehyde according to the method of Johnson et al., *J. Am. Chem. Soc.* 1970, 92, 741–743, to provide a colorless oil. IR (KBr): 3060, 3026, 2950, 2915, 2844, 1739, 1603, 1494, 1438, 1169, 971, 744, 699 cm$^{-1}$. $^1$H NMR δ7.35–7.13 (m, 5H), 5.67 (dt, J=15.3, 6.6 Hz, 1H), 5.54 (dt, J=15.3, 6.0 Hz, 1H), 3.68 (s, 3H), 3.36 (d, J=6.6 Hz, 2H), 2.47–2.34 (m, 4H). $^{13}$C NMR δ173.7, 140.8, 130.4, 129.7, 128.6, 128.5, 126.1, 51.65, 39.09, 34.12, 27.97.

Epoxide: Colorless oil. $[\alpha]^{25}{}_D$=+26.6° (c 1.17, CHCl$_3$) (Table 4, entry 14, Method C). IR (KBr): 1737, 1603, 1495 cm$^{-1}$. $^1$H NMR δ7.4–7.15 (m, 5H), 3.65 (s, 3H), 3.0–2.75 (m, 4H), 2.43 (dd, J=7.8, 7.2 Hz, 2H), 2.05–1.9 (dqd, J=14.4, 7.5, 4.8 Hz, 1H), 1.84–1.7 (dq, J=14.4, 6.9 Hz, 1H). $^{13}$C NMR δ173.43, 137.41, 129.12, 128.75, 126.83, 59.03, 57.65, 51.87, 38.56, 30.40, 27.30. HRMS: Calcd for C$_{13}$H$_{16}$C$_3$ (M$^+$): 220.1099. Found 220.1097.

(R,R)-2-Methyl-2,3-Diphenyloxirane (Table 5, entry 1): Colorless oil. $[\alpha]^{25}{}_D$=+113.9° (c 0.9, EtOH). IR (KBr): 3061, 3031, 2967, 1604, 1496, 1450, 1280, 1064, 1026, 980, 741, 763, 699 cm$^{-1}$. $^1$H NMR δ7.5–7.28 (m, 10H), 3.975 (s, 1H), 1.49 (s, 3H). $^{13}$C NMR 142.6, 136.2, 128.7, 128.4, 127.9, 127.7, 126.7, 125.4, 67.28, 63.27, 16.95.

(R)-2,2,3-Triphenyloxirane (Table 5, entry 2): White crystals. mp 91–92° C., $[\alpha]^{25}{}_D$=−43.2° (c 0.82, EtOH). IR (KBr): 3059, 3031, 1596. 1493, 1447, 748, 685 cm$^{-1}$. $^1$H NMR δ7.5–7.05 (m, 15H), 4.39 (s, 1H). $^{13}$C NMR δ141.2, 136.0, 135.7, 129.4, 128.6, 128.1, 128.0, 127.95, 127.87, 127.8, 127.0, 126.6, 68.88, 68.24.

(R,R)-1-Phenylcyclohexene oxide (Table 5, entry 3): Colorless oil. $[\alpha]^{25}{}_D$=+116.70 (c 1.21, benzene).

(1S,2R)-1-Phenyl-3,4-dihydronaphthalene oxide (Table 5, entry 4): White crystals. mp 124–126° C. $[\alpha]^{25}{}_D$=−42.75° (c 0.95, CHCl$_3$). IR (KBr): 3066, 3028, 2999, 2938, 2846, 1603, 1490, 1450, 1307, 1156, 1042, 954, 906, 872, 757, 705 cm$^{-1}$. $^1$H NMR δ7.5–6.95 (m, 9H), 3.6 (dd, J=2.1, 0.9 Hz, 1H), 2.93 (ddd, J=14.4, 13.2, 6.3 Hz, 1H), 2.68 (dd, J=14.4, 5.7 Hz, 1H), 2.45 (dddd, J=14.4, 6.3, 3.0, 2.1 Hz, 1H), 2.02 (ddd, J=14.4, 13.2, 5.7, 0.9 Hz, 1H). $^{13}$C NMR δ138.9, 137.4, 135.0, 130.0, 128.7, 128.3, 128.2, 128.0, 127.8, 126.1, 63.18, 60.72, 25.59, 22.33. HRMS: Calcd for C$_{16}$H$_{14}$O (M$^+$): 222.1045. Found: 222.1038.

(R)-3-Decyl-2,2-diphenyloxirane (Table 5, entry 5): The olefin was prepared from undecyltriphenylphosphonium bromide and benzophenone via Wittig reaction. IR (KBr): 3056, 3024, 2924, 2854, 1598, 1493, 1461, 1444, 1366, 1073, 1029, 762, 698 cm$^{-1}$. $^1$H NMR δ7.35–7.05 (m, 10H), 6.0 (t, J=7.4 Hz, 1H), 2.02 (dt, J=7.4, 7.4 Hz, 2H), 1.45–1.30 (m, 2H), 1.26–1.1 (m, 14H), 0.8 (t, J=6.5 Hz, 3H). $^{13}$C NMR δ143.2, 141.6, 140.6, 130.6, 130.2, 128.33, 128.3, 127.4, 127.0, 126.9, 32.14, 30.19, 29.98, 29.84, 29.72, 29.56, 29.51, 22.92, 14.34.

Epoxide (Table 5, entry 5, Method C): White solid. mp 31–33° C. $[\alpha]^{25}{}_D$=+30.2° (c 1.24, CCl$_4$). IR (KBr): 3061, 3030, 2924, 2854, 1603, 1495, 1451, 758, 699 cm$^{-1}$. $^1$H NMR δ7.43–7.2 (m, 10H), 3.38 (dd, J=6.6, 4.8 Hz, 1H), 1.5–1.17 (m, 18H), 0.87 (t, J=6.6 Hz, 3H). $^{13}$C NMR δ141.5, 137.9, 128.5, 128.3, 128.2, 127.9, 127.7, 127.2, 66.95, 66.37, 32.12, 29.78, 29.69, 29.66, 29.58, 29.53, 26.42, 22.90, 14.34.

(R,R)-2,3-Dimethyl-2-Phenyloxirane (Table 5, entry 6): The starting α,β-dimethylstyrene was prepared from ethyltriphenylphosphonium iodide and acetophenone via Wittig reaction by the method of Barton et al., Tetrahedron 1990, 46, 5273–5284 with a ratio of trans/cis=5 (determined by $^1$H NMR). trans-Olefin: $^1$H NMR δ7.4–7.15 (m, 5H), 5,85 (q, J=6.9 Hz, 1H), 2.03 (s, 3H), 1.79 (d, J=6.9 Hz, 3H). cis-Olefin: $^1$H NMR δ7.4–7.15 (m, 5H), 5.56 (q, J=6.9 Hz, 1H), 2.03 (s, 3H), 1.59 (d, J=6.9 Hz, 3H).

Epoxide (trans/cis=5.8) (determined by GC): Colorless oil. trans-Epoxide: $^1$H NMR δ7.4–7.2 (m, 5H), 2.97 (q, J=5.4 Hz, 1H), 1.68 (s, 3H), 1.45 (d, J=5.4 Hz, 3H). $^{13}$C NMR δ143.2, 128.5, 127.4, 125.2, 62.72, 60.53, 17.56, 14.62. cis-Epoxide: $^1$H NMR δ7.4–7.2 (m, 5H), 3.20 (q, J=5.4 Hz, 1H), 1.67 (s, 3H), 1.01 (d, J=5.4 Hz, 3H). Anal. Calcd for C$_{10}$H$_{12}$O (trans & cis): C, 81.04; H, 8.16. Found: C, 80.89; H, 8.23.

(R)-2,2-Dimethyl-3-phenyloxirane (Table 5, entry 7): The olefin was prepared from benzyltriphenylphosphonium bromide and acetone via Wittig reaction by the method of Barton et al., Tetrahedron 1990, 46, 5273–5284, to provide a colorless oil. IR (KBr): 3056, 3023, 2970, 2914, 2856, 1655, 1598, 1491, 1442, 1378, 981, 915, 834, 740, 698 cm$^{-1}$. $^1$H NMR δ7.35–7.12 (m, 5H), 6.27 (s, 1H), 1.90 (s, 3H), 1.86 (s, 3H). $^{13}$C NMR δ138.9, 135.7, 128.9, 128.2, 126.0, 125.4, 27.07, 19.58.

Epoxide: Colorless oil. $[\alpha]^{25}{}_D$=+36.8° (c 0.63, benzene). IR (KBr): 3062, 3032, 2962, 2926, 1604, 1495, 1453, 1379, 1246, 1117, 910, 849, 743, 699 cm$^{-1}$. $^1$H NMR δ7.4–7.2 (m, 5H), 3.87 (s, 1H), 1.482 (s, 3H), 1.076 (s, 3H). $^{13}$C NMR δ136.8, 128.2, 127.5, 126.6, 64.77, 61.27, 24.94, 18.14.

(R)-3-Decyl-2,2-Dimethyloxirane (Table 5, entry 8): The olefin was prepared from undecyltriphenylphosphonium iodide and acetone via Wittig reaction. IR (KBr): 2958, 2924, 2854, 1676, 1461, 1377, 984, 832, 721 cm$^{-1}$. $^1$H NMR δ5.12 (t, J=7.2 Hz, 1H), 1.95 (dt, J=7.2, 7.2 Hz, 2H), 1.68 (s, 3H), 1.60 (s, 3H), 1.85–1.2 (m, 16H), 0.88 (t, J=6.7 Hz, 3H). $^{13}$C NMR δ131.3, 125.2, 32.17, 30.17, 29.93, 29.90, 29.86, 29.62, 28.31, 25.93, 22.94, 17.86, 14.33.

Epoxide: Colorless syrup. $[\alpha]^{25}{}_D$=+13.2° (c 0.92, CCl$_4$). IR (KBr): 2956, 2925, 2855, 1462, 1379, 1121, 896, 681 cm$^{-1}$. $^1$H NMR δ2.72 (dd, J=6.6, 5.4 Hz, 1H), 1.6–1.2 (m, 18H), 0.88 (t, J=6.5 Hz, 3H). $^{13}$C NMR δ64.75, 58.34, 32.10, 29.79, 29.78, 29.76, 29.70, 29.52, 29.05, 26.71, 25.10, 22.87, 18.90, 14.28.

(R)-3-tert-Butyl-2,2-dimethyloxirane (Table 5, entry 9): Colorless oil. $[\alpha]^{25}{}_D$=−21.6° (c 0.37, CHCl$_3$). $^1$H NMR δ2.49 (s, 1H), 1.41 (s, 3H), 1.02 (s, 3H), 1.01 (s, 9H). $^{13}$C NMR δ72.76, 59.48, 31.78, 27.94, 27.34, 19.77.

(R)-3-Decyl-2,2-diethyloxirane (Table 5, entry 10): The olefin was prepared from undecyltriphenylphosphonium iodide and 3-pentanone via Wittig reaction. IR (KBr): 2962, 2925, 2854, 1663, 1462, 1374, 924, 855, 721 cm$^{-1}$. $^1$H NMR δ5.07 (t, J=7.0 Hz, 1H), 2.03 (q, J=7.6 Hz, 2H), 2.0 (q, J=7.6 Hz, 2H), 2.05–1.94 (m, 2H), 1.4–1.2 (m, 16H), 0.98 (t, J=7.6 Hz, 3H), 0.95 (t, J=7.6 Hz, 3H), 0.88 (t, J=6.7 Hz, 3H). $^{13}$C NMR δ142.8, 123.2, 32.17, 30.47, 29.91, 29.91, 29.87, 29.67, 29.60, 29.42, 27.8, 23.40, 22.93, 14.33, 13.48, 13.16.

Epoxide: Colorless oil. $[\alpha]^{25}{}_D$=+13.0° (c 1.12, CCl$_4$). IR (KBr): 2963, 2926, 2855, 1463, 1377, 1111, 899, 672 cm$^{-1}$. $^1$H NMR δ2.72 (dd, J=6.3, 5.7 Hz, 1H), 1.7–1.4 (m, 6H) 1.4–1.2 (m, 16H), 0.98 (t, J=7.5 Hz, 3H), 0.92 (t, J=7.5 Hz, 3H), 0.88 (t, J=7.0 Hz, 3H). $^{13}$C NMR δ64.98, 63.92, 32.11, 29.81, 29.79, 29.77, 29.77, 29.54, 28.5, 27.65, 26.98, 22.89, 22.82, 14.31, 9.542, 9.108. HRMS: Calcd for C$_{16}$H$_{33}$O (M$^+$+1): 241.2531. Found: 241.2534.

(R,R)-2-[2-(Ethoxycarbonyl)ethyl]-3-hexyl-2-methyloxirane (Table 5, entry 11): The olefin was prepared by Johnson-Claisen rearrangement from an allylic alcohol resulting from an addition of hexylmagnesium bromide to methacrolein as described by Johnson et al., J. Am. Chem. Soc. 1970, 92, 741–743. Colorless oil. IR (KBr): 2957, 2926, 2855, 1738, 1650, 1457, 1372, 1157, 1038 cm$^{-1}$. $^1$H NMR δ5.16 (t, J=7.1 Hz, 1H), 4.11 (q, J=7.2 Hz, 2H), 2.38 (dd, J=7.5, 6.6 Hz, 2H), 2.29 (dd, J=7.5, 6.6 Hz, 2H), 1.96 (dt, J=7.1, 6.6 Hz, 2H), 1.6 (s, 3H), 1.24 (t, J=7.2 Hz, 3H), 1.35–1.2 (m, 8H), 0.87 (t, J=6.7 Hz, 3H). $^{13}$C NMR δ173.7, 133.3, 125.9, 60.38, 34.94, 33.51, 32.0, 29.9, 29.16, 28.09, 22.86, 16.06, 14.45, 14.28.

Epoxide: Colorless oil: $[\alpha]^{25}{}_D$=+9.4° (c 1.1, CHCl$_3$). IR (KBr): 1736.8 cm$^{-1}$. $^1$H NMR δ4.13 (q, J=7.2 Hz, 2H), 2.73 (dd, J=6.3, 5.7 Hz, 1H), 2.38 (dd, J=8.1, 7.5 Hz, 2H), 1.89 (dd, J=7.5, 4.8 Hz, 1H), 1.86 (dd, J=8.1, 4.8 Hz, 1H), 1.6–1.2 (m, 10H), 1.26 (t, J=7.2 Hz, 3H), 1.25 (s, 3H), 0.89 (t, J=6.7

Hz, 3H), $^{13}$C NMR δ173.3, 63.6, 60.66, 59.91, 33.62, 31.95, 30.12, 29.34, 28.78, 26.61, 22.75, 16.76, 14.39, 14.25. HRMS: Calcd for $C_{14}H_{27}O_3$ (M$^+$+1): 243.1960. Found: 243.1959.

(R,R)-3-Cyclohexyl-2-[2-(methoxycarbonyl)ethyl]-2-methyloxirane (Table 5, entry 12): The olefin was prepared by Johnson-Claisen rearrangement from an allylic alcohol resulting from an addition of cyclohexylmagnesium bromide to methacrolein as described by Johnson et al., *J. Am. Chem. Soc.* 1970, 92, 741–743. Colorless oil. IR (KBr): 2924, 2850, 1740, 1670, 1445, 1348, 1257, 1194, 1159, 1047, 893, 848 cm$^{-1}$. $^1$H NMR δ4.98 (d, J=8.7 Hz, 1H), 3.65 (s, 3H), 2.4 (dd, J=8.1, 7.2 Hz, 2H), 2.27 (dd, J=8.1, 7.2 Hz, 2H), 2.1 (m, 1H), 1.7–1.5 (m, 4H), 1.61 (s, 3H), 1.35–1.1 (m, 4H), 1.0 (m, 2H). $^{13}$C NMR δ174.1, 132.1, 131.5, 51.59, 37.05, 34.94, 33.41, 33.35, 26.29, 26.22, 16.12.

Epoxide: Colorless syrup. $[α]^{25}_D$=+11.6° (c 0.5, CHCl$_3$) IR (KBr): 2928, 2852, 1740, 1447, 1198, 1167 cm$^{-1}$. $^1$H NMR δ3.68 (s, 3H), 2.5–2.3 (m, 3H), 2.0–1.5 (m, 7H), 1.27 (s, 3H), 1.3–1.05 (m, 6H). $^{13}$C NMR δ173.7, 68.03, 59.93, 51.87, 37.52, 33.82, 30.66, 29.99, 29.08, 26.39, 25.73, 25.60, 16.79. HRMS: Calcd for $C_{13}H_{23}O_3$ (M$^+$+1): 227.1647.

Found: 227.1641.

(1S,2R)-1-Methylcyclohexene oxide (Table 5, entry 13): Colorless oil. $[α]^{25}_D$=+27.7° (c 0.68, CHCl$_3$). $^1$H NMR δ2.94 (dt, J=3.3, 1.2 Hz, 1H), 1.94–1.8 (m, 3H), 1.65 (ddd, J=14.7, 8.1, 5.4 Hz, 1H), 1.28 (s, 3H), 1.5–1.1 (m, 4H). $^{13}$C NMR δ59.72, 57.67, 30.06, 24.94, 24.15, 20.22, 19.83.

(R,R)-1-Methyl-3,3-ethylenedioxycyclohexene oxide (Table 5, entry 14): The olefin was prepared by ketalization of 3-methyl-2-cyclohexenone with 1,2-bis(trimethylsiloxy)ethane. See Tsunoda et al., *Tetrahedron Letters* 1980, 21, 1357–1358. Colorless oil. IR (KBr): 2937, 2874, 1675, 1438, 1354, 1189, 1102, 1082, 931 cm$^{-1}$. $^1$H NMR δ5.46 (s, 1H), 3.97 (m, 4H), 1.96 (t, J=5.1 Hz, 2H), 1.83–1.70 (m, 4H), 1.72 (s, 3H). $^{13}$C NMR δ141.8, 122.5, 106.8, 64.57, 33.31, 30.14, 23.59, 21.12.

Epoxide: Colorless oil: $[α]^{25}_D$=–11.3° (c 0.72, CHCl$_3$). IR (KBr): 2953, 2883, 1666, 1442, 1423, 1185, 1139, 1072, 1058, 938, 856 cm$^{-1}$. $^1$H NMR δ4.1–3.95 (m, 4H), 2.82 (s, 1H), 1.90 (m, 1H), 1.70 (m, 2H), 1.52 (m, 2H), 1.42 (m, 1H), 1.36 (s, 3H). $^{13}$C NMR δ107.0, 65.17, 64.95, 61.31, 60.12, 30.99, 28.56, 23.59, 18.14. Anal. Calcd for $C_9H_{14}O_3$: C, 63.51; H, 8.29. Found: C 63.27; H, 8.56.

(R)-Styrene oxide (Table 6, entry 1): Colorless oil. $[α]^{25}_D$=+10.7° (c 0.86, benzene).

(R)-1-Decene oxide (Table 6, entry 2): Colorless oil. $[α]^{25}_D$=+5.2° (c 0.9, ether).

3-(Triisopropylsilyl)propene oxide (Table 6, entry 3): Colorless oil. $[α]^{25}_D$=–9.0° (C 1.45, CHCl$_3$). IR (KBr): 3037, 2942, 2867, 1465, 1387, 1189, 883, 831, 740, 656 cm$^{-1}$. $^1$H NMR δ2.81 (dddd, J=9.0, 4.5, 4.2, 3.0 Hz, 1H), 2.81 (δ, J=4.9, 4.2, 1.2 Hz, 1H), 2.48 (dd, J=4.9, 3.0 Hz, 1H), 1.30 (dd, J=14.3, 4.5 Hz, 1H), 1.07 (m, 3H), 1.06 (d, J=2.7 Hz, 18H), 0.62 (dd, J=14.3, 9.0 Hz, 1H). $^{13}$C NMR δ50.86, 49.86, 18.83, 14.37, 11.20. HRMS: Calcd for $C_{12}H_{27}OSi$ (M$^+$+1): 215.1831. Found: 215.1832.

(S)-α-Methylstyrene oxide (Table 6, entry 4): Colorless oil. $[α]^{25}_D$=–0.5° (c 2.0, acetone).

(1S,2R)-3,4-Dihydronaphthalene oxide (Table 6, entry 5) Colorless oil, $[α]^{25}_D$=–38.8° (c 0.91, CHCl$_3$).

(R,R)-3,3-Ethylenedioxycyclohexene oxide (Table 6, entry 6): The olefin was prepared by ketalization of 2-cyclohexenone with 1,2-bis(trimethylsiloxy)ethane. See Tsunoda et al., *Tetrahedron Letters* 1980, 21, 1357–1358. Colorless oil. IR (KBr): 3031, 2943, 2877, 2836, 1683, 1651, 1439, 1396, 1113, 1028, 935, 732 cm$^{-1}$. $^1$H NMR δ5.96 (dt, J=10.2, 3.6 Hz, 1H), 5.58 (dt, J=10.2, 2.1 Hz, 1H), 3.96 (m, 4H), 2.03 (m, 2H), 1.79 (m, 4H). $^{13}$C NMR δ132.7, 127.5, 105.6, 64.39, 33.48, 24.81, 20.71.

Epoxide (Table 6, entry 6): Colorless oil. $[α]^{25}_D$=+3.6° (c 0.8, CH$_2$Cl$_2$). IR (KBr): 2946, 2884, 1436, 1378, 1336, 1255, 1183, 1120, 1080, 1022, 936, 869 cm$^{-1}$. $^1$H NMR δ4.15–3.9 (m, 4H), 3.31 (δ, J=3.6, 3.6, 0.9 Hz, 1H), 2.99 (d, J=3.6 Hz, 1H), 1.85 (m, 2H), 1.75 (m, 1H), 1.5 (m, 3H). $^{13}$C NMR δ106.8, 65.25, 65.07, 54.42, 54.3, 30.88, 23.03, 18.12.

1-Butylcyclohexene oxide (Table 7): The olefin was prepared by reductive alkylation of cyclohexene oxide with n-BuLi. See Doris et al., *Tetrahedron Letters* 1994, 35, 7943–7946. Colorless oil. IR (KBr): 2924, 2857, 1667, 1457, 918, 798 cm$^{-1}$. $^1$H NMR δ5.38 (m, 1H), 2.02–1.85 (m, 6H), 1.68–1.5 (m, 4H), 1.4–1.2 (m, 4H), 0.89 (t, J=7.1 Hz, 3H). $^{13}$C NMR δ138.3, 120.7, 38.01, 30.18, 28.53, 25.48, 23.3, 22.87, 22.69, 14.25.

Epoxide: Colorless oil. $[α]^{25}_D$=+14.8° (c 1.22, CHCl$_3$). IR (KBr): 2933, 2861, 1458, 1374, 1172, 982, 870, 842, 765, 679 cm$^{-1}$. $^1$H NMR δ2.94 (ddd, J=3.3, 1.2, 0.9 Hz, 1H), 2.0–1.65 (m, 4H), 1.58–1.1 (m, 10H), 0.9 (t, J=7.0 Hz, 3H). $^{13}$C NMR δ60.41, 58.82, 37.76, 27.89, 27.18, 25.1, 23.01, 20.44, 19.9, 14.24. HRMS: Calcd for $C_{10}H_{18}O$ (M$^+$): 154.1358. Found: 154.1350.

1-tert-Butylcyclohexene oxide (Table 7): The olefin was prepared by reductive alkylation of cyclohexene oxide with t-BuLi. See Doris et al., *Tetrahedron Letters* 1994, 35, 7943–7946. Colorless oil. IR (KBr): 2928, 2854, 1656, 1463, 1362, 797 cm$^{-1}$. $^1$H NMR δ5.45 (m, 1H), 2.05–1.93 (m, 4H), 1.65–1.49 (m, 4H), 1.01 (s, 9H). $^{13}$C NMR δ145.8, 117.5, 35.53, 29.25, 25.75, 24.71, 23.76, 22.82.

Epoxide: Colorless oil.$[α]^{25}_D$=+4.7° (c 0. 19, CHCl$_3$). IR (KBr): 2939, 2869, 1481, 1460, 1364, 1036, 918, 875, 767 cm$^{-1}$. $^1$H NMR δ3.12 (ddd, J=3.3, 1.2, 1.2 Hz, 1H), 2.0–1.85 (m, 2H), 1.8–1.65 (m, 2H), 1.55–1.3 (m, 2H), 1.3–1.1 (m, 2H), 0.9 (s, 9H). $^{13}$C NMR δ65.0, 55.45, 34.22, 25.68, 25.40, 24.95, 21.21, 19.79. HRMS: Calcd for $C_{10}H_{18}O$ (M$^+$): 154.1358. Found: 154.1352.

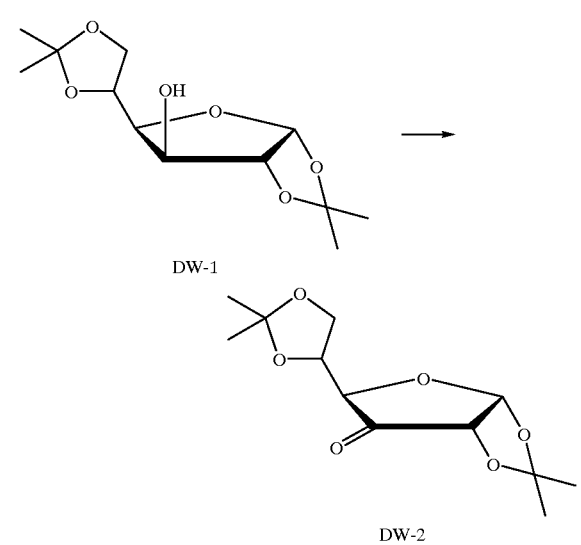

DW-1

DW-2

Preparation of Ketone DW-2

To a solution of alcohol DW-1 (8 g, 30.8 mmol) in dry CH$_2$Cl$_2$ (90 mL) and acetic anhydride (10 mL) were added PDC (12 g, 32 mmol) and freshly activated 3A molecular sieve powder (16 g). After refluxing for 6 hours, the reaction mixture was diluted with ethyl acetate (100 mL), filtered through a glass funnel with celite, concentrated, and purified by flash chromatography (hexane:ether, 1:1) to give ketone DW-2 as a colorless syrup (7.3 g, 90%). $[a]_D 25=+102.1((c\ 2.2, CHCl_3)$. IR (KBr): 1773 cm$^{-1}$. $^1$H NMR: $\delta$6.13 (dd, J=4.5, 1.8 Hz, 1H), 4.4–4.31 (m, 3H), 4.05–4.0 (m, 2H), 1.45, 1.42 (s,, each 3H), 1.33 (s, 6H). $^{13}$C NMR: $\delta$209, 114.5, 110.5, 103.3, 79.12, 77.43, 76.56, 64.48, 27.73, 27.34, 26.15, 25.47.

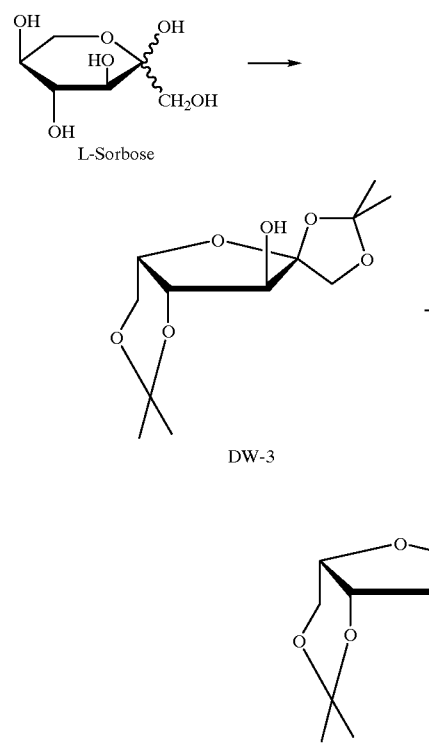

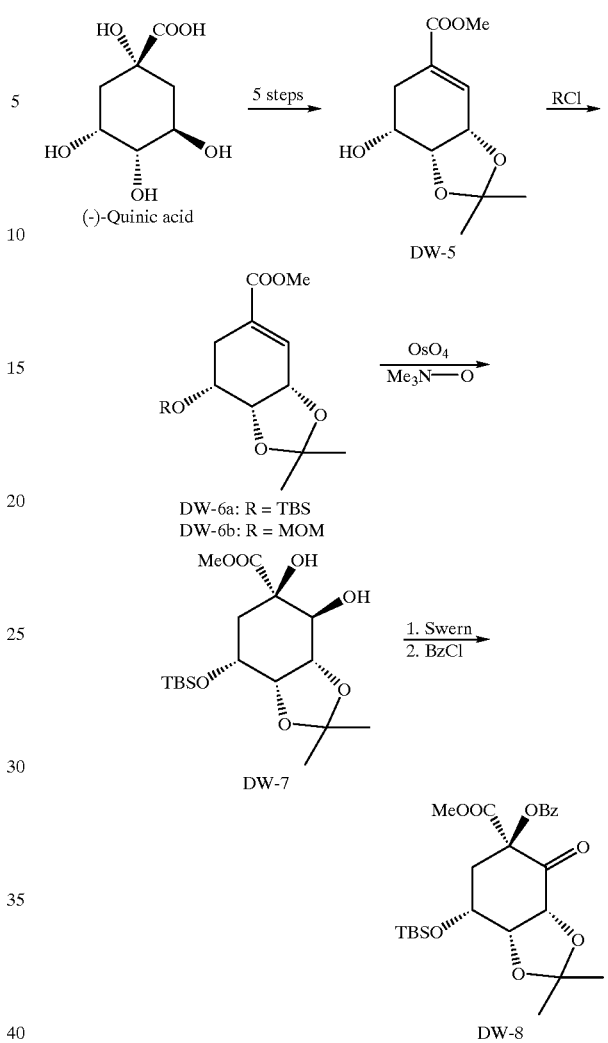

Preparation of Ketone DW-4

1,2:4,6-Di-O-isopropylidene-a-L-sorbofuranose (DW-3) was prepared based on a known procedure see: C-C. Chen et al, *Carbohydrate Research*, 1988, 175, 265–271.

To a solution of alcohol DW-3 (1.3 g, 5 mmol) in dry CH$_2$Cl$_2$ (10 mL) were added 3A molecular sieve powder (1.7 g) and PCC (2.2 g, 10 mmol). After being stirred at room temperature for 30 min, the reaction mixture was diluted with ether (50 mL), filtered through a glass funnel with a thin silica-gel layer, and washed with ether. The filtrate was concentrated and purified by flash chromatography (hexane:ethyl acetate, 2:1) to give a syrup (1 g) which was recrystallized from hexane to yield white crystals (0.8 g, 57%). mp 82–84 (C. $[a]_D 25=-48.4((c\ 0.71, CHCl_3)$. IR and NMR data showed DW-4 existed in hydrate form. IR (KBr): 3385, 1785 cm$^{-1}$. $^1$H NMR: $\delta$4.42 (d, J=9.6 Hz, 1), 4.35 (bs, 1H, OH), 4.13–3.90 (m, 5H), 3.61 (bs, 1H, OH), 1.54, 1.47, 1.44, 1.42 (s, each 3H). $^{13}$C NMR: $\delta$111.2, 111.2, 100.3, 98.24, 72.86, 71.16, 70.33, 60.91, 28.91, 26.5, 25.65, 19.52.

Preparation of DW-5

DW-5 was prepared based on a known procedure from (–)-Quinic acid with 5 steps. see: T. K. M. Shing et al, *Tetrahedron*, 1991, 47, 4571–4578. $^1$H NMR showed DW-5 was obtained a mixture of 2,3-O-isopropylidene and 1,2-O-isopropylidene with a ratio of 91.5:8.5. $^1$H NMR: $\delta$6.79 (t, J=3.0 Hz, 1H), 4.73 (m, 1H), 4.42 (dd, J=6.0, 2.7 Hz, 1H), 3.95 (m, 1H), 3.77 (s, 3H), 3.78 (s, 3H), 2.65 (dd, J=16.8, 5.4 Hz, 1H), 2.49 (ddt, J=16.8, 9.0, 2.2 Hz, 1H), 2.12 (d, J=7.5 Hz, 1H).1.41, 1.39 (s, each 3H).

Preparation of DW-6a

To a solution of DW-5 (1.1 g, 4.8 mmol), imidazole (0.65 g, 9.6 mmol), and a catalytic amount of DMAP in dry CH$_2$Cl$_2$ (20 mL) was added TBSCl (0.9 g, 6.0 mmol) at room temperature. After being stirred for 10 hours, the reaction mixture was quenched with aqueous NH$_4$Cl and extracted with CH$_2$Cl$_2$ (3×20 mL). The combined extracts were washed with water and brine, dried over Na$_2$SO$_4$, concentrated and purified by flash chromatography (hexane:ether, 10:1 to 5:1) to afford 2,3-O-isopropylidene (DW-6a, 1.2 g) and 1,2-O-isopropylidene (0.16 g). IR (KBr): 1721 cm$^{-1}$. $^1$H NMR $\delta$6.66 (m, 1H), 4.67 (m, 1H), 4.31 (d, J=5.1 Hz, 1H), 3.92 (ddd, J=9.6, 6.0, 2.1 Hz, 1H), 3.76 (s, 3H), 2.6–2.4 (m, 2H), 1.39, 1.34 (s, each 3H), 0.92 (s, 9H), 0.12 (s, 6H).

Preparation of DW-7

To a solution of DW-6a (1.0 g, 2.9 mmol), trimethylamine N-oxide dihydrate (0.6 g, 5.4 mmol), pyridine (1.8 mL), and water (0.3 mL) in t-BuOH (8 mL) was added $OsO_4$ (0.01 g, 0.039 mmol) under $N_2$. After refluxing for 10 hours, the reaction mixture was cooled, then quenched with saturated aqueous $Na_2SO_3$ (5 mL). The mixture was then passed through a short silica-gel column and eluted with ethyl acetate. The eluent was concentrated and redissolved in $CH_2Cl_2$. The resulting solution was washed with saturated aqueous $Na_2SO_3$ and water, dried over $Na_2SO_4$, and concentrated to afford DW-7 as white crystals, mp 127–129 C. IR (KBr): 3460, 3433, 1740 $cm^{-1}$. $^1H$ NMR: δ4.35 (ddd, J=10.8, 4.8, 3.9 Hz, 1H), 4.27 (t, J=3.9 Hz, 1H), 4.01 (m, 2H), 3.82 (s, 3H), 2.28 (dd, J=13.2, 10.8 Hz, 1H), 1.84 (ddd, J=13.2, 4.8, 1.2 Hz, 1), 1.6, 1.4 (s, each 3H), 0.91 (s, 9H), 0.095, 0.11 (s, each 3H).

Preparation of Ketone DW-8

To a stirred solution of DMSO (0.120 g, 1.6 mmol) in dry $CH_2Cl_2$ (0.5 mL) at −78 (C. under nitrogen was added dropwise oxalyl chloride (0.072 mL, 0.75 mmol). The mixture was stirred for 10 min, then removed from the cold bath for 3 min, and recooled to −78 (C. Alcohol DW-7 (0.19 g, 0.5 mmol) in dry $CH_2Cl_2$ (1.5 mL) was added in one portion and the mixture was stirred for 10 min. Triethylamine (0.34 mL, 2.5 mmol) was added, and the mixture was stirred for another 10 min, then slowly warmed to room temperature. The reaction mixture was quenched with saturated aqueous $NH_4Cl$, extracted with $CH_3Cl_2$, dried ($Na_2SO_4$), concentrated, and purified with flash chromatography (hexane:ethyl acetate, 5:1 to 2:1) to give the hydroxyl-ketone (0.115 g, 60%).

To a solution of the above hydroxyl-ketone (0.09 g, 0.24 mmol) in pyridine (1 mL) was added DMAP (0.005 g) and BzCl (0.2 mL). After being stirred at room temperature for 2 hours, the reaction mixture was quenched with saturated aqueous $NH_4Cl$, extracted with ether (4×10 mL), washed with water, brine, dried over $Na_2SO_4$, concentrated, and purified by flash chromatography (hexane;ethyl acetate, 8:1) to afford ketone DW-8 as a colorless syrup (0.096 g, 87%). IR (KBr): 1764, 1750 $cm^{-1}$. $^1H$ NMR: δ8.02 (m, 2H), 7.65 (m, 1H), 7.50 (m, 2H), 4.85 (d, J=6.0 Hz, 1H), 4.54 (ddd, J=6.0, 3.0, 1.5 Hz, 1H), 4.4 (ddd, J=10.2, 3.9, 3.0 Hz, 1H), 3.82 (s, 3H), 3.01 (dd, J=15.0, 10.2 Hz, 1H), 2.69 (ddd, J=15.0, 3.9, 1.5 Hz, 1H), 1.55, 1.4 (s, each 3H), 0.88 (s, 9H), 0.095, 0.072 (s, each 3H).

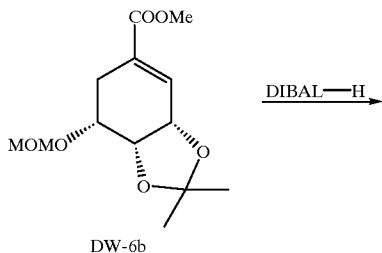

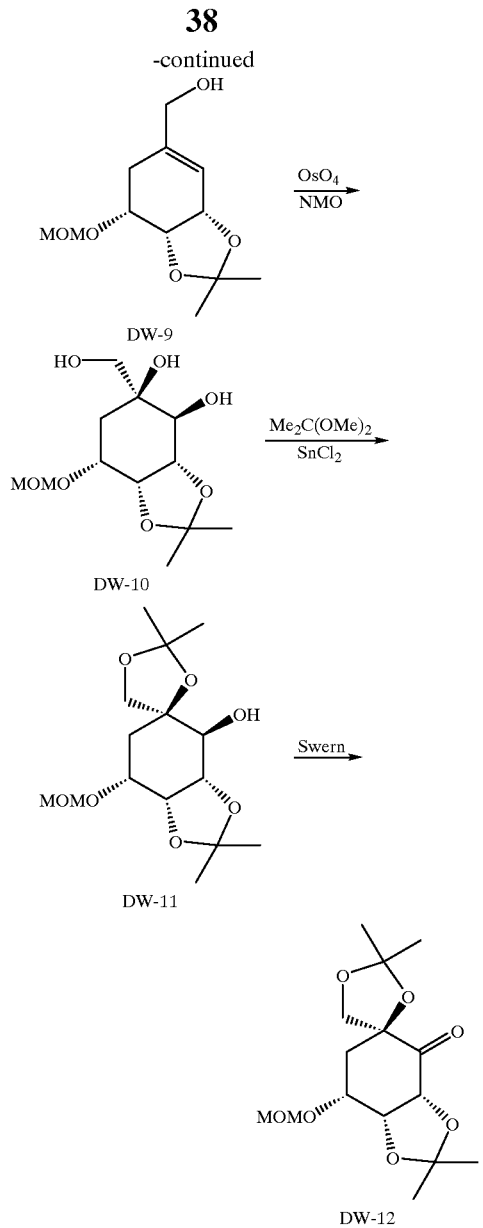

Preparation of DW-6b

To solution of alcohol DW-5 (10.3 g, 45.3 mmol) in dry $CH_2Cl_2$ (55 mL) were added i-$Pr_2NEt$ (12 mL), MOMCl (5.6 mL), and a catalytic amount of DMAP at 0 (C. After being stirred at room temperature overnight, the reaction mixture was quenched with saturated aqueous $NH_4Cl$, extracted with $CH_2Cl_2$, washed with water and brine, dried over $Na_2SO_4$, concentrated, and purified by flash chromatography (hexane:ethyl acetate, 4:1) to give DW-6b (10.4 g, 90%). $^1H$ NMR: δ6.72 (t, J=3.3 Hz, 1H), 4.8 (d, J=6.9 Hz, 1H), 4.75 (d, J=6.9 Hz, 1H), 4.74 (m, 1H), 4.49 (m, J=5.1 Hz, 1H), 3.89 (ddd, J=10.5, 5.5, 2.4 Hz, 1H), 3.78 (s, 3H), 3.42 (s, 3H), 2.76 (dd, J=16.8, 5.5 Hz, 1H), 2.48 (ddt, J=16.8, 10.5, 3.0 Hz, 1H), 1.42, 1.37 (s, each 3H).

Preparation of DW-9

To a solution of DW-6b (8.8 g, 32 mmol) in dry THF (10 mL) was added dropwise a solution of DIBAL-H (1.0 M in hexane, 70 mL) over 20 min at −15 (C. The mixture was stirred at 0 C. for 1 h, quenched with the saturated aqueous $NH_4Cl$, filtered, washed with ether, and concentrated to give DW-9 as a colorless syrup (7.9 g, 99%) which was pure enough for next step. $^1$H NMR δ5.57 (m, 1H), 4.74 (d, J=6.9 Hz, 1H), 4.70 (d, J=6.9 Hz, 1H), 4.63 (m, 1H), 4.43 (dd, J=5.4, 2.4 Hz, 1H), 3.99 (s, 2H), 3.83 (ddd, J=10.2, 5.4, 2.4 Hz, 1H), 3.37 (s, 3H), 2.34 (dd, J=15.6, 10.2 Hz, 1H), 2.23 (s, 1H, OH), 2.19 (dd, J=15.6, 5.4 Hz, 1H), 1.36, 1.35 (s, each 3H).

Preparation of DW-10

To a solution of DW-9 (7.8 g, 31 mmol), NMO (6.0 g, 51 mmol), pyridine (15 mL, 192 mmol), water (3 mL, 160 mmol) in t-BuOH (60 mL) was added OsO$_4$ (0.06 g) under nitrogen with stirring. After refluxing for 5 hours, the reaction mixture was cooled, quenched with saturated aqueous Na$_2$S$_2$O$_5$ (20 mL), and concentrated. The resulting residue was filtered through a short silica-gel filter and washed with ethyl acetate and CH$_2$Cl$_2$-EtOH (2:1). The filtrate was concentrated and the residue was recrystallized from hexane-CH$_2$Cl$_2$ to give DW-10 white crystals (6.8 g, 77%). mp 95–97 C. [a]$_D$25=−31.14((c 0.35, CHCl$_3$) $^1$H NMR: δ4.75 (d, J=6.9 Hz, 1H), 4.71 (d, J=6.9 Hz, 1H), 4.42 (t, J=4.5 Hz, 1H), 4.25 (dt, J=11.1, 4.5 Hz, 1H), 4.1 (dd, J=7.2, 4.5 Hz, 1H), 3.7 (d, J=7.2 Hz, 1H, OH), 3.66 (d, J=11.1 Hz, 1H), 3.49 (d, J=11.1 Hz, 1H), 3.39 (s, 3H), 1.89 (dd, J=13.5, 4.5 Hz, 1H), 1.75 (dd, J=13.5, 11.1 Hz, 1H), 1.53, 1.39 (s, each 3H). $^{13}$C NMR: δ110.0, 96.09, 80.27, 77.72, 75.58, 73.37, 70.51, 69.41, 55.66, 32.66, 28.35, 26.29. Anal. Calcd for C$_{12}$H$_{22}$O$_7$: C, 51.79; H, 7.77. Found: C, 51.88, H, 7.89.

Preparation of Ketone DW-12

To a suspension of DW-10 (1.38 g, 5 mmol) in 2,2-dimethoxypropane (20 mL) was added catalytic amount of CSA at 0 (C. with stirring. After being stirred at 0 (C. for 2 hours, the reaction mixture was slowly warmed to room temperature, and stirred at this temperature for another 2 hours. The reaction was quenched with triethylamine (0.2 mL), and diluted with water and ether. The aqueous solution was extracted with ether. The combined extracts were washed with water and brine, dried over Na$_2$SO$_4$, and concentrated to give a syrup which was used for next step without further purification.

To a solution of DMSO (0.69 g, 8.9 mmol) in dry CH$_2$Cl$_2$ (2 mL) was added dropwise oxalyl chloride (0.43 mL, 4.45 mmol) at −78 C. The solution was stirred at −78 C. for 10 min, then removed from cold bath for 3 min, and recooled to −78 (C. A solution of the above crude alcohol in dry CH$_2$Cl$_2$ (5 mL) was added. After the solution was stirred at −78 (C. for 1 hour, triethylamine (1.86 mL, 13.5 mmol) was added dropwise, and the resulting mixture was stirred at −78 (C. for 10 min, then warmed to room temperature. After the addition of saturated aqueous NH$_4$Cl (20 mL), the mixture was extracted with ether, washed with water and brine, dried over Na$_2$SO$_4$, concentrated and purified by flash chromatography (hexane:ethyl acetate, 5:1 to 2:1) to give ketone DW-12 as a light yellow oil, which was recrystallized from hexane to give white crystals (0.66 g, 42% from DW-11). mp 52–53 C. [a]$_D$25=−41.7((c 0.64, CH$_2$Cl$_2$). IR (KBr): 1743 cm$^{-1}$. $^1$H NMR: δ4.82 (d, J=5.1 Hz, 1H), 4.8 (d, J=6.9 Hz, 1H), 4.77 (d, J=6.9 Hz, 1H), 4.7 (dd, J=5.1, 3.3, 1.2 Hz, 1H), 4.67 (d, J=8.8 Hz, 1H), 4.5 (ddd, J=11.1, 5.4, 3.3 Hz, 1H), 3.61 (d, J=8.8 Hz, 1H), 3.43 (s, 3H), 2.25 (ddd, J=13.5, 5.4, 1.2 Hz, 1H), 2.17 (dd, J=13.5, 11.1 Hz, 1H), 1.48, 1.44, 1.43, 1.26 (s, each 3H). $^{13}$C NMR: δ204.1, 111.4, 111.1, 96.54, 83.17, 78.57, 77.87, 69.99, 68.42, 55.9, 36.65, 27.18, 27.08, 26.17 (2C). Anal. Calcd for C$_{15}$H$_{24}$O$_7$: C, 56.95; H, 7.65. Found: C, 57.14; H, 7.69.

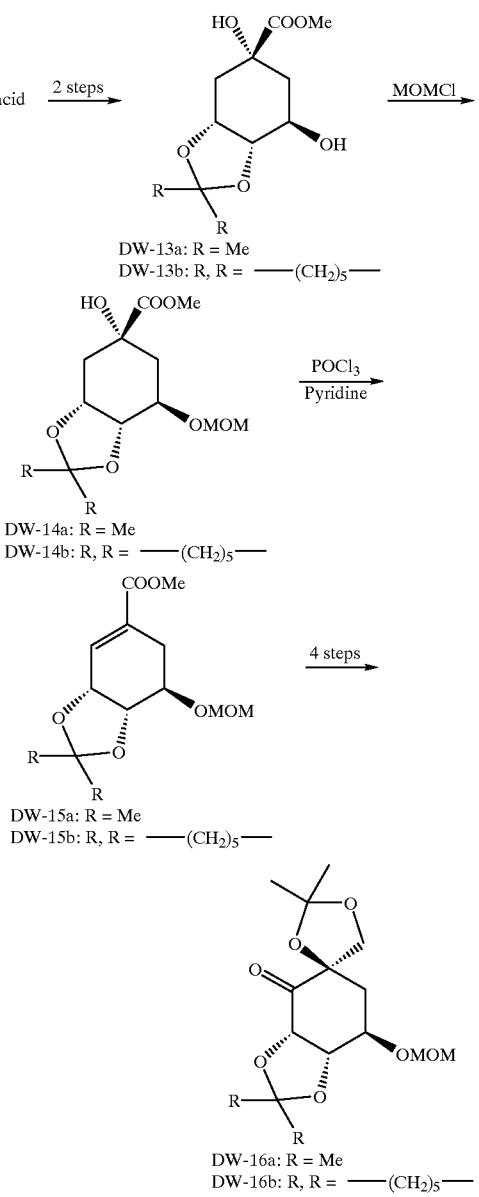

DW-13a: R = Me
DW-13b: R, R = —(CH$_2$)$_5$—

DW-14a: R = Me
DW-14b: R, R = —(CH$_2$)$_5$—

DW-15a: R = Me
DW-15b: R, R = —(CH$_2$)$_5$—

DW-16a: R = Me
DW-16b: R, R = —(CH$_2$)$_5$—

Preparation of DW-13a

To a suspension of (−)-Quinic acid (46 g, 0.239 mol) in 2,2-dimethoxypropane (60 mL) and benzene (180 mL) was added TsOH (0.1 g) After refluxing for 15 hours, the reaction mixture was cooled to room temperature and quenched with triethylamine (0.5 mL). The solvent was removed under reduced pressure, and the residue was treated with ethyl acetate (100 mL). After filtration, the filtrate was concentrated and recrystallized in hexane-ethyl acetate to yield a lactone as white needles (43 g, 83.8%). mp 137–138 (C. [a]$_D$25=−30.0((c 1.27, CHCl$_3$) IR (KBr): 3421, 1776, 1073 cm$^{-1}$. $^1$H NMR: δ4.73 (dd, J=6.0, 2.4 Hz, 1H), 4.50 (ddd, J=7.5, 6.0, 2.7 Hz, 1H), 4.31 (ddd, J=6.3, 2.4, 1.2 Hz, 1H), 2.83 (s, 1H), 2.66 (d, J=12.0 Hz, 1H), 2.37 (ddd, J=14.7, 7.5, 2.4 Hz, 1H), 2.31 (dddd, J=12.0, 6.3, 2.4, 1.2 Hz, 1H), 2.19 (dd, J=14.7, 2.7 Hz, 1H), 1.53 (s, 3H), 1.33 (s, 3H). $^{13}$C NMR: δ179.2, 109.9, 75.88, 72.21, 71.69, 71.62, 38.13, 34.42, 27.09, 24.44. Anal. Calcd for C$_{10}$H$_{14}$O$_5$: C, 56.07; H, 6.59. Found: C, 56.13; H, 6.30.

To a solution of the above lactone (13.4 g, 63.5 mmol) in MeOH (75 mL) was added MeONa (4.4 g, 81.5 mmol).

After being stirred at room temperature for 3 hours, AcOH (4.66 mL, 81.5 mmol) was added dropwise and the solvent was removed under reduce pressure. The resulting syrup was dissolved in ether (200 mL), filtered through a thin silica-gel, washed with ether and ethyl acetate,. concentrated, and purified by flash chromatography (hexane:ethyl acetate 3:1 to 1:2, V/V) to give alcohol DW-13a as a slightly yellow syrup (10.1 g, 82%) along with recoverd lactone (2 g). $[a]_D 25=-44.4((c\ 0.48, CHCl_3)$. IR (KBr): 3437, 1736 cm$^{-1}$. $^1$H NMR: δ4.43 (m, 1H), 4.1 (m, 1H), 3.95 (m, 1H), 3.77 (s, 3H), 2.22 (m, 2H), 2.03 (m, 1H), 1.81 (m, 1H), 1.51 (s, 3H), 1.33 (m, 1H). $^{13}$C NMR: δ175.7, 109.3, 80.19, 74.06, 73.53, 68.18, 53.16, 39.16, 34.91, 28.31, 25.81.

Preparation of DW-13b

DW-13b was prepared based on a reported procedure. see: T. K. M. Shing et al, *Tetrahedron*, 1990, 46, 6575–6584.
Preparation of DW-14a and 14b MOMCl (2.81 g, 35 mmol) was added dropwise to a solution of DW-13a (6.3 g, 25 mmol), i-Pr$_2$NEt (6.3 mL, 35 mmol), and catalytic amount of DMAP in CH$_2$Cl$_2$ (50 mL) at 0 (C. After being stirred at 0 (C. for 15 hours, the reaction mixture was quenched with saturated aqueous NH$_4$Cl, and extracted with CH$_2$Cl$_2$, washed with water and brine, dried (Na$_2$SO$_4$), and concentrated to give a yellow syrup which was used for next step without further purification.

DW-14b was prepared similarly from DW-13b with 95%.
Preparation of DW-15a and 15b POCl$_3$ (2.5 mL) was added to a solution of crude DW-14a in pyridine (50 mL) at 0 C. with stirring. After being stirred at room temperature for 3 hours, the reaction mixture was diluted with ether, and quenched with saturated aqueous NH$_4$Cl at 0° C. The aqueous layer was extracted with ether (4×30 mL), washed with water (3×50 mL), dried over Na$_2$SO$_4$, concentrated and purified by flash chromatography (hexane:ether, 2:1) to give DW-15a as a colorless syrup (3.7 g, 54% from DW-13a). $[a]_D 25=-34.4((c\ 0.57, CHCl_3)$.

DW-15b was prepared Similarly from DW-14b with 60% yield. $[a]_D 25=-47.8((c\ 0.41, CHCl_3)$. $^1$H NMR: δ6.91 (m, 1H), 4.74 (s, 2H), 4.73 (m, 1H), 4.2 (t, J=6.3 Hz, 1H), 3.97 (dd, J=6.7, 4.5 Hz, 1H), 3.77 (s, 3H), 3.39 (s, 3H), 2.73 (ddt, J=17.7, 4.5, 1.2 Hz, 1H), 2.35 (ddt, J=17.7, 6.7, 1.8 Hz, 1H), 1.7–1.5 (m, 8H, 1.4 (m, 2H).

Preparation of Ketone DW-16a and DW-16b

The synthesis of DW-16a was similar to the synthesis of DW-12 from DW-9. Colorless syrup. $[a]_D 25=-42.9((c\ 0.49, CH_2Cl_2)$. $^1$H NMR: δ4.73 (d, J=6.9 Hz, 1H), 4.64 (d, J=7.3 Hz, 1H), 4.62 (d, J=6.9 Hz, 1H), 4.57 (ddd, J=7.3, 4.2, 1.2 Hz, 1H), 4.34 (d, J=9.0 Hz, 1H), 3.8 (ddd, J=6.0, 4.2, 3.3 Hz, 1H), 3.78 (d, J=9.0 Hz, 1H), 3.34 (s, 3H), 2.44 (dd, J=15.2, 3.3 Hz, 1H), 2.29 (ddd, J=15.2, 6.0, 1.2 Hz, 1H), 1.5, 1.43, 1.4, 1.33 (s, each 3H). $^{13}$C NMR: δ203.7, 111.6, 111.4, 95.01, 82.18, 79.91, 77.53, 72.3, 70.79, 55.78, 37.32, 26.68, 26.49, 26.11, 24.72. Anal. Calcd for C$_{15}$H$_{24}$O$_7$: C, 56.95; H, 7.65. Found: C, 56.74; H, 7.49.

DW-16b was prepared similarly from DW-15b. Colorless syrup, $[a]_D 25=-38.82((c\ 0.76, CH_2Cl_2)$. IR (KBr): 1742 cm$^{-1}$. $^1$H NMR: δ4.77 (d, J=6.9 Hz, 1H), 4.66 (d, J=6.9 Hz, 1H), 4.63 (d, J=6.9 HZ, 1H), 4.59 (ddd, J=6.9, 3.9, 1.5 Hz, 1H), 4.38 (d, J=9.0 Hz, 1H), 3.86 (ddd, J=6.0, 3.9, 3.0 Hz, 1H), 3.83 (d, J=9.0 Hz, 1H), 3.37 (s, 3H), 2.49 (dd, J=15.0, 3.0 Hz, 1H), 2.32 (ddd, J=15.0, 6.0, 1.5 Hz, 1H), 1.8–1.3 (m, 8H), 1.47, 1.43 (s, each 3H). 1.4 (br, 2H). Anal. Calcd for C$_{18}$H$_{28}$O$_7$: C, 60.66; H, 7.92.
Found: C, 60.39; H, 7.76.

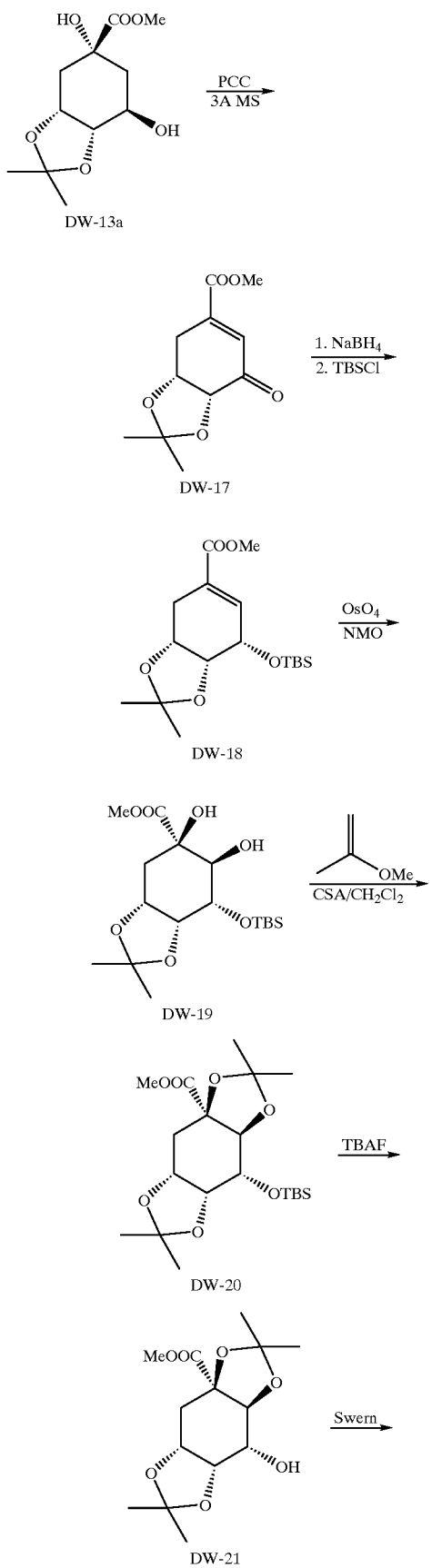

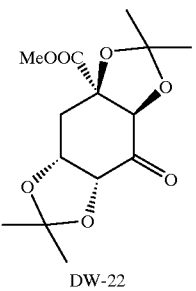

DW-22

Preparation of DW-17

PCC (25 g, 116 mmol) and powdered 3 A molecular sieve (17 g) were added to a solution of DW-13a (10 g, 40 mmol) and pyridine (10 mL) in dry $CH_2Cl_2$ (100 mL) After being stirred at room temperature for 24 hours, the reaction mixture was diluted with ether (300 mL), filtered through celite, and washed with ether. The filtrate was concentrated and purified with flash chraomatography (hexane:ethyl acetate, 3:1) to give enone DW-17 as white needles (5.5 g, 60%). mp 84–85 (C. $[a]_D25$=–51.7((c 0.5, $CHCl_3$). IR (KBr): 1725, 1688, 1631 $cm^{-1}$. $^1$H NMR: δ6.85 (dd, J=2.7, 0.9 Hz, 1H), 4.70 (ddd, J=5.1, 5.1, 1.8 Hz, 1H), 4.31 (d, J=5.1 Hz, 1H), 3.86 (s, 3H), 3.22 (ddd, J=20.4, 1.8, 0.9, 1H), 2.88 (ddd, J=20.4, 5.1, 2.8, 1H), 1.41, 1.32 (s, each 3H). $^{13}$C NMR: δ197.6, 166.4, 144.4, 131.5, 109.8, 75.31, 72.73, 53.06, 27.57, 26.86, 26.05.

Anal. Calcd for $C_{11}H_{14}O_5 \cdot 0.1H_2O$: C, 57.94; H, 6.23; Found: C, 57.74; H, 6.10.

Preparation of DW-18

$NaBH_4$ (1.0 g, 26 mmol) was added portionwise to a solution of enone DW-17 (5 g, 22.1 mmol) in MeOH (30 mL). After being stirred at room temperature for 0.5 hour, the reaction mixture was quenched with saturated aqueous $NH_4Cl$ (15 mL). After the removal of MeOH under reduced pressure, the resulting aqueous solution was extracted with $CH_2Cl_2$ (4(15 mL), washed with brine, dried over $Na_2SO_4$, and concentrated to give an allylic alcohol as a white solid (5 g, 98%) which was used for next step without further purification.

To a solution of the above allylic alcohol (3.2 g, 0.014 mol), Imidazole (1.7 g, 0.025 mol) and catalytic amount of DMAP in dry $CH_2Cl_2$ (50 mL), was added tert-butyldimethylsilyl chloride (3.0 g, 0.02 mol). After being stirred at room temperature for 2 hours, the reaction mixture was quenched with saturated aqueous $NH_4Cl$, extracted with ether (3 (30 mL), washed with water and brine, dried over $NaSO_4$, concentrated and purified with flash chromatography (hexane:ether, 5:1, V/V) to give DW-18 as acolorless syrup (4.6 g, 96%). $[a]_D25$=+17.9((c 0.9, $CHCl_3$). IR (KBr): 1719, 1644 $cm^{-1}$. $^1$H NMR: δ6.91 (m, 1H), 4.55 (ddd, J=7.2, 4.5, 1.8 Hz, 1H), 4.44 (ddd, J=7.2, 3.7, 1.5 Hz, 1H), 4.16 (dt, J=3.7, 1.9 Hz, 1H), 3.76 (s, 3H), 2.98 (dd, J=16.3, 1.8 Hz, 1H), 1.89 (dddd, J=16.3, 4.5, 2.4, 2.1 Hz, 1H), 1.42 (s, 3H), 1.40 (s, 3H), 0.94 (s, 9H), 0.144 (s, 6H). $^{13}$C NMR: δ166.3, 143.9, 128.2, 109.0, 78.07, 73.21, 70.63, 52.03, 27.67, 26.19, 25.86, 24.49, 18.68, –4.326, –4.349.

Preparation of DW-19

$OsO_4$ (10 mg) was added to a solution of DW-18 (4.6 g, 13.5 mmol), NMO (2.8 g, 24 mmol), pyridine (7 mL), and water (1.4 mL) in t-BuOH (45 mL) at room temperature under $N_2$. The solution was refluxed under $N_2$ for 3 hours, then cooled to room temperature, and quenched with saturated aqueous $Na_2S_2O_5$ (15 mL). Upon removing the solvent under reduced pressure, the residue was purified by flash chromatography (hexane:ether, 1:1, V/V) to afford diol DW-19 as a colorless syrup (4.8 g, 95%). IR (KBr): 3475, 1740 $cm^{-1}$. $^1$H NMR: δ4.33 (m, 2H), 4.18–4.04 (m, 2H), 3.81 (s, 3H), 3.37 (br, 1H), 2.25 (br, 1H), 2.0 (m, 2H), 1.54 (s, 3H), 1.34 (s, 3H), 0.93 (s, 9H), 0.15 (s, 3H), 0.14 (s, 3H). $^{13}$C NMR δ174.4, 109.8, 77.39, 76.95, 72.93, 72.63, 71.36, 53.34, 36.38, 28.82, 26.22, 26.02, 18.42, –4.237, –4.266.

Preparation of DW-20

To a solution of diol DW-19 (4.8 g, 12.8 mmol) and 2-methoxypropene (8 mL) in dry $CH_2Cl_2$ (80 mL) was added catalytic amount of CSA under $N_2$ at room temperature. The resulting solution was stirred for 2 hours, then quenched with triethylamine (0.5 mL). Upon removing the solvent, the resulting residue was purified by flash chromatography (hexane:ether, 10:1 to 5:1. the silica-gel was pre-buffered with 1% triethylamine in hexane) to afford DW-20 as a colorless syrup (5.0 g, 94%). $[a]_D25$=–15.0((c 0.66, $CHCl_3$). IR (KBr): 1741 $cm^-$. $^1$H NMR: δ4.76 (d, J=3.6 Hz, 1H), 4.40 (dt, J=7.8, 7.5 Hz, 1H), 4.31–4.24 (m, 2H), 3.78 (s, 3H), 2.35 (br, 2H), 1.48, 1.44, 1.34, 1.29 (s, each 3H), 0.91 (s, 9H), 0.13, 0.11 (s, each 3H). $^{13}$C NMR: δ173.6, 110.2, 108.3, 82.6, 78.26, 72.81, 70.43, 68.9, 52.83, 34.03, 28.86, 26.21, 26.03, 24.83, 24.14, 18.3, –4.334, –4.94.

Preparation of DW-21

DW-20 (1.6 g, 3.9 mmol) was dissolved in a solution of TBAF in THF (1M, 15 mL). After being stirred at room temperature for 1 hour, the reaction mixture was quenched with saturated aqueous $NH_4Cl$, extracted with ether (3(20 mL), washed with water and brine, dried ($NaSO_4$), concentrated and purified by flash chromatography (hexane:ether, 2:1 to 1:1, V/V) to give DW-21 as white crystals (0.82 g, 70%). $[a]_D25$=–20.5((c 0.22, $CHCl_3$). IR (KBr): 3488, 1740 $cm^{-1}$. $^1$H NMR: δ4.93 (d, J=4.8 Hz, 1H), 4.45 (ddd, J=7.8, 7.8, 5.1 Hz, 1H), 4.37 (dd, J=7.8, 3.6 Hz, 1H), 4.14 (ddd, J=4.8, 3.6, 2.4 Hz, 1H), 3.81 (s, 3H), 2.56 (d, J=2.4 Hz, 1H, OH), 2.40 (dd, J=13.8, 7.8 Hz, 1H), 2.24 (dd, J=13.8, 5.1 Hz, 1H), 1.48, 1.45, 1.36, 1.30 (s, each 3H). $^{13}$C NMR: δ173.4, 110.3, 108.7, 82.07, 76.88, 72.94, 70.62, 68.57, 53.07, 33.88, 27.24, 26.07, 24.98, 23.96.

Preparation of Ketone DW-22

To a solution of DMSO (0.53 g, 6.7 mmol) in dry $CH_2Cl_2$ (2 mL) was added dropwise oxalyl chloride (0.29 mL, 3.3 mmol) under $N_2$ at –78 (C. The mixture was stirred at –78 (C. for 10 min, then removed from coolant and stirred for 3 min. Upon recooling to –78 C., a solution of alcohol DW-21 (0.67 g, 2.2 mmol) in dry $CH_2Cl_2$ (7 mL) was added in one portion. The resulting reaction mixture was stirred at –78 (C. for additional 1 hour, then triethylamine (1.4 mL) was added dropwise. After being stirred at –78 (C. for an another 10 mi, the reaction mixture was warmed to room temperature, quenched with saturated aqueous $NH_4Cl$ (5 mL), extracted with $CH_2Cl_2$ (3(20 mL), washed with water and brine, dried ($NaSO_4$), concentrated, and purified by flash chromatography (hexane:ether, 1:1 to 1:2, V/V) to give ketone DW-22 as a white solid (0.66 g, 99%). mp 66–68 (C. (hexane). $[a]_D25$=–1.9((c 0.68, $CHCl_3$). IR (KBr): 3481(hydrate), 1749 $cm^{-1}$. Ketone: $^1$H NMR: δ4.92 (s, 1H), 4.90 (dd, J=8.4, 0.7 Hz, 1H), 4.85 (ddd, J=8.5, 8.4, 3.9 Hz, 1H), 3.81 (s, 3H), 2.25 (ddd, J=14.4, 3.9, 0.7 Hz, 1H), 2.0 (dd, J=14.4, 8.5 Hz, 1H), 1.56, 1.49, 1.35, 1.34 (s, each 3H). $^{13}$C NMR: δ202.4, 171.4, 113.6, 110.9, 85.1, 79.9, 77.29, 73.42, 53.34, 36.12, 26.71, 26.33, 24.97, 24.35. Hydrate: $^1$H NMR: δ4.81 (s, 1H), 4.50 (ddd, J=8.8, 7.8, 5.1 Hz, 1H), 4.35 (d, J=7.8 Hz, 1H), 3.80 (s, 3H), 2.31 (dd, J=13.8, 5.1 Hz, 1H), 2.18 (dd, J=13.8, 8.8 Hz, 1H), 1.483, 1.481, 1.36, 1.33 (s, each 3H). $^{13}$C NMR: δ172.7, 110.5, 109.6, 93.73, 82.5, 79.51, 76.01, 71.64, 53.14, 33.94, 26.86, 26.33, 24.69, 24.26. Anal. Calcd for $C_{14}H_{20}O_7 \cdot 0.2H_2O$: C, 55.33; H, 6.77. Found: C, 55.35; H, 6.64.

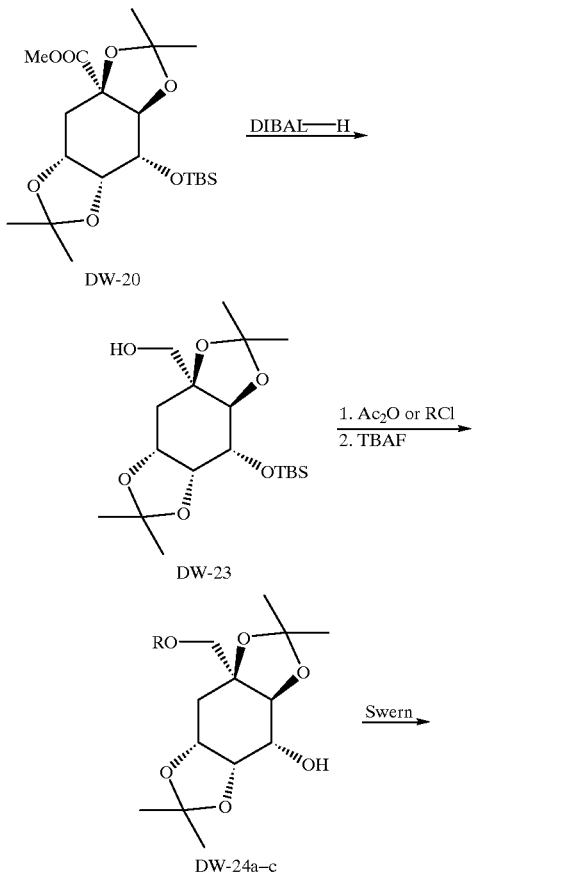

a R = Ac
b R = Bz
c R = Ts

Preparation of DW-23

DIBAL-H (1.0 M in Hexane, 30 mL, 0.03 mol) was added dropwise to a solution of DW-20 (5.0 g, 0.0121 mol) in dry THF (30 mL) at −20 (C. under $N_2$ over 30 min. After being stirred at 0 (C. for 2 hours, the reaction mixture was quenched with saturated aqueous $NH_4Cl$ (10 mL) and filtered. The cake was washed with ether. The filtrate was extracted with ether, washed with brine, dried ($NaSO_4$), concentrated and purified by flash chromatography (hexane:ether, 2:1, V/V) to give DW-23 as a colorless syrup (4.3 g, 92.3%). $[a]_D25=-3.8$((c 0.29, $CHCl_3$) IR (KBr): 3484 $cm^{-1}$. $^1H$ NMR: δ4.43 (t, J=4.5 Hz, 1H), 4.38 (ddd, J=9.9, 7.8, 5.4 Hz, 1H), 4.32 (dd, J=7.8, 4.5 Hz, 1H), 4.13 (d, J=4.5 Hz, 1H), 3.64 (dd, J=11.4, 6.6 Hz, 1H), 3.59 (dd, J=11.4, 6.6 Hz, 1H), 2.10 (dd, J=13.8, 5.4 Hz, 1H), 2.06 (t, J=6.6 Hz, 1H, OH), 1.85 (dd, J=13.8, 9.9 Hz, 1H), 1.48, 1.43, 1.40, 1.34 (s, each 3H), 0.90 (s, 9H), 0.11 (s, 6H). $^{13}C$ NMR δ109.3, 108.2, 83.72, 77.81, 73.13, 71.19, 69.02, 68.51, 34.61, 27.74, 26.87, 26.65, 26.14, 24.24, 18.43, −4.311, −4.888. Anal. calcd for $C_{19}H_{36}O_6Si$: C, 58.73; H, 9.33. Found: C, 58.84; H, 9.11.

Preparation of DW-24a

Acetic anhydride (0.4 mL, 4.2 mmol) was added to a solution of DW-23 (0.9 g, 2.33 mol), triethylamine (0.9 mL, 5.03 mmol), and catalytic amount of DMAP in dry $CH_2Cl_2$ (5 mL). After being stirred at room temperature for 2 hours, the reaction mixture was quenched with saturated aqueous $NH_4Cl$, extracted with $CH_2Cl_2$ (3(20 mL), washed with water and brine, dried over $NaSO_4$, and concentrated to give a colorless syrup which was used for next step directly.

The above crude acetate was dissolved in a solution of TBAF in THF (1 M, 8 mL). After being stirred at room temperature for 2 hours, the reaction mixture was quenched with saturated aqueous $NH_4Cl$, extracted with $CH_2Cl_2$ (4(15 mL), washed with water and brine, dried ($NaSO_4$), concentrated and purified by flash chromatography (hexane:ethyl acetate, 5:1 to 2:1, V/V) to afford DW-24a as white crystals (0.58 g, 86%). $[a]_D25=+7.4$((c 0.27, $CHCl_3$). IR (KBr): 3487, 1743 $cm^{-1}$. $^1H$ NMR: δ4.45–4.31 (m, 3H), 4.26 (d, J=4.5 Hz, 1H), 4.19 (d, J=11.6 Hz, 1H), 4.11 (d, J=11.6 Hz, 1H), 2.61 (s, 1H, OH), 2.08 (s, 3H), 2.12 (m, 1H), 1.88 (m, 1H), 1.48, 1.41, 1.39, 1.36 (s, each 3H). $^{13}C$ NMR: δ170.9, 109.8, 108.7, 81.36, 76.58, 72.84, 71.13, 69.74, 67.22, 34.39, 27.96, 26.83, 26.53, 24.46, 21.08. Anal. Calcd for $C_{15}H_{24}O_7$: C, 56.95; H, 7.64. Found: C, 57.13; H, 7.24.

Preparation of Ketone DW-25a

To a solution of DMSO (0.41 g, 5.2 mmol) in dry $CH_2Cl_2$ (1.5 mL) was added dropwise oxalyl chloride (0.226 mL, 0.0026 mol) under $N_2$ at −78 (C. The mixture was stirred at −78 (C. for 10 min, then removed from coolant and stirred for 3 min. Upon recooling to −78 (C., a solution of alcohol DW-24a (0.54 g, 0.00172 mol) in dry $CH_2Cl_2$ (5 mL) was added in one portion. After the mixture was stirred at −78 (C. for additional 1 hour, triethylamine (1.1 mL) was added dropwise. The resulting mixture was stirred at −78 (C. for an another 10 min, and warmed to room temperature. The reaction mixture was quenched with saturated aqueous $NH_4Cl$ (4 mL), extracted with $CH_2Cl_2$ (3(15 mL), washed with water and brine, dried over $NaSO_4$, concentrated and purified by flash chromatography (hexane:ether, 2:1 to 1:2, V/V) to give ketone DW-25a as a white solid (0.53 g, 95%) mp 72.5–74 (C. (recrystallized from hexane). $[a]_D25=+11.2$ ((c 0.34, $CHCl_3$). IR (KBr): 3464 (hydrate), 1748 $cm^{-1}$. Ketone: $^1H$ NMR: δ5.01 (dd, J=8.4, 0.6 Hz, 1H), 4.90 (ddd, J=10.2, 8.4, 4.5 Hz, 1H), 4.34 (s, 1H), 4.24, 4.04 (d, J=11.7, each 1H), 2.16 (ddd, J=14.1, 4.5, 0.6 Hz, 1H), 2.08 (s, 3H), 1.45 (dd, J=14.1, 10.2 Hz, 1H), 1.55, 1.50, 1.39, 1.36 (s, each 3H). $^{13}C$ NMR: δ203.3, 170.6, 112.9, 110.5, 84.33, 81.09, 77.74, 73.28, 67.55, 36.78, 27.04, 26.98, 26.15, 24.56, 20.89. Hydrate: $^1H$ NMR: δ4.50 (ddd, J=10.6, 7.5, 5.7 Hz, 1H), 4.41 (d, J=7.5 Hz, 1H), 4.25, 4.05 (d, J=11.5 Hz, each 1H), 4.11 (s, 1H), 2.08 (dd, J=13.5, 5.7 Hz, 1H), 2.09 (s, 3H), 1.60 (dd, J=13.5, 10.6 Hz, 1H), 1.50, 1.45, 1.40, 1.39 (s, each 3H). $^{13}C$ NMR δ170.8, 110.5, 109.7, 94.12 (hydrate C), 81.9, 80.11, 76.33, 72.0, 68.87, 34.69, 27.46, 27.24, 26.03, 25.04, 21.05. Anal. Calcd for $C_{15}H_{22}O_7 \cdot 0.8H_2O$: C, 54.80; H, 7.10. Found: C, 54.79; H, 7.03.

Preparation of DW-24b

Benzoyl chloride (0.3 mL, 2.5 mmol) was added to a solution of alcohol DW-23 (0.77 g, 2 mmol), triethylamine (0.5 mL), and catalytic amount of DMAP in dry $CH_2Cl_2$ (5 mL). After being stirred at room temperature for 2 hours, the reaction mixture was quenched with saturated aqueous $NH_2Cl$, extracted with $CH_2Cl_2$ (3×20 mL), washed with water and brine, dried over NaSO$_4$, and concentrated to give a crude benzoate.

The above crude benzoate was dissolved in a solution of TBAF in THF (1 M, 8 mL). After being stirred at room temperature for 1 hour, the reaction mixture was quenched with saturated aqueous NH$_4$Cl, extracted with ether, washed with water and brine, dried (NaSO$_4$), concentrated and purified by flash chromatography (hexane:ethyl acetate, 2;1, V/V) to give DW-24b as a colorless syrup (0.75 g, 99%). IR (KBr): 3508, 1723 cm$^{-1}$. $^1$H NMR: δ8.08 (m, 2H), 7.55 (m, 1H), 7.43 (m, 2H), 4.52–4.35 (m, 6H), 2.68 (s, 1H, OH), 2.26 (dd, J=14.1, 5.4 Hz, 1H), 2.06 (dd, J=14.1, 8.7 Hz, 1H), 1.51, 1.43, 1.42, 1.39 (s, each 3H). $^{13}$C NMR: δ166.5, 133.2, 130.2, 130.0, 128.5, 109.8, 108.7, 81.57, 76.92, 72.91, 71.19, 70.23, 67.38, 34.57, 27.98, 26.79, 26.70, 24.38.

Preparation of Ketone DW-25b

To a solution of DMSO (0.453 g, 5.8 mmol) in dry CH$_2$Cl$_2$ (2 mL) was added dropwise oxalyl chloride (0.254 mL, 2.9 mmol) under N$_2$ at –78 (C. The mixture was stirred at –78 (C. for 10 min, then removed from coolant and stirred for 3 min. Upon recooling to –78 (C., a solution of alcohol DW-25b (0.73 g, 1.93 mmol) in dry CH$_2$Cl$_2$ (6 mL) was added in one portion. After the mixture was stirred at –78 (C. for additional 1 hour, triethylamine (1.1 mL) was added dropwise. The resulting mixture was stirred at –78 (C. for an another 10 min, warmed to room temperature, quenched with saturated aqueous NH$_4$Cl (4 mL), extracted with CH$_2$Cl$_2$ (3(20 mL), washed with water and brine, dried over NaSO$_4$, concentrated and purified by flash chromatography (hexane:ether, 2:1 to 1:2, V/V) to give ketone DW-25b as a colorless syrup (0.71 g, 96%). [a]$_D$25=+21.0((c 0.84, CHCl$_3$). IR (KBr): 3468 (hydrate), 1749, 1724 cm$^{-1}$. $^1$H NMR: δ8.04 (m, 2H), 7.57 (m, 1H), 7.45 (m, 2H), 5.07 (d, J=8.4 Hz, 1H), 4.94 (ddd, J=10.2, 8.4, 4.5 Hz, 1H), 4.50 (s, 1H), 4.42 (d, J=11.4 Hz, 1H), 4.36 (d, J=11.4 Hz, 1H), 2.27 (dd, J=14.4, 4.5 Hz, 1H), 1.60 (dd, J=14.4, 10.2 Hz, 1H), 1.58, 1.52, 1.41, 1.39 (s, each 3H). $^{13}$C NMR: δ203.3, 166.1, 133.6, 130.0, 129.9, 128.7, 113.0, 110.5, 84.45, 81.45, 77.72, 73.33, 68.42, 36.93, 27.01, 27.0, 26.2, 24.56. Anal. Calcd for C$_{20}$H$_{24}$O$_7$.H$_2$O: C, 60.91; H, 6.64. Found: C, 60.85; H, 6.25.

Preparation of DW-24c

TsCl (0.475 g, 2.5 mmol) was added to a solution of DW-23 (0.77 g, 2 mmol), pyridine (0.5 mL), and catalytic amount of DMAP in dry CH$_2$Cl$_2$ (5 mL) at 0 (C. After being stirred at room temperature for 30 hours, the reaction mixture was quenched with saturated aqueous NH,CL, extracted with CH$_2$Cl$_2$ (3 (20 mL), washed with water and brine, dried over NaSO$_4$, and concentrated to give the crude compound.

The above crude compound was dissolved in a solution of TBAF in THF (1 M, 10 mL). After being stirred at room temperature for 1 hour, the reaction mixture was quenched with saturated aqueous NH$_4$Cl, extracted with ether, washed with water and brine, dried (NaSO$_4$), concentrated, and purified by flash chromatography (hexane:ethyl acetate, 2:1, V/V) to give DW-24c as white crystals (0.7 g, 82%). [a]$_D$25=+3.1((c 0.89, CHCl$_3$). IR (KBr): 3446, 1176, 1063, 986 cm$^{-1}$. $^1$H NMR: δ7.81 (d, J=8.4 Hz, 2H), 7.35 (d, J=8.4 Hz, 2H), 4.42–4.34 (m, 2H), 4.29 (dd, J=5.1, 4.5 Hz, 1H), 4.22 (d, J=5.1 Hz, 1H), 4.09 (d, J=10.2 Hz, 1H), 4.03 (d, J=10.2 Hz, 1H), 2.55 (s, 1H, OH), 2.45 (s, 3H), 2.03 (m, 1H), J=10.2 Hz, 1H), 1.79 (m, 1H), 1.44, 1.39, 1.35, .31 (s, each 3H). $^{13}$C NMR: δ145.1, 130.0, 128.3, 128.3, 110.3, 108.8, 80.97, 77.60, 76.11, 74.22, 72.79, 70.95, 67.23, 34.1, 28.06, 26.72, 26.48, 24.42, 21.84. Anal. Calcd for C$_{20}$H$_{28}$O$_8$S: C, 56.06; H. 6.59. Found: C, 55.98; H, 6.61.

Preparation of Ketone DW-25c

To a solution of DMSO (0.375 g, 4.8 mmol) in dry CH$_2$Cl$_2$ (1.5 mL) was added dropwise oxalyl chloride (0.21 mL, 2.4 mmol) under N$_2$ at –78 (C. The mixture was stirred at –78 (C. for 10 min, then removed from coolant and stirred for 3 min. Upon recooling to –78 (C., a solution of alcohol DW-24c (0.67 g, 1.55 mol) in dry CH$_2$Cl$_2$ (4.5 mL) was added in one portion. After the mixture was stirred at –78 (C. for 1 hour, triethylamine (1.05 mL) was added dropwise. The resulting mixture was stirred at –78° C. for an another 10 min, warmed to room temperature, quenched with saturated aqueous NH$_4$Cl (4 mL), extracted with CH$_2$Cl$_2$ (3 (15 mL), washed with water and brine, dried over NaSO$_4$, concentrated, and purified by flash chromatography (hexane:ethyl acetate, 5:1 to 1:1, V/V) to give ketone DW-25c as a colorless syrup (0.67 g, 100%). [a]$_D$$^{25}$=+4.3((c 0.81, CHCl$_3$). IR (KBr): 3480 (hydrate), 1749, 1177, 990 cm$^{-1}$. $^1$H NMR: δ(7.79 (d, J=8.4 Hz, 2H), 7.35 (d, J=8.4 Hz, 2H), 4.91 (d, J=8.1 Hz, 1H), 4.81 (ddd, J=9.3, 8.1, 4.2 Hz, 1H), 4.33 (s, 1H), 4.07 (d, J=10.2 Hz, 1H), 4.02 (d, J=10.2 Hz, 1H), 2.44 (s, 3H), 2.07 (dd, J=14.4, 4.2 Hz, 1.48 (dd, J=4.4, 9.3 Hz, 1H) 1.49, 1.45, 1.34, 1.31 (s, each 3H). $^{13}$C NMR: δ202.9, 145.5, 130.2, 130.0, 128.2, 113.3, 110.7, 83.95, 80.13, 77.57, 73.25, 71.91, 36.04, 27.21, 26.73, 26.26, 24.38, 21.81.

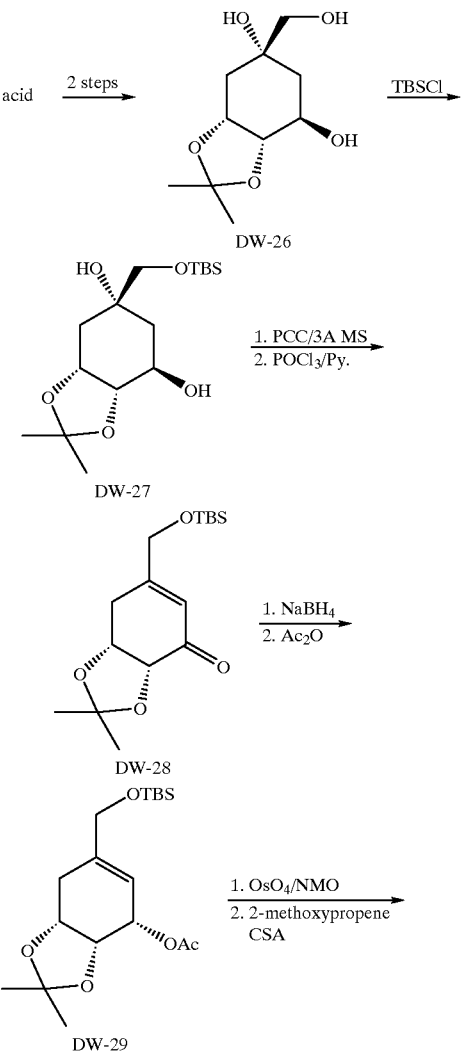

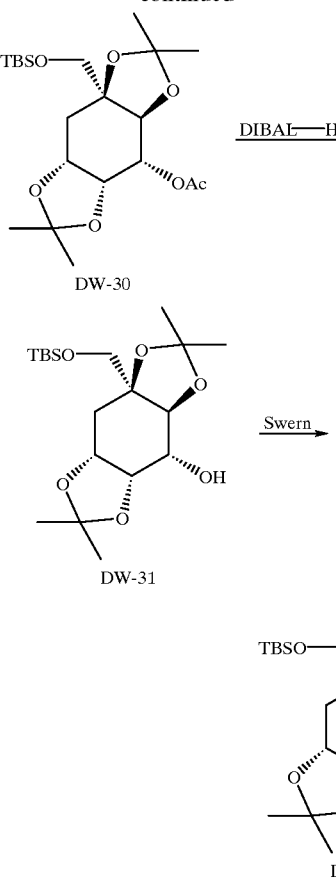

DW-30

DW-31

DW-32

Preparation of DW-26

After the lactone (6.2 g, 29.4 mmol) prepared from (−)-Quinic acid (see the preparation of DW-13a) was dissolved in EtOH (120 mL), NaBH$_4$ (4 g) was added. After being stirred at room temperature for 15 hours, saturated aqueous NaCl (50 mL) was added, and the mixture was stirred for an another 15 hour. Upon removing EtOH and water under reduced pressure, the resulting solid was extracted with CH$_2$Cl$_2$/MeOH (2/1, V/V). The extracts was concentrated and the residue was recrystallized from EtOH to give triol DW-26 as white crystals (6.2 g, 98%). $^1$H NMR: δ4.48 (ddd, J=6.0, 3.7, 2.7 Hz, 1H), 4.08 (m, 1H), 3.97 (t, J=6.0 Hz, 1H), 3.5–3.3 (m, 2H), 3.06, 2.82, 2.05 (bs, each 1H, OH), 2.24 (ddd, J=15.9, 2.7, 2.1 Hz, 1H), 2.0 (ddd, J=13.5, 4.5, 2.1 Hz, 1H), 1.85 (dd, J=15.9, 3.7 Hz, 1H), 1.54, 1.37 (s, each 3H), 1.49 (dd, J=13.5, 10.2 Hz, 1H). $^{13}$C NMR: δ109.3, 80.36, 74.43, 72.71, 70.38, 68.98, 38.41, 33.33, 28.41, 25.78.

Preparation of DW-27

To a solution of triol DW-26 (4.1 g, 18.8 mmol), imidazole (1.9 g, 33 mmol), and catalytic amount of DMAP in dry CH$_2$Cl$_2$ (50 mL) was added portionwise tert-butyldimethylsilyl chloride (3.5 g, 23 mmol) at 0 C. After being stirred at 0 (C. for 2 hours, the reaction mixture was diluted with ether (100 mL), filtered through a thin silica-gel, and washed with ether (200 mL). The filtrate was concentrated to give DW-27 as a colorless oil (5.5 g), which was used for next step directly. [a]$_D$25=38.0((c 0.5, CHCl$_3$). $^1$H NMR: δ4.50 (m, 1H), 4.03–3.94 (m, 2H), 3.42 (d, J=9.3 Hz, 1H), 3.36 (d, J=9.3 Hz, 1H), 3.01 (br, 2H, OH), 2.07 (dd, J=15.6, 3.6 Hz, 1H), 2.03–1.94 (m, 2H), 1.75 (m, 1H), 1.52, 0.35 (s, each 3H), 0.90 (s, 9H), 0.08 (s, 6H). $^{13}$C NMR: δ108.8, 78.9, 73.96, 71.77, 70.66, 68.28, 38.55, 33.47, 27.94, 26.05, 25.23, 18.47, −5.34.

Preparation of DW-28

After the crude DW-27 (5.5 g) was dissolved in CH$_2$Cl$_2$ (100 mL), powdered 3A MS (7 g), PCC (9 g, 41.7 mmol), and pyridine (5 mL) were added. After being stirred at room temperature overnight, the reaction mixture was diluted with ether (300 mL), filtered through thin silica-gel, and washed with ether. The filtrate was concentrated to give a colorless syrup. After the syrup was dissolved in pyridine (20 mL), the POCl$_3$ (2 mL) was added, the reaction mixture was stirred at room temperature for 16 hours, quenched with saturated aqueous NH$_4$Cl and ether, extracted with ether (3×50 mL), washed with water and brine, dried over NaSO$_4$, concentrated, purified by flash chromatography (hexane:ethyl acetate, 4:1, V/V) to afford enone DW-28 as a colorless syrup (3.1 g, 54% yield from DW-26). [a]$_D$25=−40.9((c 1.5, CHCl$_3$). IR (KBr): 1680, 1650 cm$^{-1}$. $^1$H NMR: δ6.25 (m, 1H), 4.64 (m, 1H), 4.28 (d, J=5.1 Hz, 1H), 4.23 (br, 2H), 2.67 (br, 2H), 1.40, 1.34 (s, each 3H), 0.90 (s, 9H), 0.078 (s, 6H). $^{13}$C NMR: δ196.2, 160.4, 121.8, 109.6, 75.7, 72.83, 65.21, 27.97, 27.62, 26.22, 25.96, 18.46, −5.287, −5.319.

Preparation of DW-29

To a solution of enone DW-28 (1.1 g, 3.4 mmol) in EtOH (10 mL) was added NaBH$_4$ (0.3 g, 7.6 mmol). After being stirred at room temperature for 2 hours, the reaction mixture was quenched with saturated aqueous NH$_4$Cl (10 mL), extracted with CH$_2$Cl$_2$ (5×20 mL), washed with water, and brine, dried (NaSO$_4$), and concentrated to give a crude alcohol.

After the above crude alcohol was dissolved in dry CH$_2$Cl$_2$ (10 mL), pyridine (0.7 mL), acetic anhydride (0.7 mL), and catalyst amount of DMAP were added. After being stirred at room temperature for 10 hours, the reaction mixture was quenched with saturated aqueous NH$_4$Cl, extracted with CH$_2$Cl$_2$ (3(20 mL), washed with water and brine, dried over NaSO$_4$, concentrated, and purified by flash chromatography (hexane:ether, 3:1, V/V) to give DW-29 as a colorless syrup (1.2 g, 96%). Anal. Calcd for C$_{18}$H$_{32}$O$_5$Si: C, 60.64; H, 9.04. Found: C, 60.26; H, 8.77.

Preparation of DW-30

OsO$_4$ (10 mg) was added to a solution of DW-29 (1.2 g, 3.5 mmol), NMO (0.65 g, 5.5 mmol), pyridine (1.75 mL), and water (0.35 mL) in t-BuOH (10 mL) at room temperature under N$_2$. After being refluxed under N$_2$ for 3 hours, the reaction mixture was cooled to room temperature and quenched with saturated aqueous Na$_2$S$_2$O$_5$ (5 mL). Upon removing the solvent under reduced pressure, the resulting residue was purified by flash chromatography (hexane:ether, 1:1, V/V) to afford a diol as a colorless syrup (1.0 g, 85%) [a]$_D$25=−31.6((c 0.67, CHCl$_3$). IR (KBr): 3432, 3380, 1739, 1253, 1080 cm$^{-1}$. $^1$H NMR: δ5.28 (dd, J=9.9, 3.9 Hz, 1H), 4.47–4.35 (m, 2H), 4.0 (dd, J=9.9, 4.5 Hz, 1H), 3.7 (d, J=9.6 Hz, 1H), 3.6 (d, J=9.6 Hz, 1H), 2.94 (d, J=4.5 Hz, 1H, OH), 2.77 (s, 1H, OH), 2.18 (s, 3H), 1.95 (dd, J=14.4, 6.3 Hz, 1H), 1.67 (dd, J=14.4, 8.1 Hz, 1H), 1.50, 1.32, (s, each 3H), 0.88 (s, 9H), 0.078 (s, 6H). $^{13}$C NMR: δ171.4, 109.7, 74.63, 73.54, 72.67, 72.26, 70.21, 69.44, 34.8, 28.33, 26.14, 26.0, 21.39, 18.35, −5.35, −5.38. Anal. Calcd for C$_{18}$H$_{34}$O$_7$Si: C, 55.35; H, 8.77. Found: C, 55.44; H, 8.57.

To a solution of the above diol (0.8 g, 2 mmol) and 2-methoxypropene (1.3 mL) in dry CH$_2$Cl$_2$ (15 mL) was added catalytic amount of CSA under N$_2$ at room temperature. After being stirred for 2 hours, the reaction mixture quenched with triethylamine (0.1 mL), concentrated, and purified by flash chromatography (hexane:ether, 10:1 to 5:1.

the silica-gel was prebuffered with 1% triethylamine in hexane) to afford DW-30 as a colorless syrup (0.81 g, 96%). IR (KBr): cm⁻¹. ¹H NMR: δ5.43 (dd, J=6.3, 3.6 Hz, 1H), 4.56–4.43 (m, 2H), 4.28 (d, J=6.3 Hz, 1H), 3.7 (d, J=10.5 Hz, 1H), 3.65 (d, J=10.5 Hz, 1H), 2.11 (s, 3H), 2.04 (d, J=6.0 Hz, 2H), 1.45 (s, 3H), 1.41(s, 6H), 1.32 (s, 3H), 0.91 (s, 9H), 0.08, 0.07 (s, each 3H).

Preparation of DW-31

To a solution of DW-30 (0.81 g, 1.88 mmol) in dry THF (10 mL) was added dropwise DIBAL-H solution (1.0 M in hexane, 6 mL) at −20 (C. over 30 min. After being stirred at 0 C. for 3 hours, the reaction mixture was quenched with saturated aqueous NH₄Cl (3 mL), filtered, and washed with ether. The filtrate was concentrated and purified by flash chromatography (hexane:ether, 2:1, V/V) to give DW-31 as a colorless syrup (0.75 g, 94%). [a]$_D$25=+10.0((c 0.24, CHCl₃). IR (KBr): 3495 cm⁻¹. ¹H NMR: δ4.49–4.34 (m, 3H), 4.31 (d, J=3.9 Hz, 1H), 3.65 (s, 2H), 2.61 (br, 1H, OH), 2.07 (dd, J=13.5, 5.7 Hz, 1H), 1.80 (dd, J=13.5, 9.0 Hz, 1H), 1.50 (s, 3H), 1.41 (s, 6H), 1.38 (s, 3H), 0.91 (s, 9H), 0.084, 0.077 (s, each 3H). ¹³C NMR: δ109.3, 108.5, 83.51, 75.98, 73.13, 71.46, 69.47, 67.28, 34.43, 28.02, 26.97, 26.95, 26.20, 24.55, 18.72, −5.13, −5.26. Anal. Calcd for C₁₉H₃₆O₆Si: C, 58.72; H, 9.34. Found: C, 58.71; H, 8.96.

Preparation of Ketone DW-32

To a solution of DMSO (0.422 g, 5.4 mmol) in dry CH₂Cl₂ (1.5 mL) was added dropwise oxalyl chloride (0.250 mL, 2.7 mmol) under N₂ at −78 (C. The mixture was stirred at −78 (C. for 10 min, then removed from coolant and stirred for 3 min. Upon recooling to −78 (C., a solution of alcohol DW-31 (0.70 g, 1.8 mmol) in dry CH₂Cl₂ (6 mL) was added in one portion. After the mixture was stirred at −78 (C. for 1 hour, triethylamine (1.23 mL) was added dropwise. After being stirred at −78 (C. for an another 10 min and warmed to room temperature, the reaction mixture was quenched with saturated aqueous NH₄Cl (4 mL), extracted with CH₂Cl₂ (3(20 mL), washed with water and brine, dried over NaSO₄, concentrated, and purified by flash chromatography (hexane:ether, 5:1 to 2:1, V/V) to give ketone DW-32 as a colorless syrup (0.63 g, 90%). [a]$_D$25=+22.6((c 1.23, CHCl₃). IR (KBr): 1752 cm⁻¹. ¹H NMR: δ5.05 (d, J=8.4 Hz, 1H), 4.93 (m, 1H), 4.33 (s , 1H), 3.64 (d, J=10.5 Hz, 1H), 3.57 (d, J=10.5, 1H), 2.08 (ddd, J=14.4, 4.8, 2.7 Hz, 1H), 1.42 (ddd, J=14.4, 3.0, 2.4 Hz, 1H), 1.56, 1.49 (s, each 3H), 1.38 (s, 6H), 0.88 (s, 9H), 0.06, 0.05 (s, each 3H). ¹³C NMR: δ203.4, 112.3, 110.1, 86.38, 81.26, 77.76, 73.48, 67.67, 36.69, 27.24, 27.05, 26.41, 25.99, 24.82, 18.47, −5.26, −5.44. Anal. Calcd for C₁₉H₃₄O₆Si 1.5 H₂O: C, 55.18; H, 9.01. Found: C, 54.99; H, 8.69.

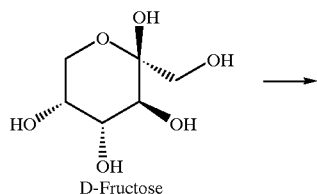
D-Fructose

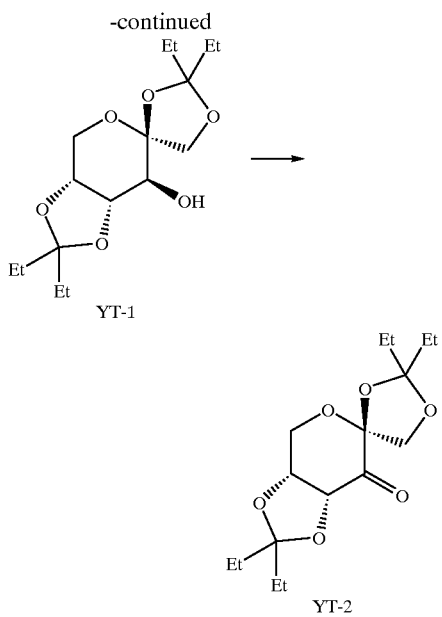
YT-1

YT-2

To a solution of 3-pentanone (10.6 mL, 8.6 g, 100 mmol) and trimethyl orthoformate (8.8 mL, 8.5 g, 80 mmol) in methanol (50 mL) was added TsOH H₂O (0.01 g) After the solution was heated at 60–70° C. for 3 hours (during this time methyl formate formed was distilled off), the bath temperature was raised to 90° C. and maintained at that temperature for 30 minutes to distill off the methanol. Upon cooling to room temperature, dioxane (100 mL) and D-fructose (7.2 g) were added. The reaction mixture was cooled in an ice bath, and 0.1 mL of 70% perchloric acid was added. After being stirred for 6 hours, the reaction was quenched by adding triethylamine and concentrated. The resulting residue was dissolved in dichloromethane (50 mL), washed with brine, dried over sodium sulfate, concentrated, and purified by flash chromatography (hexane:ether, 20:1 to 2:1, v/v) to give alcohol YT-1 as a syrup (7.81 g, 61%). ¹H NMR: δ4.23–4.08 (m, 4H), 3.99–3.93 (m, 2H), 3.73 (d, J=5.1, 1H), 2.12 (bs, 1H), 1.81–1.60 (m, 8H), 0.99–0.88 (m, 12H). ¹³C NMR: δ115, 113.7, 104.3, 76.86, 73.19, 72.97, 70.82, 60.67, 30.20, 29.60, 28.94, 28.69, 8.77, 8.67, 8.03.

PCC (11.8 g, 55 mmol) was added portionwise over 15 min to a mixture of alcohol YT-1 (7.52 g, 24 mmol) and powdered 3A molecular sieves (22 g, activated at 180–200° C. under vacuum) in dichloromethane (100 mL). After the reaction mixture was stirred for 3 hours under nitrogen, it was filtered through celite and washed carefully with ether. The filtrate was concentrated and the residue was purified by passing through a short silica gel column (hexane:ether, 1:1, v/v) to afford a syrup (YT-2) which solidified in refrigerator after a few hours (1.47 g, 81%). ¹H NMR: δ4.71 (d, J=5.9, 1H), 4.62 (d, J=9.2 Hz, 1H), 4.58 (ddd, J=5.9, 2.3, 1.0 Hz, 1H), 4.39 (dd, J=13.5, 2.3 Hz, 1H), 4.14 (d, J=13.5 Hz, 1H), 3.96 (d, J=9.3 Hz, 1H). ¹³C NMR: δ197.5, 118.4, 114.9, 114.2, 104.2, 77.73, 75.71, 70.65, 60.67, 30.71, 29.96, 29.16, 29.08, 8.60, 8.47, 8.44, 7.82. Anal. Cald. for C₁₆H₂₆O₆: C, 61.12; H, 8.34. Found: C, 61.36; H, 8.17.

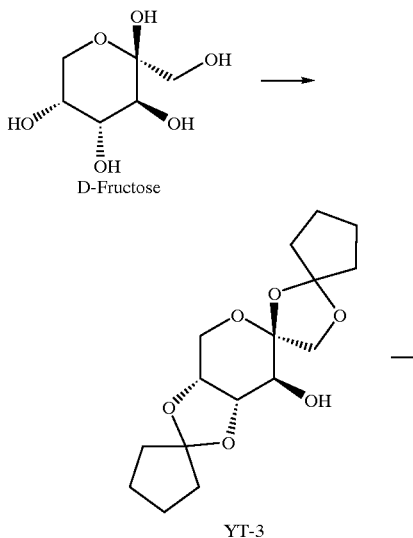

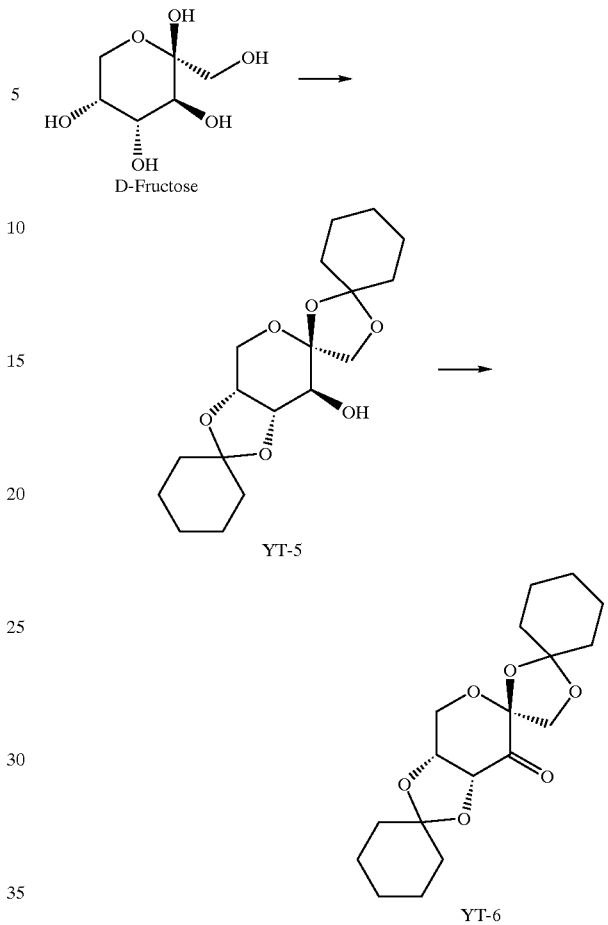

Preparation of Ketone YT-4

Perchloric acid (70%) (0.1 g) was added to a suspension of D-fructose (1.8 g, 10 mmol) in cyclopentanone (30 mL) and 1,1-dimethoxycyclopentane (2.86 g, 22 mmol) at 0° C. (ice bath). After being stirred under nitrogen at 0° C. for 6 hours, the reaction mixture was neutralized with con. ammonium hydroxide and concentrated. The resulting residue was dissolved in $CH_2Cl_2$ (20 mL), washed with brine, dried over sodium sulfate, concentrated, and purified by flash chromatography (hexane:ether, 20:1 to 2:1, v/v), and followed by recrystallization (hexane) to give alcohol YT-3 as a white needle (1.15 g, 36.9%). IR: 3455 $cm^{-1}$. $^1H$ NMR: δ4.16 (d, J=8.7 Hz, 1H), 4.12–4.01 (m, 4H), 3.89 (d, J=8.7 Hz, 1H), 3.63 (d, J=6.1 Hz, 1H), 2.09 (bs, 1H), 2.00–1.64 (m, 16H). $^{13}C$ NMR: δ121.5, 119.4, 104.4, 77.16, 73.88, 72.44, 70.55, 61.04, 37.61, 37.56, 36.72, 36.42, 24.10, 23.76, 23.48, 23.04.

PCC (1.86 g, 8.6 mmol) was added portionwise over 15 min to a mixture of alcohol YT-3 (1.0 g, 3.2 mmol) and powdered 3A molecular sieves (3.5 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-4 as colorless crystal (0.83 g, 83%). IR: 1745 $cm^{-1}$. $^1H$ NMR: δ4.73 (d, J=5.5 Hz, 1H), 4.51 (d, J=9.5 Hz, 1H), 4.44 (ddd, J=5.5, 2.1, 0.9 Hz, 1H), 4.38 (dd, J=13.4, 2.1 Hz, 1H), 4.12 (d, J=13.4 Hz, 1H), 3.87 (d, J=9.5 Hz, 1H), 2.00–1.63 (m, 16H). $^{13}C$ NMR: δ196.8, 123.2, 120.5, 104.0, 78.36, 75.78, 70.03, 60.46, 37.41, 37.04, 36.87, 36.16, 23.91, 23.71, 23.41, 23.21. Anal. Calcd. for $C_{16}H_{22}O_6$: C, 61.9; H, 7.1. Found: C, 61.66; H, 7.21.

Preparation of Ketone YT-6

To a solution of con. sulfuric acid (3 mL) in cyclohexanone (40 mL) at 0° C. was added powered D-fructose (20.0 g, 111.1 mmol). The reaction mixture solidified after 40 min stirring at 0° C. After being stood at room temperature for additional 24 hours, the reaction mixture was dissolved in chloroform (150 mL) and washed with saturated sodium carbonate, brine, saturated ammonium chloride, water, brine, dried over magnesium sulfate, concentrated, and recrystallized (hexane) to give alcohol YT-5 as a white needle (13.6 g, 36.0%). $^1H$ NMR: δ4.32–4.10 (m, 4H), 4.03 (d, J=13.5 Hz, 1H), 3.97 (d, J=8.9 Hz, 1H), 3.65 (dd, J=8.6, 6.9 Hz, 1H), 1.96 (d, J=8.7 Hz, 1H), 1.80–1.38 (m, 20H). $^{13}C$ NMR: δ112.7, 110.3, 104.5, 77.23, 73.19, 72.15, 71.02, 61.17, 37.96, 36.09, 36.04, 35.46, 25.22, 24.23, 24.14, 24.05, 23.89.

PCC (17.46 g, 81 mmol) was added portionwise over 15 min to a mixture of alcohol YT-5 (10.2 g, 30 mmol) and powdered 3A molecular sieves (31.8 g) in dichloromethane (150 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-6 as a white solid (8.11 g, 80.0%). $^1H$ NMR: δ4.75 (d, J=5.7 Hz, 1H), 4.59 (d, J=9.5 Hz, 1H), 4.55 (ddd, J=5.6, 2.2, 0.8 Hz, 1H), 4.39 (dd, J=13.5, 2.2 Hz, 1H), 4.13 (d, J=13.5 Hz, 1H), 3.98 (d, J=9.5 Hz, 1H), 1.79 (t, J=6.1 Hz, 2H), 1.68–1.57 (m, 14H), 1.41 (bs, 4H). $^{13}C$ NMR: δ197.5, 114.8, 111.5, 103.9, 77.78, 75.73, 69.79, 60.46, 36. 49, 36.36, 35.65, 35.49, 25.11, 25.07, 24.15, 24.10, 23.95, 23.91. Anal. Calcd. for $C_{18}H_{26}O_6$: C, 63.89; H, 7.74. Found: C, 63.96; H, 7.72.

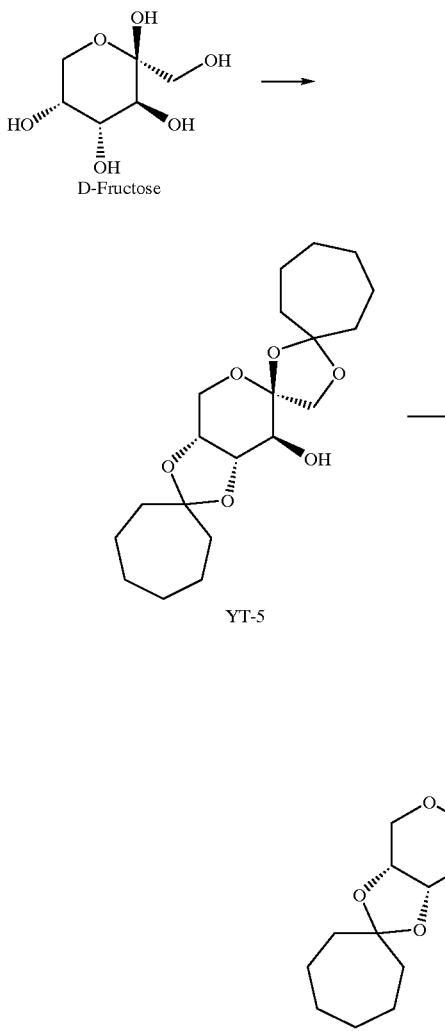

Preparation of Ketone YT-8

To a solution of cycloheptanone (23.6 mL, 22.4 g, 200 mmol) and trimethyl orthoformate (11.3 mL, 10.6 97 100 mmol) in methanol (50 mL) was added TsOH.H$_2$O (0.05 g). After the solution was heated at 50–60° C. for 3 hours (during this time methyl formate formed was distilled off), the bath temperature was raised to 90° C. and maintained at that temperature for 30 minutes to distill off the methanol. Upon cooling to room temperature, dioxane (50 mL) and D-fructose (9.0 g, 50 mmol) were added. The reaction mixture was cooled in an ice bath, and 1 mL of 70% perchloric acid was added. After being stirred for 6 hours, the reaction mixture was neutralized by adding triethylamine and concentrated. The resulting residue was dissolved in dichloromethane (80 mL), washed with brine, dried over sodium sulfate, concentrated, and purified by flash chromatography (hexane:ether, 20:1 to 2:1) to give alcohol YT-7 as a white solid (3.64 g, 21.8%). $^1$H NMR: δ4.18–4.07 (m, 4H), 3.99 (d, J=13.2 Hz, 1H), 3.93 (d, J=8.9 Hz, 1H), 3.65 (d, J=6.1 Hz, 1H), 2.0–1.78 (m, 9H), 1.57 (bs, 16H). $^{13}$C NMR: δ116.7, 114.3, 104.4, 77.10, 73.09, 72.19, 70.72, 61.17, 41.41, 39.56, 38.99, 38.39, 29.59, 29.47, 29.18, 29.11, 22.84, 22.40, 22.35. $^{13}$C NMR: δ116.7, 114.3, 104.4, 77.10, 73.09, 72.19, 70.72, 71.17, 41.41, 39.56, 38.99, 38.39, 29.59, 29.47, 29.18, 29.11, 22.84, 22.40, 22.35.

PCC (3.4 g, 16 mmol) was added portionwise over 15 min to a mixture of alcohol YT-7 (2.51 g, 6.8 mmol) and powdered 3A molecular sieves (7.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-8 as a white solid (2.25 g, 90.1%). $^1$H NMR: δ4.68 (d, J=5.6 Hz, 1H), 4.52 (d, J=9.5 Hz, 1H), 4.46 (ddd, J=5.6, 2.1, 0.8 Hz, 1H), 4.33 (dd, J=13.4, 2.1 Hz, 1H), 4.08 (d, J=13.4 Hz, 1H), 3.91 (d, J=9.5 Hz, 1H), 2.00–1.40 (m, 24H). $^{13}$C NMR: δ197.5, 118.8, 115.5, 104.0, 77.50, 69.86, 60.43, 40.26, 39.48, 38.83, 38.73, 29.48, 29.07, 25.58, 22.46, 22.44, 22.25. Anal. Calcd. for $C_{20}H_{30}O_6$: C, 65.55; H, 8.27. Found: C, 65.81; H, 8.17.

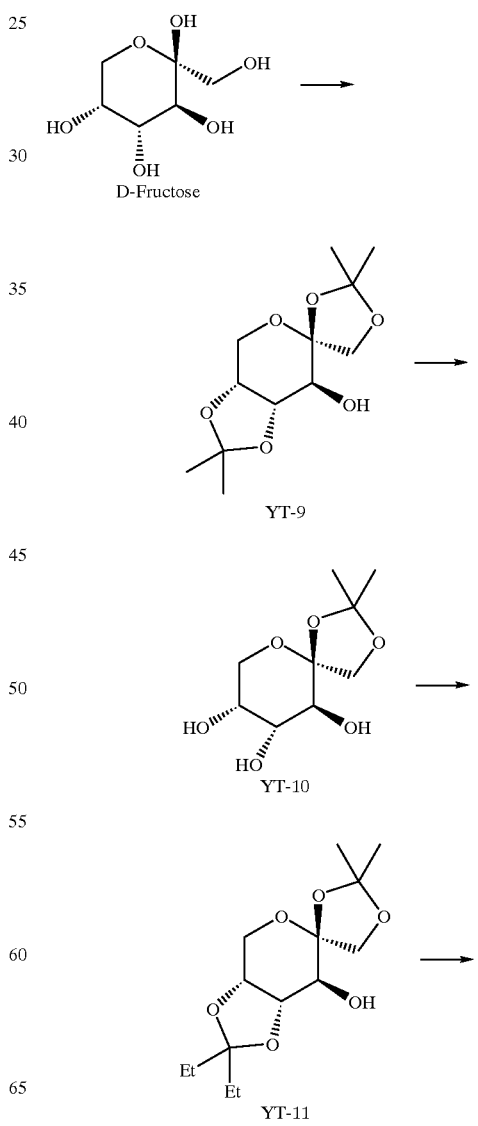

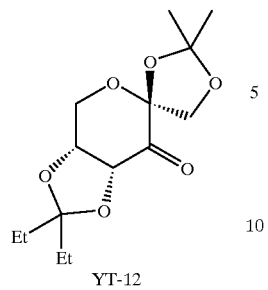

YT-12

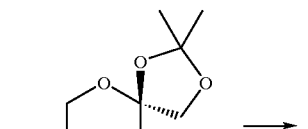

YT-10

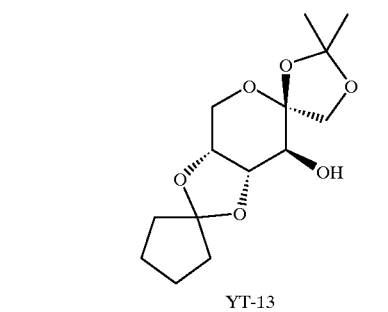

YT-13

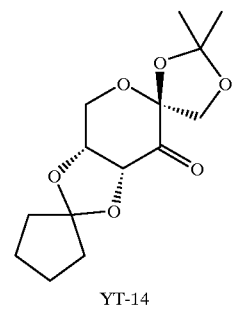

YT-14

Preparation of Ketone YT-12

Perchloric acid (70%) (8.6 mL) was added to a suspension of D-fructose (36.84 g, 204.7 mmol) in acetone (740 mL) and 2,2-dimethoxypropane (14.8 mL, 120 mmol) at 0° C. (ice bath). After being stirred under nitrogen at 0° C. for 6 hours, the reaction mixture was neutralized with con. ammonium hydroxide and concentrated. The resulting solid residue was recrystallized from hexane-$CH_2Cl_2$ (4:1, v/v) to afford alcohol YT-9 as white needles (28.34 g, 53.2%). mp 117–118.5° C., $[a]^{25}_D = -144.2°$ (c 1.0, $CHCl_3$). IR (KBr): 3547 cm$^{-1}$. $^1$H NMR: δ4.22 (ddd, J=5.7, 2.7, 0.9 Hz, 1H), 4.19 (d, J=9.0 Hz, 1H), 4.13 (dd, J=6.8, 5.7 Hz, 1H), 4.12 (dd, J=13.2, 2.7 Hz, 1H), 4.01 (dd, J=13.2, 0.9 Hz, 1H), 3.98 (d, J=9.0 Hz, 1H), 3.67 (dd, J=8.1, 6.8 Hz, 1H), 1.99 (d, J=8.1 Hz, 1H), 1.54 (s, 3H), 1.52 (s, 3H), 1.44 (s, 3H), 1.37 (s, 3H). $^{13}$C NMR: δ112.0, 109.6, 104.7, 77.48, 73.53, 73.52, 70.60, 60.96, 28.13, 26.62, 26.46, 26.14.

To a solution of alcohol YT-9 (13.34 g, 51 mmol) in 150 mL of acetonitrile-water (9:1, v/v) was added DDQ (1.13 g, 5 mmol). After the mixture was stirred at room temperature for 6 hours, the solvent was evaporated. The resulting reddish solid residue was dissolved in ethyl acetate, dried over sodium sulfate, and concentrated to give alcohol YT-10 as a reddish solid (9.98 g, 88%).

To a solution of 3,3-dimethoxylpentane (4.41 g, 30 mmol) in 3-pentanone (22 mL) were added cupric sulfate (1.0 g) and con. sulfuric acid (0.05 g). After the mixture was stirred for 5 min, alcohol YT-10 (2.97 g, 13.5 mmol) was added. After being stirred additional 3.5 hours at room temperature, the reaction mixture was neutralized with triethylamine (0.8 mL) and filtered. The filtrate was concentrated and purified by flash chromatography (hexane:ether, 20:1 to 2:1, v/v) to afford alcohol YT-11 as a syrup (2.39 g, 61.5%). IR: 3468 cm$^{-1}$. $^1$H NMR: δ4.24–4.15 (m, 3H), 4.10 (dd, J=13.2, 2.7 Hz, 1H), 4.00–3.95 (m, 2H), 3.71 (d, J=6.0 Hz, 1H), 2.05 (bs, 1H), 1.79–18.1 (m, 2H), 1.63 (q, J=7.5 Hz, 2H), 1.51 (s, 3H), 1.44 (s, 3H)I, 0.96 (t, J=7.5, 3H), 0.90 (t, J=7.5, 3H). $^{13}$C NMR: δ113.7, 111.8, 104.5, 77.01, 73.22, 72.77, 70.64, 61.47, 30.23, 28.72, 26.71, 26.37, 8.76, 8.67.

PCC (4.10 g, 19.0 mmol) was added portionwise over 15 min to a mixture of alcohol YT-11 (2.03 g, 7.0 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-12 as a white solid (1.61 g, 79%). IR: 1750 cm$^{-1}$, $^1$H NMR: δ4.68 (d, J=5.9 Hz, 1H), 4.61–4.55 (m, 2H), 4.35 (dd, J=13.5, 2.2 Hz, 1H), 4.12 (d, J=13.5 Hz, 1H), 3.98 (d, J=9.6 Hz, 1H), 1.70–1.61 (m, 4H), 1.55 (s, 3H), 1.40 (s, 3H), 0.92 (t, J=7.4, 3H), 0.91 (t, J=7.4 Hz, 3H). $^{13}$C NMR: δ197.5, 114.9, 114.0, 104.2, 76.67, 75.69, 70.48, 60.64, 29.91, 29.18, 26.72, 26.13, 8.56, 8.36. Anal. Calcd. for $C_{14}H_{22}O_6$: C, 58.73; H, 7.74. Found: C, 58.51; H, 7.58.

Preparation of Ketone YT-14

To a solution of 1,1-dimethoxylcyclopentane (3.9 g, 30 mmol) in cyclopentanone (20 mL) was added a solution of cupric sulfate (6.0 g) and con. sulfuric acid (0.2 g) in dioxane (20 mL). Upon stirring for 5 min, alcohol YT-10 (5.50 g, 25 mmol) was added. After being stirred 1.5 hours at room temperature, the reaction mixture was neutralized by adding triethylamine (1.0 mL) and filtered. The filtrate was concentrated and purified by flash chromatography (hexane:ehter, 20:1 to 3:2) to give alcohol YT-13 (2.45 g, 33.6%). IR: 3462 cm$^{-1}$. $^1$H NMR: δ4.19 (d, J=8.7 Hz, 1H), 4.15–4.01 (m, 4H), 3.98 (d, J=8.7 Hz, 1H), 3.61 (bs, 1H), 2.00–1.65 (m, 9H), 1.52 (s, 3H), 1.45 (s, 3H). $^{13}$C NMR: δ119.5, 112.2, 104.9, 77.31, 73.94, 72.36, 70.38, 60.70, 37.66, 26.62, 26.53, 23.80, 23.53.

PCC (1.85 g, 19 mmol) was added portionwise over 15 min to a mixture of alcohol YT-13 (0.91 g, 3.2 mmol) and powdered 3A molecular sieves (8.2 g) in dichloromethane (60 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-14 as a white solid (0.69 g, 76%). IR: 1743 cm$^{-1}$. $^1$H NMR: δ4.72 (d, J=5.3 Hz, 1H), 4.61 (d, J=9.5 Hz, 1H), 4.44–4.36 (m, 2H), 4.13 (d, J=13.1 Hz, 1H), 3.98 (d, J=9.5 Hz, 1H), 2.05–1.65 (m, 8H), 1.55 (s, 3H), 1.40 (s, 3H). $^{13}$C NMR: δ196.8, 120.5, 114.0, 104.3, 78.38, 75.80, 70.13, 60.22, 37.44, 37.07, 26.72, 26.23, 23.75, 23.44. Anal. Calcd. for $C_{14}H_{20}O_6$: C, 59.14; H, 7.09. Found: C, 58.96; H, 7.26.

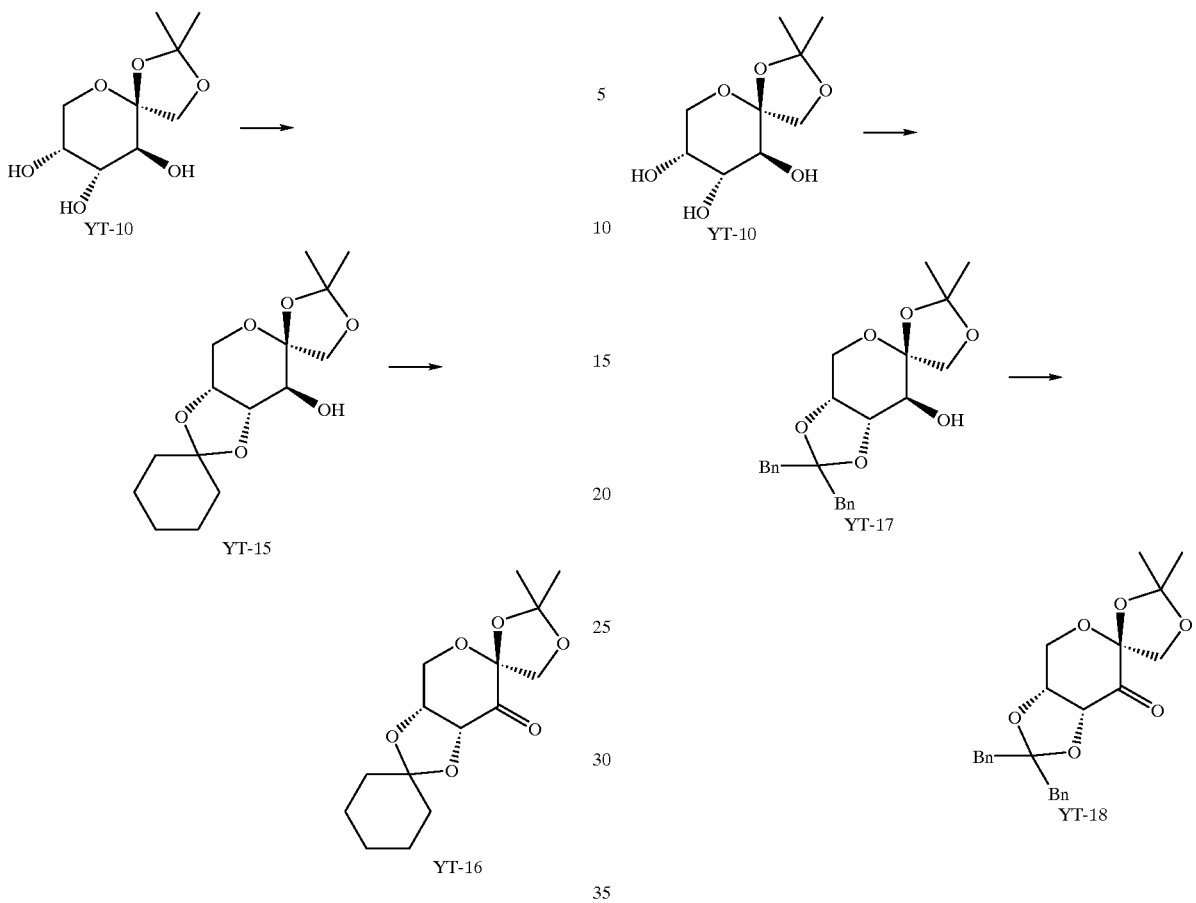

Preparation of Ketone YT-16

To a mixture of alcohol YT-10 (2.91 g, 13.2 mmol) in cyclohexaone (30 mL) and 1,1-dimethoxylcyclohexane (5.0 mL) were added cupric sulfate (5.0 g) and con. sulfuric acid (0.05 g). After being stirred for 50 min at room temperature under nitrogen, the reaction mixture was neutralized with triethylamine (1.0 mL) and filtered. The filtrate was concentrated and purified by flash chromatography (hexane:ether, 20:1 to 3:2) to give alcohol YT-15 (2.60 g, 65.5%). $^1$H NMR: δ4.22–4.09 (m, 4H), 4.02 (d, J=13.2 Hz, 1H), 3.97 (d, J=8.2, 1H), 3.66 (dd, J=5.0, 5.0 Hz, 1H), 2.11 (d, J=5.3 Hz, 1H), 1.76–1.55 (m, 8H), 1.52 (s, 3H), 1.44 (s, 3H), 1.45–1.37 (m, 2H). $^{13}$C NMR: δ112.0, 110.3, 104.7, 77.01, 73.11, 72.53, 70.92, 61.06, 37.90, 35.38, 26.63, 26.45, 25.20, 24.20, 23.86.

PCC (5.06 g, 23.5 mmol) was added portionwise over 15 min to a mixture of alcohol YT-15 (2.60 g, 8.7 mmol) and powdered 3A molecular sieves (10.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 8:1, v/v) to afford YT-16 as a white solid (1.89 g, 76%). $^1$H NMR: δ4.72 (d, J=5.6 Hz, 1H), 4.60 (d, J=9.5 Hz, 1H), 4.55 (dd, J=5.6, 2.2 Hz, 1H), 4.37 (dd, J=13.4, 2.2 Hz, 1H), 4.13 (d, J=13.4, 1H), 3.98 (d, J=9.5 Hz, 1H), 1.62–1.34 (m, 10H), 1.55 (s, 3H), 1.40 (s, 3H). $^{13}$C NMR: δ197.4, 113.9, 111.5, 104.3, 77.71, 75.66, 70.21, 60.43, 36.90, 35.61, 26.67, 26.16, 25.09, 24.07, 23.91. Anal. Calcd. for $C_{15}H_{20}O_6$: C, 60.39; H, 7.43. Found: C, 60.42; H, 7.47.

Preparation of Ketone YT-18

To a solution of 2,2-dimethoxy-1,3-diphenylpropane (5.12 g, 20 mmol) in dioxane (50 mL), were added cupric sulfate (1.5 g) and con. sulfuric acid (0.12 g), followed by alcohol YT-17 (3.30 g, 15 mmol). After being stirred 3 hours at room temperature under nitrogen, the reaction mixture was neutralized with triethylamine and filtered. The filtrate was concentrated and purified by flash chromatography (hexane:ether, 17:1 to 2:1, v/v) to give alcohol YT-17 (2.94 g, 47.6%).

PCC (4.01 g, 18.6 mmol) was added portionwise over 15 min to a mixture of alcohol YT-17 (2.84 g, 6.9 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 20:1 to 2:1, v/v) to afford YT-18 as a white solid (1.96 g, 69.46). $^1$H NMR: δ7.45–7.20 (m, 10H), 4.50 (d, J=9.5 Hz, 1H), 4.44 (d, J=6.1 Hz, 1H), 4.08 (dd, J=13.5, 2.2 Hz, 1H), 3.98 (d, J=13.5 Hz, 1H), 3.88 (d, J=9.5 Hz, 1H), 3.58 (ddd, J=6.0, 2.0, 1.0 Hz, 1H), 2.98–2.81 (m, 4H). $^{13}$C NMR: δ197.0, 136.2, 136.1, 131.1, 131.0, 128.2, 126.8, 114.0, 112.9, 104.0, 78.52, 75.87, 70.33, 60.30, 46.21, 43.94, 26.70, 26.09. Anal. Calcd. for $C_{24}H_{26}O_6$: C, 70.28; H, 6.38. Found: C, 70.18; H, 6.31.

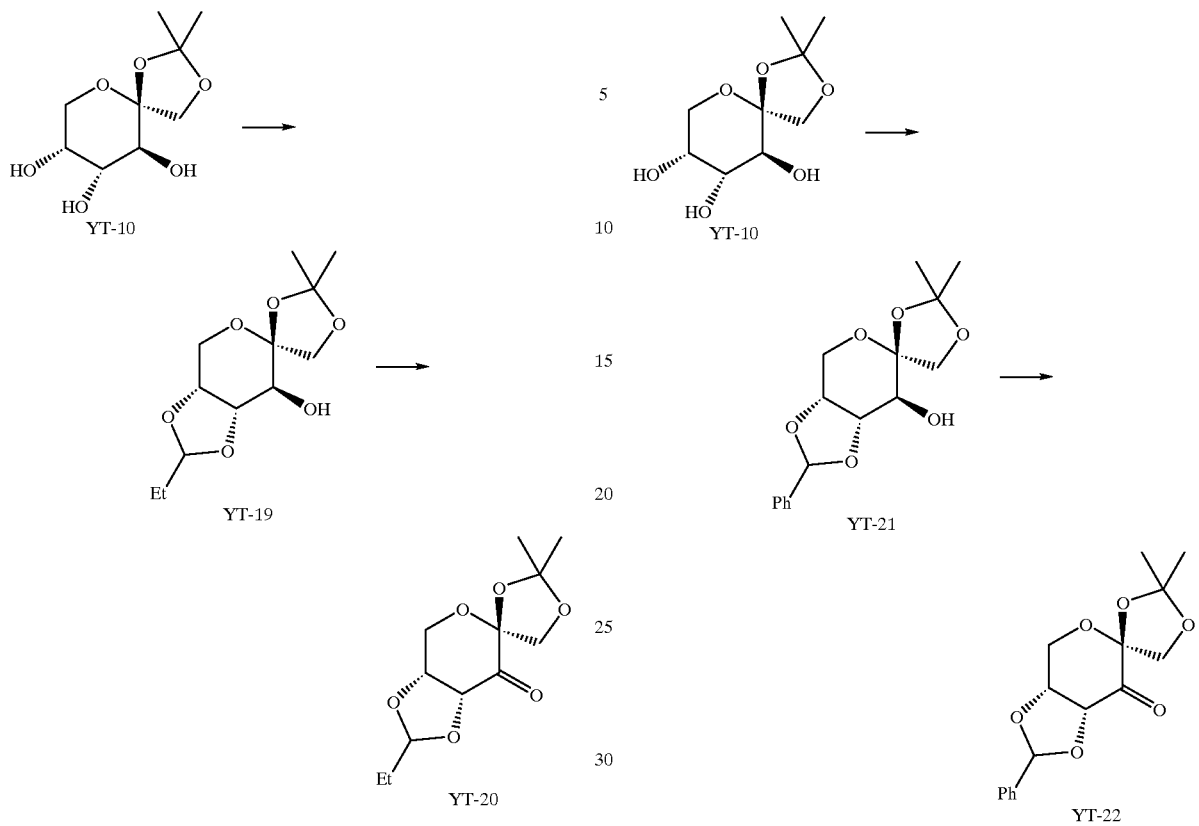

Preparation of Ketone YT-20

To a mixture CH(OMe)₃ (2.2 mL, 2.22 g, 20 mmol), alcohol YT-10 (2.20 g, 10 mmol), and propanal (11.6 g, 200 mmol) in THF (40 mL) was added TsOH.H₂O (0.5 g) at room temperature. After being stirred overnight, the reaction mixture was neutralized by with triethylamine, concentrated, and purified by flash chromatography (hexane:ether, 20:1 to 4:3, v/v) to give alcohol YT-19 as a white solid (1.20 g, 46%). IR: 3468 cm⁻¹ ¹H NMR: δ4.96 (t, J=6.0 Hz, 1H), 4.17 (d, J=8.8 Hz, 1H), 4.16–4.04 (m, 4H), 3.97 (d, J=8.8 Hz, 1H), 3.60 (d, J=4.5 Hz, 1H), 2.25 (d, J=7.7, 1H), 1.80–1.70 (m, 2H), 1.51 (s, 3H), 1.44 (s, 3H), 1.00 (t, J=7.5 Hz, 3H). ¹³C NMR: δ112.1, 106.3, 104.7, 76.81, 75.25, 72.52, 71.18, 60.74, 27.96, 26.64, 26.47, 8.509.

PCC (2.2 g, 10.3 mmol) was added portionwise over 15 min to a mixture of alcohol YT-19 (1.0 g, 3.8 mmol) and powdered 3A molecular sieves (4.4 g) in dichloromethane (20 mL). After being stirred for 3 hours under nitrogen, the reaction mixture was filtered through celite and silicon gel (lower layer) and washed carefully with hexane-ether (1:1, v/v), the filtrate was concentrated to afford YT-20 as a solid (0.83 g, 84%). ¹H NMR: δ5.02 (t, J=4.9 Hz, 1H), 4.69 (d, J=5.9 Hz, 1H), 4.60 (d, J=9.6 Hz, 1H), 4.49–4.04 (m, 3H), 3.99 (d, J=9.6 Hz, 1H), 1.82–1.62 (m, 2H), 1.55 (s, 3H), 1.40 (s, 3H), 0.97 (t, J=7.5 Hz ). ¹³C NMR: 196.4, 114.1, 107.0, 104.2, 79.61, 75.20, 70.29, 60.12, 27.60, 26.73, 26.19, 8.21. Anal. Calcd. for C₁₂H₁₈O₆: C, 55.81; H, 7.02. Found: C, 55.93; H, 7.11.

Preparation of Ketone YT-22

To a mixture CH(OEt)₃ (3 mL, 18 mmol) and TsOH.H₂O (0.5 g) in dioxane (30 mL) was added benzaldehyde (15 mL) room temperature. After stirring for 1 hour, YT-10 (2.20 g, 10 mmol) was added. After 4 hours another patch of CH(OEt)₃ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-21 as a white solid (1.60 g, 52%).

PCC (1.9 g, 8.8 mmol) was added portionwise over 15 min to a mixture of alcohol YT-21 (1.0 g, 3.3 mmol) and powdered 3A molecular sieves (3.8 g) in dichloromethane (20 mL). After being stirred for 3 hours under nitrogen, the reaction mixture was filtered through celite and silicon gel (lower layer) and washed carefully with hexane:ether (1:1, v/v). The filtrate was concentrated to afford YT-22 as a solid (0.73 g, 74%). ¹H NMR: δ7.50 (m, 5H), 5.91 (s, 1H), 4.84 (d, J=6.1 Hz, 1H), 4.78–4.58 (m, 2H), 4.44 (d, J=13.8 Hz, 1H), 4.25 (d, J=13.8 Hz, 1H), 4.01 (d, J=9.1 Hz, 1H), 1.57 (s, 3H), 1.42 (s, 3H). ¹³C NMR: δ196.0, 136.1, 130.0, 128.6, 127.3, 114.1, 105.4, 104.3, 80.13, 75.75, 70.45, 60.24, 26.73, 26.17. Anal. Calcd. for C₁₆H₁₈O₆: C, 62.74; H, 5.92. Found: C, 62.63; H, 6.00.

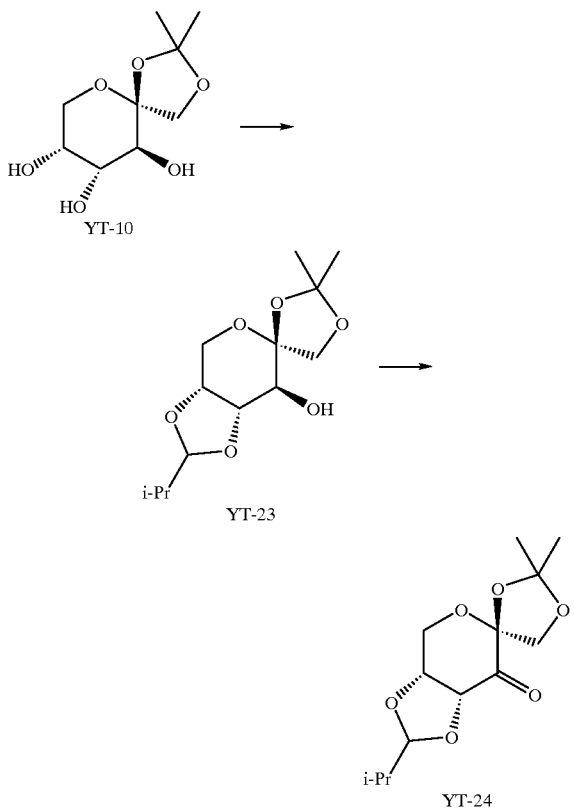

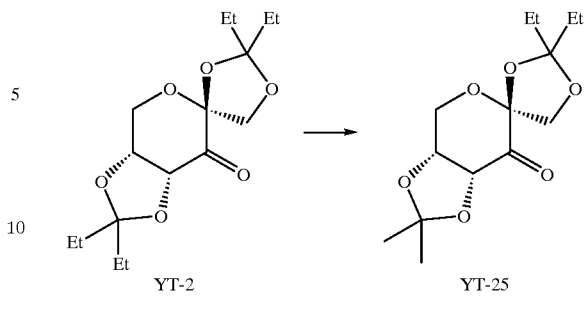

Preparation of Ketone YT-25

TsOH.H$_2$O (0.6 g) was added to a solution of ketone YT-2 (1.47 g, 5.7 mmol) in acetone (60 mL). After being stirred for 0.5 hour at room temperature, 2,2-dimethoxypropane (2.0 mL, 1.69 g, 16 mmol) was added. The mixture was stirred at room temperature for 3.5 hours, neutralized with triethylamine, concentrated, and purified by flash chromatography (hexane:ether, 15:1 to 10:1, v/v) to afford YT-25 as a syrup (0.62 g, 46.0%). $^1$H NMR: δ4.76 (d, J=5.5 Hz, 1H), 4.63 (d, J=9.4 Hz, 1H), 4.56 (ddd, J=5.5, 2.2, 0.9 Hz, 1H), 4.42 (dd, J=13.5, 2.2 Hz, 1H), 4.13 (d, J=13.5 Hz, 1H), 3.96 (d, J=9.4 Hz, 1H), 1.86 (q, J=7.4 Hz, 2H), 1.63 (q, J=7.4 Hz, 2H), 1.46 (s, 3H), 1.40 (s, 3H), 0.96 (t, J=7.4 Hz, 3H), 0.82 (t, J=7.4 Hz, 3H). $^{13}$C NMR: δ197.0, 118.3, 110.7, 104.3, 78.11, 76.05, 70.36, 60.34, 30.12, 29.06, 27.32, 26.23, 8.42, 7.75. Anal. Calcd. for C$_{14}$H$_{22}$O$_6$: C, 58.73; H, 7.74. Found: C, 58.81; H, 7.80.

Preparation of Ketone YT-24

To a mixture CH(OEt)$_3$ (3 mL, 18 mmol) and TsOH.H$_2$O (0.2 g) in dioxane (30 mL) at 0° C. was added isobutanal (30 mL) room temperature. After stirring for 1 hour, YT-10 (2.2 g, 10 mmol) was added. After 4 hours, another patch of CH(OEt)$_3$ (2.0 mL, 12 mmol) was added. The reaction mixture was stirred for another 2 hours, neutralized with triethylamine (1 mL), concentrated, and purified by flash chromatography (hexane:ether, 20:1 to 3:2, v/v) to give alcohol YT-23 as a white solid (1.48 g, 54%). $^1$H NMR: δ4.71 (d, J=5.4 Hz, 1H), 4.18 (d, J=8.8 Hz, 1H), 4.10 (d, J=5.4 Hz, 1H), 4.09 (d, J=6.2 Hz, 1H), 3.97 (d, J=8.8 Hz, 1H), 3.62 (d, J=6.2 Hz, 1H),1.91–1.80 (m, 1H), 1.51 (s, 3H), 1.45 (s, 3H), 1.00 (d, J=6.9 Hz, 3H), 0.98 (d, J=6.9 Hz, 3H). $^{13}$C NMR: δ112.0, 109.1, 104.7, 76.77, 75.11, 72,59, 70.92, 60.89, 32.51, 31.76, 26.67, 26.44, 17.38, 17.34.

PCC (1.93 g, 9.0 mmol) was added portionwise over 15 min to a mixture of alcohol YT-23 (0.91 g, 3.3 mmol) and powdered 3A molecular sieves (3.86 g) in dichloromethane (20 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-24 as a solid (0.64 g, 71%). $^1$H NMR: δ4.77 (d, J=5.4 Hz, 1H), 4.66 (d, J=5.9 Hz, 1H), 4.57–4.36 (m, 2H), 4.16 (d, J=13.4 Hz, 1H), 3.98 (d, J=9.5 Hz, 1H), 1.91–1.75 (m, 1H), 1.55 (s, 3H), 1.40 (s, 3H), 0,99 (d, J=6.9 Hz, 3H), 0.94 (d, J=6.9 Hz, 3H). $^{13}$C NMR: δ196.3, 114.0, 109.8, 104.2, 79.33, 75.07, 70.38, 60.24, 32.31, 26,73, 26.17, 17,14, 16,94. Anal. Calcd. for C$_{13}$H$_2$O$_6$: C, 57.34; H, 7.43. Found: C, 57.28; H, 7.42.

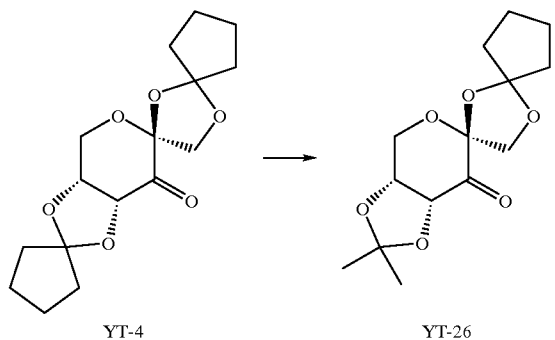

Preparation of Ketone YT-26

TsOH.H$_2$O (0.25 g) was added to a solution of ketone YT-4 (0.62 g, 2.0 mmol) in acetone (30 mL). After being stirred for 0.5 hour at room temperature, 2,2-dimethoxypropane (1.0 mL, 0.84 g, 8 mmol) was added. The mixture was stirred at room temperature for 3.5 hours, neutralized with triethylamine, concentrated, and purified by chromatography to give YT-26 as a solid (0.30 g, 52%). $^1$H NMR: δ4.74 (d, J=5.6 Hz, 1H), 4.56–4.54 (m, 2H), 4.38 (dd, J=9.4 Hz, 1H), 4.13 (d, J=13.5 Hz, 1H), 3.90 (d, J=9.4 Hz, 1H), 1.97–1.67 (m, 10H), 1.46 (s, 3H), 1.40 (s, 3H). $^{13}$C NMR: δ197.2, 123.3, 110.9, 104.0, 78.16, 76.11, 70.17, 60.57, 36.93, 36.22, 27.37, 26.28, 23.96, 23.26. Anal. Calcd. for C$_{13}$H$_{20}$O$_6$: C, 59.14; H, 7.09. Found: C, 58.95; H, 7.28.

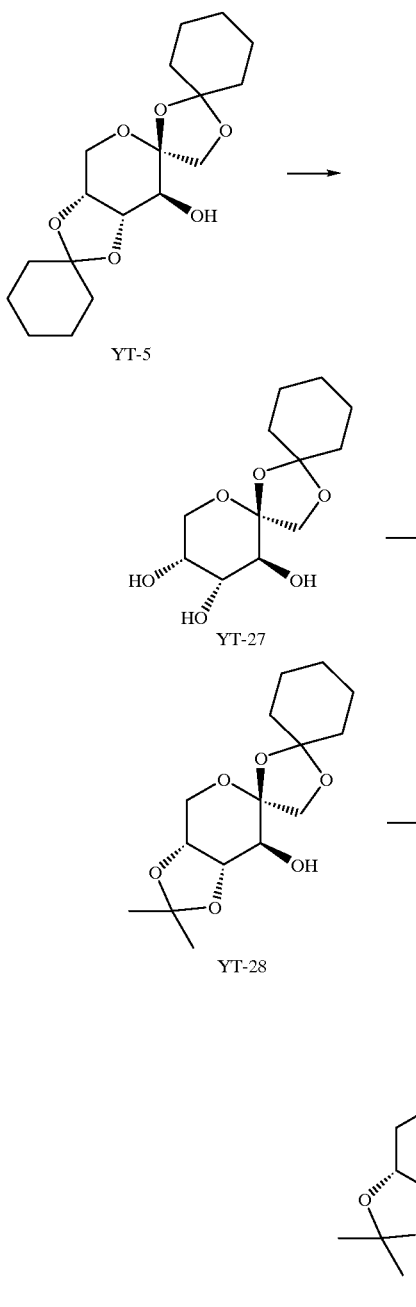

YT-28 as a solid (1.92 g, 76%). $^1$H NMR: δ4.22 (ddd, J=5.8, 1.5, 0,9 Hz, 1H), 4.19–4.10 (m, 3H), 4.01 (d, J=13.4 Hz, 1H), 3.97 (d, J=8.6 Hz, 1H), 3.66 (dd, J=8.6, 7.0, 1H), 1.96 (d, J=8.6, 1H), 1.80–1.37 (m, 10H), 1.54 (s, 3H), 1.37 (s, 3H). $^{13}$C NMR: δ112.8, 109.6, 114.4, 77.69, 73.61, 72.15, 70.70, 61.07, 36.10, 36.04, 28.19, 26.20, 25.20, 24.14, 24.05.

PCC (3.05 g, 14.1 mmol) was added portionwise over 15 min to a mixture of alcohol YT-28 (1.57 g, 5.2 mmol) and powdered 3A molecular sieves (7.1 g) in dichloromethane (30 mL). After being stirred for 3 hours under nitrogen, the reaction mixture was diluted with hexane (50 mL), filtered through celite, and washed carefully with ether. The filtrate was concentrated and purified by passing through a short silica gel column (hexane:ether, 20:1 to 8:1, v/v) to afford YT-29 as a white solid (1.26 g, 80.8%). $^1$H NMR: δ4.76 (d, J=5.6 Hz, 1H), 4.60 (d, J=9.5 Hz, 1H), 4.56 (ddd, J=5.6, 2.2, 0.9 Hz, 1H), 4.41 (dd, J=13.5, 2.2 Hz, 1H), 4.12 (dd, J=13.5, 0.9 Hz, 1H), 3.99 (d, J=9.5 Hz, 1H), 1.80 (t, J=6.1, 2H), 1.70–1.40 (m, 8H), 1.64 (s, 3H), 1.40 (s, 3H). $^{13}$C NMR: δ197.2, 114.9, 110.8, 104.0, 78.17, 76.13, 69.81, 60.34, 36.39, 35.54, 27.38, 26.29, 25.09, 24.17, 23.93. Anal. Calcd. for $C_{15}H_{22}O_6$: C, 60.39; H, 7.43. Found: C, 60.50; H, 7.52.

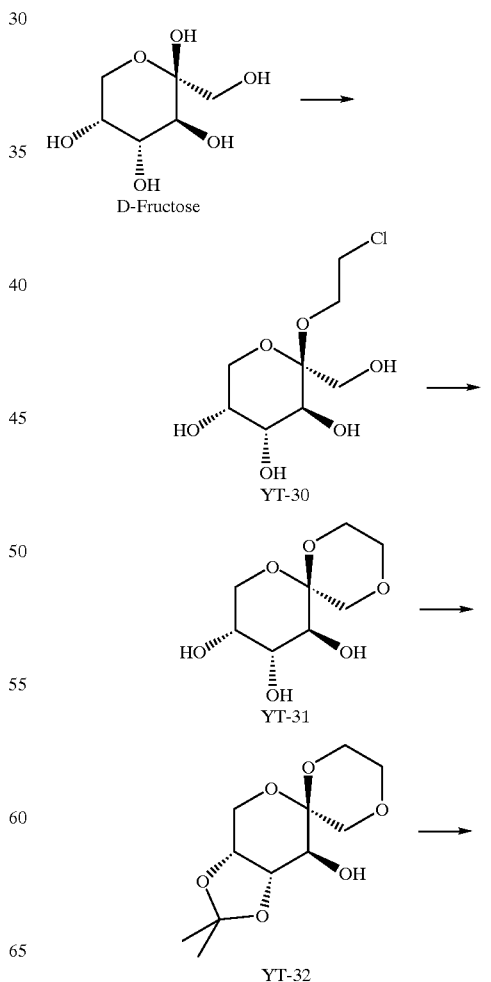

Preparation of Ketone YT-29

To a solution of alcohol YT-5 (5.10 g, 15 mmol) in acetonitrile-water (100 mL, 9:1, v/v) was added DDQ (0.64 g, 3 mmol). After being stirred at room temperature for 3 hours, the reaction mixture was concentrated to a reddish residue. After being washed with ethyl acetate, the residue was dried under vacuum to give a reddish solid (YT-27) (2.19 g) which could be directly used for next reaction.

To a mixture of alcohol YT-27 (2.91 g), 2,2-dimethoxypropane (2.0 mL, 18 mmol), cupric sulfate (5.0 g) and acetone (40 mL) was added con. sulfuric acid (0.06 g). After being stirred for 1.5 hour at room temperature, the reaction mixture was neutralized with triethylamine (1 mL) and filtered. The filtrate was concentrated and purified by flash chromatography (hexane:ether, 10:1 to 3:2) to afford

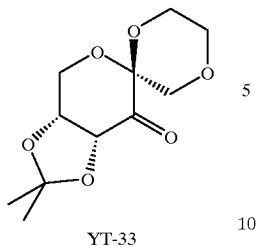

YT-33

Preparation of Ketone YT-33

Perchloric acid (70%) (1 mL) was added to a mixture of alcohol YT-31(10.08 g, 52 mmol) (for preparation see: J. Y. C. Chan, P. P. L. Cheong, L. Hough, and A. C. Richardson, *J. Chem. soc. perkin tTrans. I,* 1985,1447) and 2,2-dimethoxypropane (8.0 mL, 65 mmol) in acetone (100 mL) at 0° C. After being stirred under nitrogen at the temperature overnight, the reaction mixture was neutralized with con. $NH_4OH$ solution, and concentrated. The resulting residue was dissolved in dichloromethane (100 mL), washed with brine, dried with sodium sulfate, concentrated, and purified with flash chromatography (ethyl acetate:hexane, 3:1 to 1:1, v/v) to give alcohol YT-32 as a solid (4.22 g, 35.3%). $^1$H NMR: δ4.25 (dd, J=5.8, 2.3 Hz, 1H), 4.18 (d, 6.7, 1H), 4.13 (d, J=13.7 Hz, 1H), 3.94 (dd, J=13.3, 2.6 Hz, 1H), 3.88 (d, J=11.9 Hz, 1H), 3.80–3.65 (m, 3H), 3.59 (dd, J=11.3, 2.6 Hz, 1H), 3.44 (dd, J=7.1, 7.1), 2.56 (d, J=5.4 Hz, 1H), 1.54 (s, 3H), 1.37 (s, 3H). $^{13}$C NMR: δ109.3, 94.83, 76.51, 73.46, 71.33, 68.89, 65.51, 60.24, 59.78, 27.97, 26.00.

PCC (5.82 g, 27 mmol) was added portionwise over 15 min to a mixture of alcohol YT-32 (2.46 g, 10 mmol) and powdered 3A molecular sieves (11 g) in dichloromethane (50 mL). After being stirred overnight under nitrogen, the reaction mixture was filtered through celite and washed carefully with ether. The filtrate was concentrated and purified by passing through a short silica gel column (hexane:ether, 1:1, v/v) to afford YT-33 as a white solid (2.04 g, 83.6%). $^1$H NMR: δ4.73 (d, J=5.7 Hz, 1H), 4.58 (ddd, J=5.7, 2.0, 1.2 Hz, 1H), 4.24–4.02 (m, 3H), 3.90 (d, J=12.6 Hz, 1H), 3.82–3.59 (m, 4H), 1.45 (s, 3H), 1.38 (s, 3H). $^{13}$C NMR: δ199.3, 110.7, 93.94, 78.72, 75.70, 67.23, 65.58, 60.49, 59.42, 27.36, 26.28. Anal. Calcd. for $C_{11}H_{14}O_6$: C, 54.09; H, 6.60. Found: C, 53.91; H, 6.89.

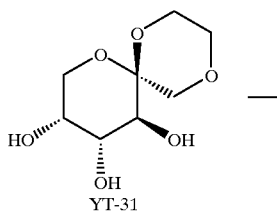

YT-31

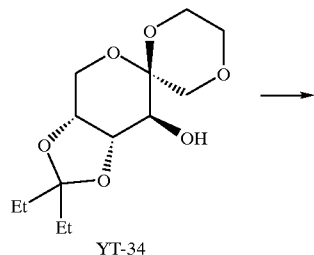

YT-34

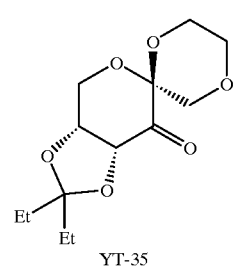

YT-35

Preparation of Ketone YT-35

To a solution of 3-pentanone (3.44 g, 40 mmol) and trimethyl orthoformate (4.4 mL, 4.24 mmol) in methanol (10 mL) was added $TsOH.H_2O$ (0.05 g). After the solution was heated at 50–60° C. for 2 hours (during this time methyl formate formed was distilled off), the bath temperature was raised to 80° C. to distill off the methanol. Upon cooling to room temperature, a solution of alcohol YT-31 (6.18 g, 30 mmol) in THF (100 mL) was added, followed by 4 drops of 70% perchloric acid. After being stirred at room temperature overnight, the reaction mixture was neutralized with con. $NH_4OH$ and concentrated. The resulting residue was dissolved in dichloromethane (200 mL), washed with brine, dried over sodium sulfate, concentrated, and purified by flash chromatography (hexane:ether, 20:1 to 3:2, v/v) to give alcohol YT-34 as a solid (5.08 g, 61.86). $^1$H NMR: δ4.27–3.64 (m, 10H), 3.59 (dd, J=5.8 Hz, 1H), 2.69 (d, J=6.0 Hz, 1H), 1.76 (m, 2H), 1.63 (q, J=7.5, 2H), 0.97 (t, J=7.5 Hz, 3H), 0.90 (t, J=7.5 Hz, 3H). $^{13}$C NMR: δ113.5, 94,77, 76.34, 71,36, 69.22, 65,62, 60,34, 60.18, 30.20, 28.65, 8.651.

PCC (10.52 g, 48.8 mmol) was added portionwise over 15 min to a mixture of alcohol YT-34 (5.00 g, 27.4 mmol) and powdered 3A molecular sieves (8.02 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-35 as a white solid (3.98 g, 79.0%). $^1$H NMR: δ4.67 (dd, J=6.1, 1.1 Hz, 1H), 4.60 (ddd, J=6.1, 2.8, 1.5 Hz, 1H), 4.17 (s, 2 Hz, 1H), 4.05 (dtq, J=11.2, 3.2, 1.5 Hz, 1H), 3.92 (dd, J=12.3, 1.8 Hz, 1H), 3.82–3.58 (m, 4H), 1.64 (m, 4H), 0.91 (m, 6H). $^{13}$C NMR: δ199.2, 114.8, 93.94, 78.18, 75.29, 67.31, 65.58, 60.38, 59.65, 29.87, 29,12, 8.583, 8,389. Anal. Calcd. for $C_{13}H_{20}O_6$: C, 57.34; H, 7.40. Found: C, 57.58; H, 7.45.

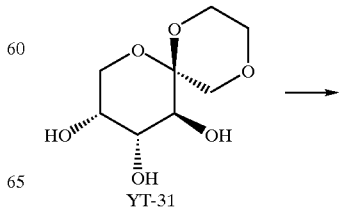

YT-31

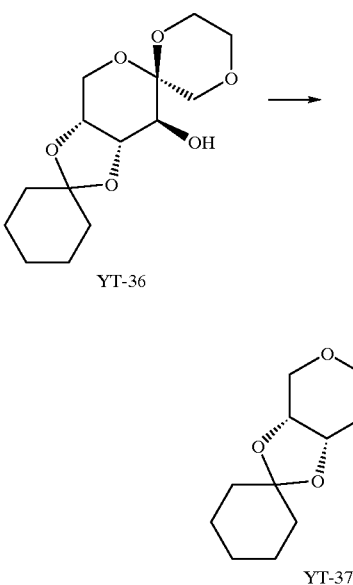

YT-36

YT-37

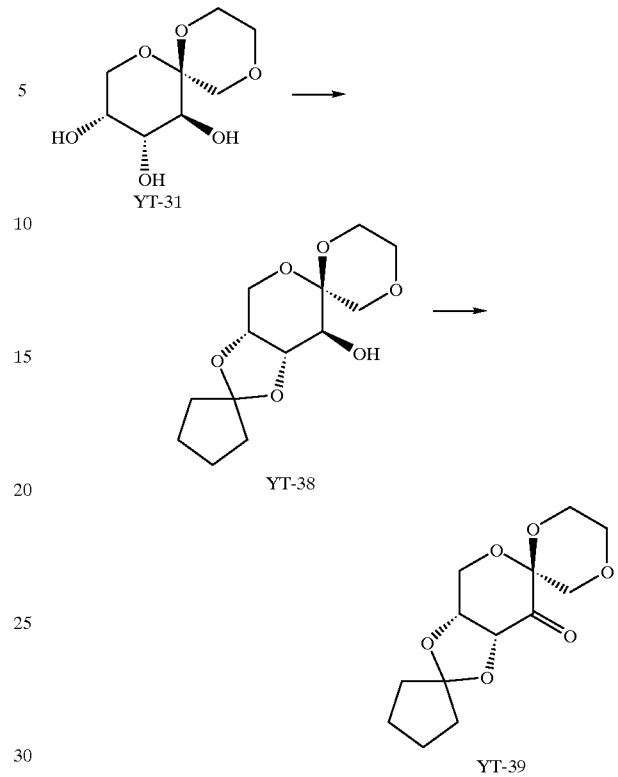

YT-31

YT-38

YT-39

Preparation of Ketone YT-37

To a solution of cyclohexanone (5.88 g, 60 mmol) and trimethyl orthoformate (4.4 mL, 4.24 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-36 as a solid (7.64 g, 66.3%). $^1$H NMR: δ4.24–3.57 (m, 10H), 3.43 (t, J=7.0 Hz, 1H), 2.53 (d, J=7.2 Hz, 1H), 1.76–1.58 (m, 8H), 1.43–1.38 (m, 2H). $^{13}$C NMR: δ110.2, 95.05, 76.24, 73.21, 71.81, 68.95, 65.64, 60.34, 59.96, 37.93, 35.41, 25.11, 24.14, 23.78.

PCC (10.52 g, 48.8 mmol) was added portionwise over 15 min to a mixture of alcohol YT-36 (5.76 g, 20 mmol) and powdered 3A molecular sieves (9.92 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-37 as a white solid (4.98 g, 86.5). $^1$H NMR: δ4.73 (d, J=5.6 Hz, 1H), 4.59 (d, J=5.6 Hz, 1H), 4.19 (d, J=1.4, 2H), 4.10–3.60 (m, 7H), 1.62 (m, 8H), 1.40 (bs, 2H). $^{13}$C NMR: δ199.5, 111.3, 93.93, 78.26, 75,28, 67.25, 65.55, 60.42, 59.53, 36.91, 35.61, 25.07, 24.05, 23.90. Anal. Calcd. for C$_{14}$H$_{20}$O$_6$: C, 59.14; H, 7.09. Found: C, 59.21; H, 7.03.

Preparation of Ketone YT-39

To a solution of cyclopetanone (5.04 g, 60 mmol) and trimethyl orthoformate (4.4 mL, 4.24 g, 40 mmol) in methanol (20 mL) was added TsOH.H$_2$O (0.05 g). After the solution was heated at 50–60° C. for 3 hours (during this time methyl formate formed was distilled off), the bath temperature was raised to 80° C. to distill off the methanol. Upon cooling to room temperature, a solution of alcohol YT-31 (8.24 g, 40 mmol) in THF (100 mL) was added, followed by 4 drops of 70% perchloric acid. After being stirred at room temperature for 5 hours, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-38 as a solid (5.97 g, 51.8%).

PCC (9.92 g, 46 mmol) was added portionwise over 15 min to a mixture of alcohol YT-38 (5.48 g, 20 mmol) and powdered 3A molecular sieves (20 g) in dichloromethane (100 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-39 as a white solid (4.29 g, 78%). $^1$H NMR: δ4.73 (d, J=5.8 Hz, 1H), 4.46 (ddd, J=5.7, 1.8, 0.6 Hz, 1H), 4.25–4.03 (m, 8H), 2.05–1.61 (m, 8H). $^{13}$C NMR: δ198.8, 120.3, 93.85, 78.97, 75.40, 67.16, 65.55, 60.45, 59.34, 37.47, 23.71, 23.40. Anal. Calcd. for C$_{13}$H$_{18}$O$_6$: C, 57.77; H, 6.71. Found: C, 57.62; H, 6.81.

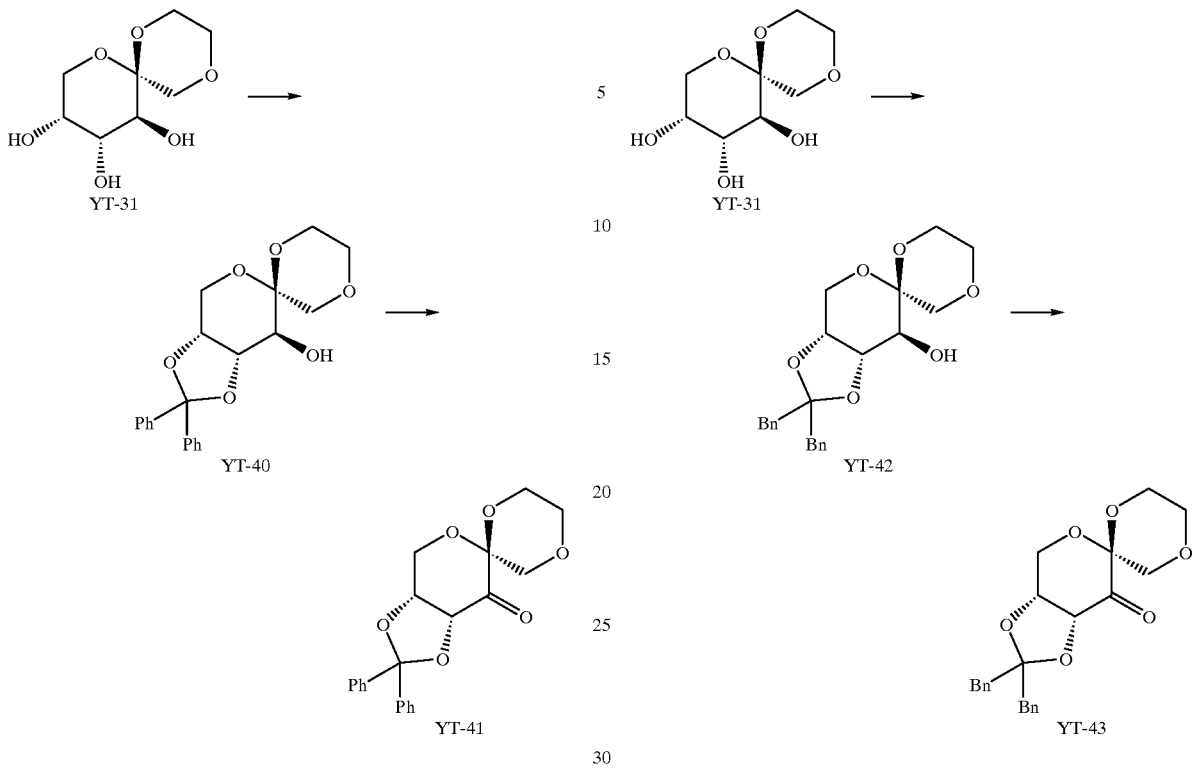

Preparation of ketone YT-41

To a solution of benzophenone (4.86 g, 30 mmol) and trimethyl orthoformate (3.1 mL, 30 mmol) in methanol (20 mL) was added TsOH.H$_2$O (0.02 g). After the solution was heated at 50–60° C. for 3 hours (during this time methyl formate formed was distilled off), the bath temperature was raised to 100° C. to distill off the methanol. Upon cooling to room temperature, a solution of alcohol YT-31 (6.18 g, 30 mmol) in THF (150 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-40 as a solid (7.24 g, 67%). $^1$H NMR: δ7.55–7.20 (m, 10H), 4.37–3.54 (m, 10H), 3.43 (dd, J=7.1, 7.1 Hz, 1H), 2.37 (d, J=7.4 Hz, 1H). $^{13}$C NMR: δ143.3, 142.7, 128.3, 128.2, 126,3, 126,2, 126.1, 109.6, 96.02, 77.42, 74.10, 71.01, 69.08, 65.68, 60.44, 59.78.

PCC (4.0 g, 18.6 mmol) was added portionwise over 15 min to a mixture of alcohol YT-40 (2.79 g, 8.1 mmol) and powdered 3A molecular sieves (80 g) in dichloromethane (80 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-41 as a white solid (1.43 g, 51%). $^1$H NMR: δ7.6–7.2 (m, 10H), 4.79 (d, J=6.6 Hz, 1H), 4.53 (dd, J=6.4, 1.8 Hz, 1H), 4.32 (d, J=13.4, 1H), 4.18 (dd, J=13.4, 2.4 Hz, 1H), 4.07 (dt, J=11.2, 3.2 Hz, 1H), 3.85 (d, J=12.4 Hz, 1H), 3.80–3.57 (m, 4H); $^{13}$C NMR: δ197.8, 141.9, 140.9, 128.8, 128.5, 128.4, 128.2, 126.5, 110.8, 94.17, 78.58, 75.63, 67.47, 65.60, 60.44, 59.55. Anal. Calcd. for C$_{21}$H$_{20}$O$_6$: C, 68.47; H, 5.47. Found: C, 68.34; H, 5.85.

Preparation of ketone YT-43

To a solution of 1,3-diphenylacetone (2.1 g, 10 mmol) and trimethyl orthoformate (1.2 mL, 11 mmol) in methanol (10 mL) was added TsOH.H$_2$O (0.01 g). After the solution was heated at 50–60° C. for 3 hours (during this time methyl formate formed was distilled off), the bath temperature was raised to 90° C. to distill off the methanol. Upon cooling to room temperature, a solution of alcohol YT-31 (3.10 g, 15 mmol) in THF (100 mL) was added, followed by 3 drops of 70% perchloric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 10:1 to 5:2, v/v) to give alcohol YT-42 (2.36 g, 59.2%). $^1$H NMR: δ7.30 (m, 10H), 3.98 (d, 13.6, 1H), 3.90 (t, J=6.6 Hz, 1H), 3.84 (dt, J=11.4, 3.2 Hz, 1H), 3.70–3.52 (m, 4H), 3.45 (dd, J=11.4, 2.6 Hz, 1H), 3.16 (d, J=11.7 Hz, 1H), 3.07–2.95 (m, 3H), 2.91 (d, J=13.6 Hz, 1H), 1.87 (dd, J=8.0, 7.1 Hz, 1H), 1.72 (d, J=7.9, 1H). $^{13}$C NMR: δ136.7, 136.3, 131.7, 130.8, 128.4, 128.1, 126.8, 111.5, 94.76, 77.47, 73.86, 70.51, 68.46, 65,54, 60,21, 59.49, 45.49, 44,53.

PCC (2.34 g, 10.4 mmol) was added portionwise over 15 min to a mixture of alcohol YT-42 (1.8 g, 4.5 mmol) and powdered 3A molecular sieves (5.0 g) in dichloromethane (50 mL). After being stirred for 3 hours under nitrogen, the reaction mixture was filtered through celite and washed carefully with ether. The filtrate was concentrated and purified by passing through a short silica gel column (hexane:ether, 1:1, v/v) to afford YT-43 as a solid (1.68 g, 93%). $^1$H NMR: δ7.45–7.20 (m, 10H), 4.45 (d, J=6.3 Hz, 1H), 4.07–3.61 (m, 8H), 3.54 (dd, J=11.1, 2.4 Hz, 1H), 2.98 (d, J=13.8 Hz, 1H), 2.93 (d, J=13.8 Hz, 1H), 2.91 (d, J=13.9 Hz, 1H), 2.82 (d, J=13.9 Hz, 1H). $^{13}$C NMR: δ198.9, 136.2, 136.0, 131.0, 130.9, 128.2, 128.1, 126.7, 112.5, 93.63, 79.03, 75.45, 66.99, 65.39, 60.22, 59.23, 46.13, 43.63, Anal.

Calcd. for $C_{23}H_{24}O_6$: C, 69.68; H, 6.10. Found: C, 69.46; H, 5.88.

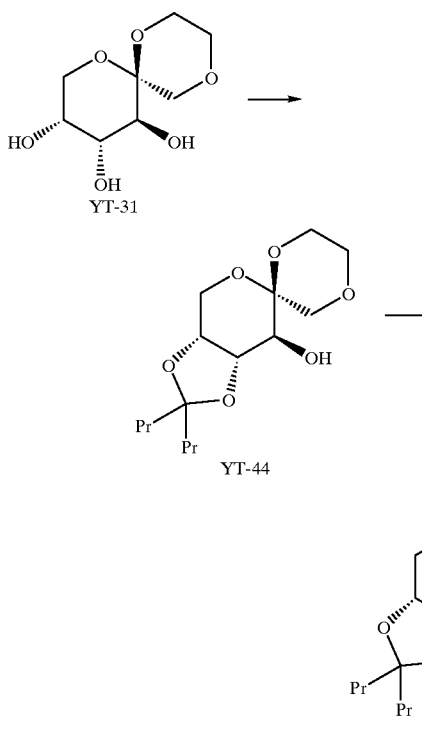

Preparation of Ketone YT-45

To a solution of 4-heptanone (11.4 g, 100 mmol) and trimethyl orthoformate (4.24 g, 40 mmol) in methanol (50 mL) was added TsOH.H$_2$O (0.01 g). After the solution was heated at 50–70° C. for 2 hours (during this time methyl formate formed was distilled off), the bath temperature was raised to 100° C. to distill off the methanol. Upon cooling to room temperature, a solution of alcohol YT-31 (6.18 g, 30 mmol) in dioxane (60 mL) was added, followed by cupric sulfate (6.0 g) and 3 drops of con. sulfuric acid. After being stirred at room temperature overnight, the reaction mixture was neutralized with con. NH$_4$OH and concentrated. The resulting residue was dissolved in dichloromethane (150 mL), washed with brine, dried over sodium sulfate, concentrated, and purified by flash chromatography (hexane:ether, 50:1 to 3:1, v/v) to give alcohol YT-44 as a syrup (5.56 g, 46.0%). $^1$H NMR: δ4.24 (dd, J=6.2, 2.7 Hz, 1H), 4.18 (dd, J=6.3, 6.3 Hz, 1H), 4.07–4.00 (m, 2H), 3.91 (dd, J=13.4, 2.7 Hz, 1H), 3.86 (dd, J=11.7, 3.5 Hz, 1H), 3.80–3.65 (m, 3H),3.59 (dd, J=11.2, 3.5, 1H), 3.46 (dd, J=5.9, 5.9 Hz, 1H), 2.33 (bs, 1H), 1.73–1.31 (m, 4H), 0.93 (t, J=7.2 Hz, 3H), 0.91 (t, J=7.2 Hz, 3H). $^{13}$C NMR: δ112.9, 94.77, 76.31, 71.45, 69.46, 65.76, 60.49, 60.34, 40.45, 38.92, 17.82, 17.68, 14.61.

PCC (9.12 g, 42.3 mmol) was added portionwise over 15 min to a mixture of alcohol YT-44 (4.73 g, 15.7 mmol) and powdered 3A molecular sieves (18.24 g) in dichloromethane (100 mL). After being stirred for 3 h under nitrogen, the reaction mixture was filtered through celite and washed carefully with ether. The filtrate was concentrated and purified by passing through a short silica gel column (hexane:ether, 1:1, v/v) to afford YT-45 as a syrup (3.89 g, 83%). $^1$H NMR: δ4.66 (d, J=6.1 Hz, 1H), 4.50 (ddd, J=5.2, 1.5, 1.5 Hz, 1H), 4.17 (d, J=1.5 Hz, 2H), 4.06 (dt, J=11.1, 3.2 Hz, 1H), 3.92 (d, J=12.4 Hz, 1H), 3.82–3.60 (m, 4H), 1.62–1.26 (m, 8H), 0.912 (t, J=7,3 Hz, 3H), 0.907 (t, J=7.2 Hz, 3H). $^{13}$C NMR: δ199.2, 114.1, 94.03, 78.09, 75.26, 67.42, 65.62, 60.62, 59.74, 39.89, 39.22, 17.65, 17.44, 14.55. Anal. Calcd. for $C_{13}H_{24}O_6$: C, 69.68; H, 6.10. Found: C, 69.46; H, 5.88.

Preparation of Ketone YT-48 t-Butyldimethylsilyl chloride (22.61 g, 150 mmol) was added to a mixture alcohol YT-30 (36.32 g, 150 mmol), DMAP (1.0 g), and imidazole (10.8 g, 150 mmol) in DMF (200 mL) at room temperature. After being stirred overnight, the reaction mixture was concentrated to give a residue. The residue was treated with ethyl acetate (400 mL). After filtration, the filtrate was dried over sodium sulfate, concentrated to give alcohol YT-46 as a syrup.

The syrup was mixed with acetone (800 mL), 2,2-dimethoxypropane (70 mL, mmol), cupric sulfate (180 g), and con. sulfuric acid (2.8 g). After being stirred at room temperature for 40 min, the reaction mixture was neutralized with triethylamine, filtered, and concentrated. The resulting residue was dissolved in ethyl acetate (300 mL), washed with brine, dried over sodium sulfate, concentrated, and purified with flash chromatography (hexane:ether, 100:0 to 10:1, v/v) to give alcohol YT-47 as a syrup (21.28 g, 35.8%). $^1$H NMR: δ4.34 (dd, J=6.2, 6.0 Hz, 1H), 4.25 (ddd, J=6.2, 2.4, 0.9 Hz, 1H), 4.05 (dd, J=13.1, 2.4 Hz, 1H), 3.96 (dd, J=6.0, 2.8 Hz, 1H), 3.89–3.64 (m, 7H), 3.20 (d, J=2.5 Hz, 1H), 1.52 (s, 3H), 1.36 (s, 3H), 0.90 (s, 9H), 0.095 (s, 3H), 0.085 (s, 3H). $^{13}$C NMR: δ109.3, 98.12, 75.45, 72.75, 70.45, 64.30, 61.47, 61.05, 43.33, 27.55, 25,99, 25.62, 18.36, −5.34, −5.39.

PCC (27.82 g, 129 mmol) was added portionwise over 15 min to a mixture of alcohol YT-47 (20.25 g, 51 mmol) and powdered 3A molecular sieves (44.5 g) in dichloromethane (100 mL). After being stirred for 3 h under nitrogen, the reaction mixture was filtered through celite and washed carefully with ether. The filtrate was concentrated and the purified by passing through a short silica gel column (hexane:ether, 1:1, v/v) to afford YT-48 as a syrup (15.86 g, 78.7%). $^1$H NMR: δ4.85 (d, J=5.8 Hz, 1H), 4.59 (dd, J=5.8, 2.1 Hz, 1H), 4.38 (dd, J=13.4, 2.1 Hz, 1H), 4.08–3.70 (m. 7H), 1.48 (s, 3H), 1.38 (s, 3H), 0.87 (s, 9H), 0.092 (s, 3H), 0.085 (s, 3H). $^{13}$C NMR: δ198.7, 110.5, 99.53, 78.79, 76.12, 63.07, 61.53, 60.01, 43.29, 27.36, 26.24, 25.99, 18.47, −5.29, −5.41. Anal. Calcd. for $C_{17}H_{29}O_6ClSi$: C, 51.69; H, 7.91. Found: C, 51.90; H, 8.03.

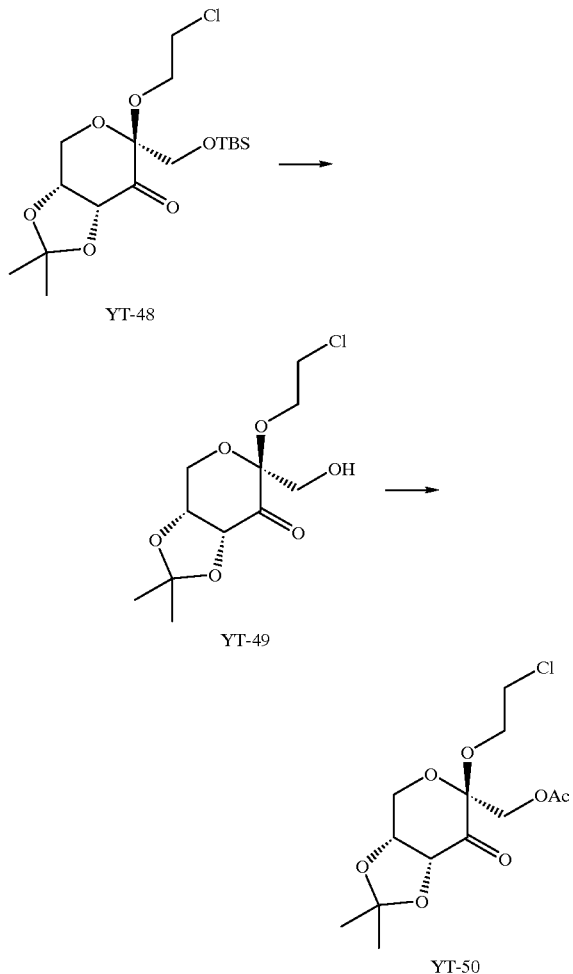

Preparation of Ketone YT-49 and Ketone YT-50

To a solution of ketone YT-48 (1.98 g,50 mmol) in pyridine (2 mL) and water (2 mL) was added TBAF (10 mL, 1 M in THF). After being stirred at room temperature for 15 min, the reaction mixture was poured into water (10 mL), extracted with chloroform, washed with brine, dried over sodium sulfate, concentrated, and purified with a flash chromatography (hexane:ether, 10:1 to 1:1, v/v) to give ketone YT-49 (0.90 g, 64%). IR: 3511 cm$^{-1}$. $^1$H NMR: δ4.82 (d, J=5.6 Hz, 1H), 4.58 (ddd, J=5.6, 2.2, 1.0 Hz, 1H), 4.50 (dd, J=13.3, 2.2 Hz, 1H), 4.12 (d, J=13.3 Hz, 1H), 4.03 (dt, J=10.5, 4.3 Hz, 1H), 3.96–3.70 (m, 5H), 3.75 (dd, J=4.4, 1.0 Hz, 1H), 3.73 (d, J=4.3 Hz, 1H), 2.23 (bs, 1H), 1.46 (s, 3H), 1.40 (s, 3H). $^{13}$C NMR: δ201.4, 110.6, 98.91, 78.11, 75.63, 62.84, 61.08, 59.67, 43.15, 27.36, 26.21. Anal. Calcd. for $C_{11}H_{17}O_6Cl$: C, 47.1; H, 6.1. Found: C, 46.98; H, 6.18.

To a mixture of ketone YT-49 (1.40 g, 5 mmol), DMAP (0.20 g), and pyridine (6 mL) in dichloromethane (15 mL) was added acetic anhydride (4.0 mL, mmol). After being stirred overnight, the reaction mixture was poured into ice-water (20 mL), extracted with dichloromethane, washed with brine, dried over sodium sulfate, concentrated, and purified with a flash chromatography to give ketone YT-50 as a syrup (0.89 g, 49.2%). IR: 1752 cm−1. $^1$H NMR: δ4.82 (d, J=5.9 Hz, 1H), 4.60 (ddd, J=5.9, 2.0, 0.9 Hz, 1H), 4.43 (d, J=12.3 Hz, 1H), 4.40 (dd, J=13.5, 2.0 Hz, 1H), 4.32 (d, J=12.3 Hz, 1H), 4.13 (d, J=13.5 Hz, 1H), 3.98–3.70 (m, 4H), 2.08 (s, 3H), 1.47 (s, 3H), 1.40 (s, 3H). $^{13}$C NMR: δ198.1, 170.3, 110.8, 98.81, 78.05, 75.63, 62.87, 60.76, 60.00, 42.94, 27.24, 26.21, 20.94. Anal. calcd. for $C_{13}H_{19}O_7Cl$: C, 48.38; H, 5.93. Found: C, 48.45; H, 6.23.

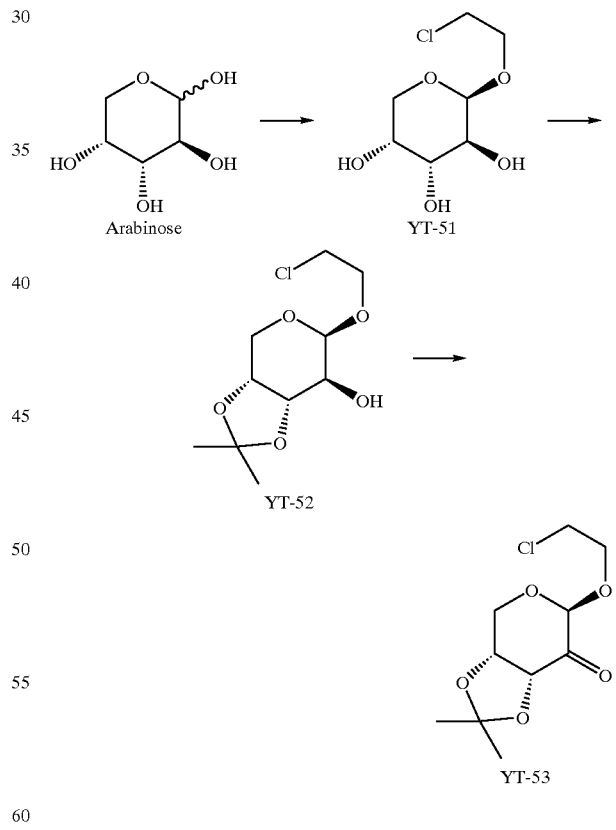

Preparation Of Ketone YT-53

D-Arabinose (10 g, 66.7 mmol) was added to 2-chloroethanol (50 mL) (containing 1.5 mL of AcCl). After being stirred at 50° C. for 24 hours, the reaction mixture was cooled down in a refrigerator. The resulting suspension was filtered and the cake was washed with ethanol to give alcohol YT-51 as a white solid (7.42 g, 57.8%).

Con. sulfuric acid (0.1 g) was added to a mixture of 2-chloroethyl arabinoside YT-51 (6.02 g, 31 mmol), 1,1-dimethoxypropane (5 mL, 4.25 g, 41 mmol), and $CuSO_4$ (10 g) in acetone (100 mL). After being stirred overnight, the reaction mixture was filtered. The filtrate was concentrated and purified by chromatography (hexane:ether, 20:1 to 2:1, v/v) to give alcohol YT-52 as a white solid (5.87 g, 81%). $^1H$ NMR: $\delta$4.87 (d, J=3.9 Hz, 1H), 4.27–3.67 (m, 10H), 2.29 (bs, 1H), 1.53 (s, 3H), 1.37 (s, 3H). $^{13}C$ NMR: $\delta$109.4, 98.17, 75.89, 72,98, 70.02, 68.46, 60.14, 43.01, 28.02, 26.04.

PCC (13.58 g, 63 mmol) was added portionwise over 15 min to a mixture of alcohol YT-52 (5.87 g, 23.2 mmol) and powdered 3A molecular sieves (26 g) in dichloromethane (100 mL). After being stirred for 3 hours under nitrogen, the reaction mixture was filtered through celite and washed carefully with ether. The filtrate was concentrated and the purified by passing through a short silica gel column (hexane:ether, 1:1, v/v) and subsequent recrystallization (diisopropyl ether) to give ketone YT-53 as a white solid (1.63 g, 28%). $^1H$ NMR: $\delta$4.87 (s, 1H), 4.72 (d, J=5.6 Hz, 1H), 4.56 (ddd, J=5.6, 2.1, 0.9 Hz, 1H), 4.39 (dd, J=13.4, 2.1 Hz, 1H), 4.10 (d, J=13.4 Hz, 1H), 4.03 (dt, J=11.0, 5.9 Hz, 1H), 3.85 (dt, J=11.0, 4.9 Hz, 1H), 3.70 (dd, J=5.9, 4.9 Hz, 2H), 1.47 (s, 3H), 1,40 (s, 3H). $^{13}C$ NMR: $\delta$198.5, 110.8, 100.1, 77.66, 75.52, 68.81, 59.06, 42.67, 27.36, 26.31. Anal. Calcd. for $C_{10}H_{15}O_5Cl$: C, 47.91; H, 6.03. Found: C, 48.00; H, 6.24.

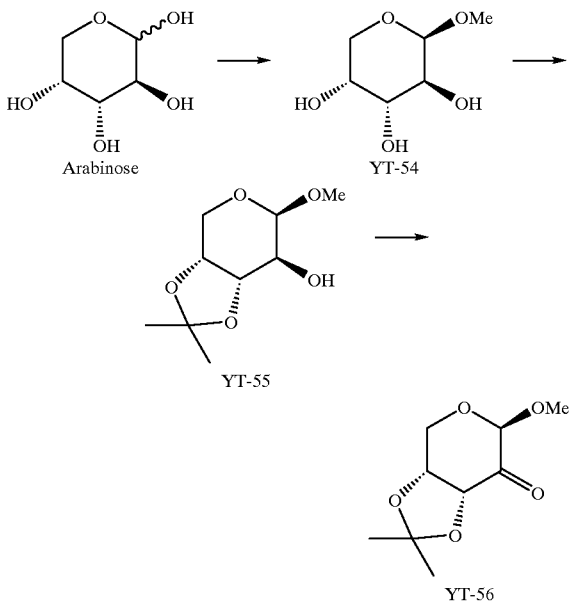

Preparation of Ketone YT-56

Ketone YT-56 was prepared based on a reported procedure (M. Bennett, C. B. Gill, G. Pattenden, A. J. Shucker, and A. Stapleton, *J. Chem. soc. Perkin Trans. I*, 1991, 929). $^1H$ NMR: $\delta$4.71 (s, 1H), 4.69 (d, J=5.7 Hz, 1H), 4.54 (ddd, J=5.7, 1.9, 1.3 Hz, 1H), 4.24 (ddd, J=12.7, 1.9, 0.8 Hz, 1H), 4.08 (ddd, 12.7, 1.3, 0.8, 1H), 3.49 (s, 3H), 1.47 (s, 3H), 1.40 (s, 3H). $^{13}C$ NMR: $\delta$199.0, 110.7, 101.1, 78.70, 75.61, 58.60, 55.93, 27.36, 26.32.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method of producing an enantiomerically enriched epoxide from an olefin comprising the steps of:

(a) adding an oxidizing agent to a reaction solution comprising a chiral cyclic enantiomerically enriched ketone and an olefin under conditions effective to generate an enantiomerically enriched epoxide; and (b) separating said enantiomerically enriched epoxide from said reaction solution;

wherein said chiral cyclic enantiomerically enriched ketone is selected from the group consisting of compounds of the formula:

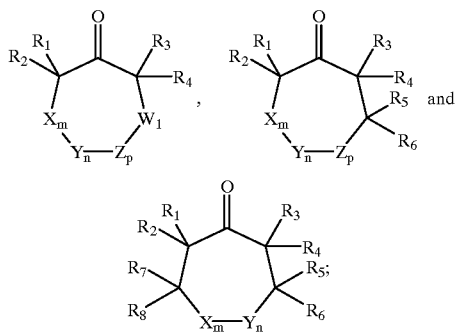

wherein

W, X, Y and Z are independently $CR_9R_{10}$, or O;

l, m, n and p are independently an integer from 0 to 3; and $R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms.

2. The method of claim 1, wherein said oxidizing agent is selected from the group consisting of peracids, hydrogen peroxide, sodium hypochlorite, potassium peroxomonosulfate, sodium perborate and hypofluoride (HOF).

3. The method of claim 2, wherein said oxidizing agent is potassium peroxomonosulfate.

4. The method of claim 1, wherein said chiral enantiomerically enriched ketone is a compound of the formula:

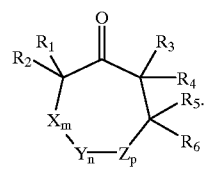

5. The method of claim 4, wherein m is 0, Y is O or $CR_9R_{10}$, n and p are 1, and Z is $CR_9R_{10}$.

6. The method of claim 5, wherein two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms.

7. The method of claim 6, wherein $R_1$ and $R_2$ are linked to form a moiety of the formula:

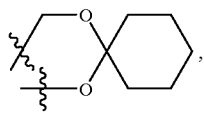

—O—C(CH$_2$CH$_3$)$_2$—O—CH$_2$— or —O—C(CH$_3$)$_2$—O—CH$_2$—.

8. The method of claim 7, wherein R$_1$ and R$_2$ are linked to form a moiety of the formula:

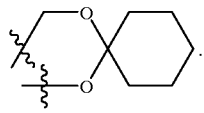

9. The method of claim 7, wherein R$_1$ and R$_2$ are linked to form a moiety of the formula —O—C(CH$_3$)$_2$—O—CH$_2$— or —O—C(CH$_2$CH$_3$)$_2$—O—CH$_2$—.

10. The method of claim 6, wherein R$_3$ and R$_6$ are linked to form a moiety of the formula —O—C(CH$_3$)$_2$—O— or —O—C(CH$_2$CH$_3$)$_2$—O—.

11. The method of claim 5, wherein R$_4$, R$_5$, R$_9$ and R$_{10}$ are independently hydrogen, halide, or sulfinyl, alkoxy, carboxyl or alkyl groups having 1 to about 20 carbon atoms.

12. The method of claim 5 wherein said chiral cyclic enantiomerically enriched ketone is derived from a group consisting of (D)-fructose, (L)-fructose, (D)-arabinose, (L)-arabinose and (L)-sorbose.

13. The method of claim 1, wherein said chiral cyclic enantiomerically enriched ketone is of the formula:

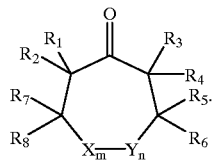

14. The method of claim 13, wherein m is 0, Y is CR$_9$R$_{10}$, and n is 1.

15. The method of claim 14 wherein two or more R$_1$, R$_2$, R$_3$, R$_4$, R$_5$, R$_6$, R$_7$, R$_8$, R$_9$ and R$_{10}$ are linked to form 3 to about 10 membered cyclic moiety containing 1 to about 20 carbon atoms.

16. The method of claim 13, wherein R$_1$ and R$_7$ are linked to form a moiety of the formula —O—C(CH$_3$)$_2$—O— or —O—C(CH$_2$CH$_3$)$_2$—O—.

17. The method of claim 13, wherein R$_3$ and R$_6$ are linked to form a moiety of the formula —O—C(CH$_3$)$_2$—O— or —O— C(CH$_2$CH$_3$)$_2$—O—.

18. The method of claim 13, wherein R$_1$ and R$_7$ are linked to form a moiety of the formula —C(CH$_3$)$_2$—.

19. The method of claim 14, wherein R$_4$, R$_5$, R$_9$ and R$_{10}$ are independently hydrogen, halide or alkoxy, sulfinyl, carboxyl or alkyl groups having 1 to about 20 carbon atoms.

20. The method of claim 13, wherein said chiral cyclic enantiomerically enriched ketone is derived from quinic acid.

21. The method of claim 1, wherein said step of adding said oxidizing agent to said reaction solution further comprises adding a base to said reaction solution.

22. The method of claim 21, wherein said base is added at a rate effective to maintain the pH of said reaction mixture at from about 10 to about 14.

23. The method of claim 22, wherein said base is selected from the group consisting of potassium carbonate, potassium bicarbonate, sodium bicarbonate, sodium carbonate, sodium hydroxide, sodium borate, sodium phosphate, potassium phosphate and potassium hydroxide.

24. The method of claim 1, wherein said step of producing said epoxide from said olefin is conducted at pH of from at least about 10 to at least about 12.

25. The method of claim 1, wherein said step of producing said epoxide from said olefin is conducted at a temperature of less than about 0° C.

26. The method of claim 1, wherein said solution comprising said chiral cyclic enantiomerically enriched ketone and said olefin comprises a solvent selected from the group consisting of acetonitrile, dimethoxymethane, dimethoxyethane, water, dimethyl formamide, dioxane, dichloromethane, alcohol and mixtures thereof.

27. The method of claim 1, wherein said separated epoxide has at least about 80%ee.

28. A method for asymmetrically epoxidizing an olefin comprising the steps of:

(a) contacting an olefin with a chiral cyclic enantiomerically enriched dioxirane in a solution under conditions effective to generate an enantiomerically enriched epoxide, said dioxirane derived from a chiral cyclic enantiomerically enriched ketone selected from the group consisting of compounds of the formula:

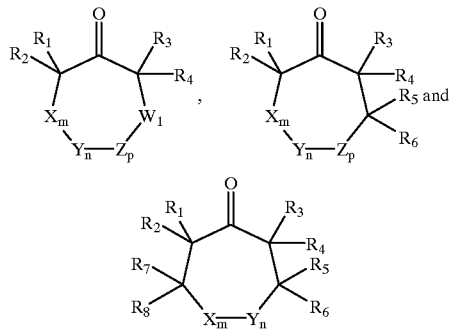

wherein

W, X, Y and Z are independently CR$_9$R$_{10}$, or O;

l, m, n and p are independently an integer from 0 to 3; and

R$_1$, R$_2$, R$_3$, R$_4$, R$_5$, R$_6$, R$_7$, R$_8$, R$_9$ and R$_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more R$_1$, R$_2$, R$_3$, R$_4$, R$_5$, R$_6$, R$_7$, R$_8$, R$_9$ and R$_{10}$ are linked to for about 10 membered cyclic moiety containing 1 to about 20 carbon atoms; and (b) separating said epoxide from said solution.

29. The method of claim 28, wherein said dioxirane is generated in situ by a reaction of said chiral cyclic enantiomerically enriched ketone and an oxidizing agent selected from the group consisting of peracids, hydrogen peroxide, sodium hypochlorite, potassium peroxomonosulfate, sodium perborate and hypofluoride (HOF).

30. The method of claim 28, wherein said chiral cyclic enantiomerically enriched ketone is a compound of the formula:

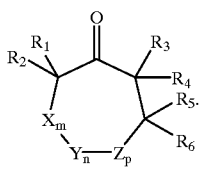

31. The method of claim 30, wherein m is 0, Y is O or $CR_9R_{10}$, n and p are 1, and Z is $CR_9R_{10}$.

32. The method of claim 31, wherein two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms.

33. The method of claim 30, wherein $R_1$ and $R_2$ are linked to form a moiety of the formula:

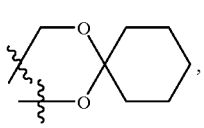

—O—C(CH$_2$CH$_3$)$_2$—O—CH$_2$— or —O—C(CH$_3$)$_2$—O—CH$_2$—.

34. The method of claim 33, wherein $R_1$ and $R_2$ are linked to form a moiety of the formula:

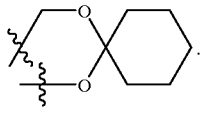

35. The method of claim 33, wherein $R_1$ and $R_2$ are linked to form a moiety of the formula —O—C(CH$_3$)$_2$—O—CH$_2$— or —O—C(CH$_2$CH$_3$)$_2$—CH$_2$—.

36. The method of claim 30, wherein $R_3$ and $R_6$ are linked to form a moiety of the formula —O—C(CH$_3$)$_2$—O— or —O—C(CH$_2$CH$_3$)$_2$—O—.

37. The method of claim 31, wherein $R_4$, $R_5$, $R_9$ and $R_{10}$ are independently hydrogen, halide, or sulfinyl, alkoxy, carboxyl or alkyl groups having 1 to about 20 carbon atoms.

38. The method of claim 28, wherein said chiral cyclic enantiomerically enriched ketone is of the formula:

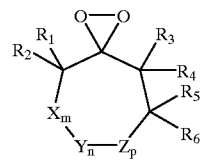

39. The method of claim 38, wherein m is 0, Y is $CR_9R_{10}$, and n is 1.

40. The method of claim 39, wherein two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms.

41. The method of claim 38, wherein $R_1$ and $R_7$ are linked to form a moiety of the formula —O—C(CH$_3$)$_2$—O— or —O—C(CH$_2$CH$_3$)$_2$—O—.

42. The method of claim 38, wherein $R_3$ and $R_6$ are linked to form a moiety of the formula —O—C(CH$_3$)$_2$—O— or —O—C(CH$_2$CH$_3$)$_2$—O—.

43. The method of claim 39, wherein $R_4$, $R_5$, $R_9$ and $R_{10}$ are independently hydrogen, halide, or sulfinyl, alkoxy, sulfonyl, carboxyl or alkyl groups having 1 to about 20 carbon atoms.

44. The method of claim 38, wherein $R_1$ and $R_7$ are linked to form a moiety of the formula —C(CH$_3$)$_2$—.

45. The method of claim 28, wherein said step of contacting said olefin with said chiral cyclic enantiomerically enriched dioxirane is conducted in a solution having pH of from about 10 to about 12.

46. The method of claim 28, wherein said step of contacting said olefin with said chiral cyclic enantiomerically enriched dioxirane is conducted at a temperature of less than about 0° C.

47. The method of claim 28, wherein said step of contacting said olefin with said chiral cyclic enantiomerically enriched dioxirane is conducted in a solvent selected from the group consisting of acetonitrile, dimethoxymethane, dimethoxyethane, water, dimethyl formamide, dioxane, dichloromethane, alcohol and mixtures thereof.

48. The method of claim 28, wherein said step of contacting said olefin with said chiral cyclic enantiomerically enriched dioxirane provides at least about 80%ee.

49. A chiral cyclic enantiomerically enriched dioxirane compound of the formula:

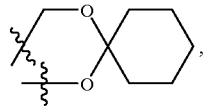

wherein

X, Y and Z are independently $CR_9R_{10}$, or O;

m, n and p are independently an integer from 0 to 3; and $R_1$, $R_2$, $R_3$, $R_4$, $R_5$, $R_6$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms.

50. The compound of claim 49, wherein two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms.

51. The compound of claim 49, wherein $R_1$ and $R_2$ are linked to form a moiety of the formula:

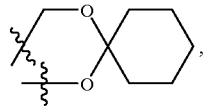

—O—C(CH$_2$CH$_3$)$_2$—O—CH$_2$— or —O—C(CH$_3$)$_2$—O—CH$_2$—.

52. The compound of claim 49, wherein $R_3$ and $R_6$ are linked to form a moiety of the formula —O—C(CH$_3$)$_2$—O— or —O—C(CH$_2$CH$_3$)$_2$—O—.

53. The compound of claim 50, wherein $R_4$, $R_5$, $R_9$ and $R_{10}$ are independently hydrogen, halide, or sulfinyl, alkoxy, carboxyl or alkyl groups having 1 to about 20 carbon atoms.

54. The compound of claim 51, wherein $R_1$ and $R_2$ are linked to form a moiety of the formula:

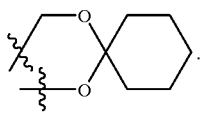

55. The compound of claim 51, wherein $R_1$ and $R_2$ are linked to form a moiety of the formula —O—C(CH$_3$)$_2$—O—CH$_2$— or —O—C(CH$_2$CH$_3$)$_2$—O—C$_2$—.

56. A chiral cyclic enantiomerically enriched dioxirane compound of the formula:

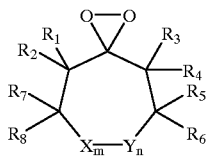

wherein

X and Y are independently CR$_9$R$_{10}$, or O;

m and n are independently an integer from 0 to 3; and $R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms.

57. The compound of claim 56, wherein in is 0, Y is CR$_9$R$_{10}$, and n is 1.

58. The compound of claim 57, wherein two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms.

59. The compound of claim 56, wherein $R_1$ and $R_7$ are linked to form a moiety of the formula —O—C(CH$_3$)$_2$—O— or —C(CH$_2$CH$_3$)$_2$—O—.

60. The compound of claim 56, wherein $R_3$ and $R_6$ are linked to form a moiety of the formula —O—C(CH$_3$)$_2$—O— or —O—C(CH$_2$CH$_3$)$_2$—O—.

61. The compound of claim 57, wherein $R_4$, $R_5$, $R_9$ and $R_{10}$ are independently hydrogen, halide, or sulfinyl, alkoxy, sulfonyl, carboxyl or alkyl groups having 1 to about 20 carbon atoms.

62. The compound of claim 56, wherein $R_1$ and $R_7$ are linked to form a moiety of the formula —C(CH$_3$)$_2$—.

63. The method of producing an enantiomerically enriched epoxide from an olefin comprising the steps of:

(a) adding an oxidant comprising potassium peroxomonosulfate to a reaction solution comprising an olefin and a chiral cyclic enantiomerically enriched ketone of the formula:

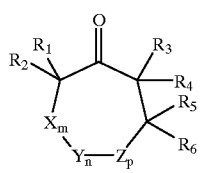

wherein m is 0, Y is O, n and p are 1, and Z is CR$_9$R$_{10}$; and $R_1$, $R_2$, $R_3$, $R_4$, $R_5$, $R_6$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms;

at a temperature of less than about 0° C. and under conditions effective to generate an enantiomerically enriched epoxide; and (b) separating said enantiomerically enriched epoxide from said reaction solution.

64. The method of claim 63, wherein two or more $R_1$, $R_2$, $R_3$, $R_4$, $R_5$, $R_6$, $R_9$ and $R_{10}$ are linked to form 3 to about 10 membered cyclic moiety containing 1 to about 20 carbon atoms.

65. The method of claim 63, wherein $R_1$ and $R_2$ are linked to form a moiety of the formula:

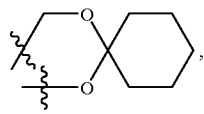

—O—C(CH$_2$CH$_3$)$_2$—O—CH$_2$— or —O—C(CH$_3$)$_2$—O—CH$_2$—;

and $R_3$ and $R_6$ are linked to form a moiety of the formula —O—C(CH$_3$)$_2$—O— or —O—C(CH$_2$CH$_3$)$_2$—O—.

66. The method of claim 65, wherein $R_1$ and $R_2$ are linked to form a moiety of the formula —O—C(CH$_3$)$_2$—O—CH$_2$—, and $R_3$ and $R_6$ are linked to form a moiety of the formula —O—C(CH$_3$)$_2$—O—.

67. The method of claim 63, wherein $R_4$, $R_5$, $R_9$ and $R_{10}$ are independently hydrogen, halide, or sulfinyl, alkoxy, carboxyl or alkyl groups having 1 to about 20 carbon atoms.

68. The method of claim 63, wherein said step of adding said potassium peroxomonosulfate solution to a reaction solution further comprises adding a base to said reaction solution at a rate effective to maintain the pH of said reaction mixture at from about 10 to about 12.

69. The method of claim 68, wherein said base is selected from the group consisting of potassium carbonate, potassium bicarbonate, sodium bicarbonate, sodium carbonate, sodium hydroxide, sodium borate, sodium phosphate, potassium phosphate and potassium hydroxide.

70. The method of claim 63, wherein said step of producing said epoxide from said olefin is conducted at pH of about 10.5.

71. The method of claim 63, wherein said solution comprising said chiral cyclic enantiomerically enriched ketone and said olefin comprises a solvent selected from the group consisting of acetonitrile, dimethoxymethane, dimethoxyethane, water, dimethyl formamide, dioxane, dichloromethane, alcohol, and mixtures thereof.

* * * * *